United States Patent
Yegnasubramanian et al.

(10) Patent No.: US 11,491,174 B2
(45) Date of Patent: Nov. 8, 2022

(54) INDUCTION OF SYNTHETIC LETHALITY WITH EPIGENETIC THERAPY

(71) Applicant: The Johns Hopkins University, Baltimore, MD (US)

(72) Inventors: Srinivasan Yegnasubramanian, Baltimore, MD (US); William G. Nelson, Baltimore, MD (US); Ajay Vaghasia, Baltimore, MD (US); Philipp Nuhn, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/618,845

(22) PCT Filed: Jun. 6, 2018

(86) PCT No.: PCT/US2018/036220
§ 371 (c)(1),
(2) Date: Dec. 3, 2019

(87) PCT Pub. No.: WO2018/226802
PCT Pub. Date: Dec. 13, 2018

(65) Prior Publication Data
US 2021/0106603 A1 Apr. 15, 2021

Related U.S. Application Data

(60) Provisional application No. 62/515,979, filed on Jun. 6, 2017.

(51) Int. Cl.
| | | |
|---|---|---|
| *A61K 31/7068* | (2006.01) | |
| *A61P 35/00* | (2006.01) | |
| *A61K 31/203* | (2006.01) | |
| *A61K 31/4188* | (2006.01) | |
| *A61K 31/55* | (2006.01) | |

(52) U.S. Cl.
CPC ........ *A61K 31/7068* (2013.01); *A61K 31/203* (2013.01); *A61K 31/4188* (2013.01); *A61K 31/55* (2013.01); *A61P 35/00* (2018.01)

(58) Field of Classification Search
CPC .............. A61K 31/7068; A61K 31/203; A61K 31/4188
See application file for complete search history.

(56) References Cited

U.S. PATENT DOCUMENTS

| | | | |
|---|---|---|---|
| 2014/0364434 A1 | 12/2014 | Daeman et al. | |
| 2020/0138829 A1* | 5/2020 | Chen ................. | A61K 31/4178 |

FOREIGN PATENT DOCUMENTS

| | | |
|---|---|---|
| WO | WO 2009/099991 | 8/2009 |
| WO | WO 2015/035112 | 3/2015 |

OTHER PUBLICATIONS

Gravina; Molecular Cancer; 2010, 9:305.*
Young (Oncotarget; 2017, vol. 8, (No. 31), 51429-51446).*
Park (International Journal of Oncology; 45:1691-1698, 2014).*
Alvarado et al., "Methylated DNA binding domain protein 2 (MBD2) coordinately silences gene expression through activation of the microRNA hsa-mir-496 promoter in breast cancer cell line," PLoS One, Oct. 2013, 8(10), 13 pages.
Antequera et al., "Number of CpG islands and genes in human and mouse," Proc. Natl. Acad. Sci. USA, 1993, 90:11995-11999.
Belinksky et al., "Inhibition of DNA Methylation and Histone Deacetylation Prevents Murine Lung Cancer1," Cancer Research, 2003, 63:7089-7093.
Bird et al., "CpG-rich islands and the function of DNA methylation," Nature, 1986, 321:209-213.
Bird et al., "Methylation-Induced Repression—Minireview Belts, Braces, and Chromatin," Cell, 1999, 99:451-454.
Biter et al., "Targeting EZH2 methyltransferase activity in ARID1A mutated cancer cells is synthetic lethal," Nat Med. 2015, 12(3):231-238.
Bitler et al., "Synthetic lethality by targeting EZH2 methyltransferase activity in ARID1A-mutated cancers," Nat Med., 2015, 21(3)231-240.
Bliss, "The toxicity of poisons applied jointly 1," Annals of Applied Biology, Aug. 1939, 26(3):585-615.
Boettcher et al., "Pooled RNAi screens—Technical and Biological Aspects," Current Genomics, May 1, 2010, 11(3):162-7.
Brooks et al., CG island methylation changes near the GSTP1 gene in prostatic intraepithelial neoplasia. Cancer Epidemiol Biomarkers Prev 1998;7: 531-536.
Cameron et al., Synergy of demethylation and histone deacetylase inhibition in the re-expression of genes silenced in cancer. Nature genetics 1999;21: 103-7.
Carducci, et al., A Phase I clinical and pharmacological evaluation of sodium phenylbutyrate on an 120-h infusion schedule. Clin Cancer Res 2001;7: 3047-55.
Cheishvili et al., "Synergistic effects of combined DNA methyltransferase inhibition and MBD2 depletion on breast cancer cells; MBD2 depletion blocks 5-aza-2'-deoxycytidine-triggered invasiveness," Carcinogenesis, Nov. 1, 2014, 35(11):2436-46.
Cheng et al., Inhibition of DNA methylation and reactivation of silenced genes by zebularine. J Natl Cancer Inst 2003;95: 399-409.
Costello et al., Aberrant CpG-island methylation has non-random and tumour-type-specific patterns. Nature genetics 2000;24: 132-8.

(Continued)

*Primary Examiner* — Pancham Bakshi
(74) *Attorney, Agent, or Firm* — Fish & Richardson P.C.

(57) ABSTRACT

The disclosure generally relates to compositions and methods for the treatment of cancer. In some aspects, disclosed herein are methods for the induction of synthetic lethality with epigenetic therapy (ISLET) using a combination of at least one epigenetic compound and at least one chemotherapeutic agent. Also disclosed herein are screening methods for identifying compounds that induce killing of cancer cells when combined with at least one epigenetic compound. Further disclosed herein are methods of potentiating a therapeutic effect of a chemotherapeutic agent against a cancer, comprising administering to a subject having the cancer an epigenetic compound in an amount effective to potentiate the therapeutic effect of the chemotherapeutic agent against the cancer.

11 Claims, 31 Drawing Sheets

(56) References Cited

OTHER PUBLICATIONS

Covell et al., Anticancer medicines in development: assessment of bioactivity profiles within the National Cancer Institute anticancer screening data. Molecular cancer therapeutics 2007;6:2261-70.

Diehl et al., "Use of RNAi screens to uncover resistance mechanisms in cancer cells and identify synthetic lethal interactions," Drug Discovery Today: Technologies, Mar. 1, 2014, 11:11-8.

Dobzhansky, Genetics of Natural Populations. Xiii. Recombination and Variability in Populations of *Drosophila pseudoobscura*. Genetics 1946;31: 269-90.

Dudoit et al., Open source software for the analysis of microarray data. BioTechniques 2003;Suppl: 45-51.

Ferguson et al., Demethylation of the estrogen receptor gene in estrogen receptor-negative breast cancer cells can reactivate estrogen receptor gene expression. Cancer Res 1995;55: 2279-83.

Flemming et al., An epigenetic target for synthetic lethality, Nat. Rev. Drug Disc., 2015, vol. 14:1 page.

Gore et al., Combined DNA methyltransferase and histone deacetylase inhibition in the treatment of myeloid neoplasms. Cancer Res 2006;66: 6361-9.

Herman et al., Gene silencing in cancer in association with promoter hypermethylation. N Engl J Med 2003;349: 2042-54.

Kaelin et al., "The Concept of Synthetic Lethality in the Context of Anticancer Therapy," Nature Review Cancer, 2005, 5:689-698.

Kaminskas et al., Approval summary: azacitidine for treatment of myelodysplastic syndrome subtypes. Clin Cancer Res 2005;11: 3604-8.

Kato et al., Antitumor effect of the histone deacetylase inhibitor LAQ824 in combination with 13-cis-retinoic acid in human malignant melanoma. Molecular cancer therapeutics 2007;6:70-81.

Kelly et al., Phase I clinical trial of histone deacetylase inhibitor: suberoylanilide hydroxamic acid administered intravenously. Clin Cancer Res 2003;9: 3578-88.

Kelly et al., Phase I study of an oral histone deacetylase inhibitor, suberoylanilide hydroxamic acid, in patients with advanced cancer. J Clin Oncol 2005;23: 3923-31.

Lin et al., Reversal of GSTP1 CpG island hypermethylation and reactivation of piclass glutathione S-transferase (GSTP1) expression in human prostate cancer cells by treatment with procainamide. Cancer Res 2001;61: 8611-6.

Matthay et al., "Treatment of high-risk neuroblastoma with intensive chemotherapy, radiotherapy, autologous bone marrow transplantation, and 13-cis-retinoic acid," New England Journal of Medicine, Oct. 14, 1999, 341(16):1165-73.

Nakayama et al., Hypermethylation of the human glutathione S-transferase-pi gene (GSTP1) CpG island is present in a subset of proliferative inflammatory atrophy lesions but not in normal or hyperplastic epithelium of the prostate: a detailed study using laser-capture microdissection. Am J Pathol 2003;163: 923-33.

Nijman et al., "Synthetic lethality: General principles, utility and detection using genetic screens in human cells," FEBS Letters, 2011, 585:1-6.

Ottaviano et al., Methylation of the estrogen receptor gene CpG island marks loss of estrogen receptor expression in human breast cancer cells. Cancer Res 1994;54: 2552-5.

PCT International Report on Patentability in International Appln. No. PCT/US2018/036220, dated Dec. 10, 2019, 9 pages.

PCT International Search Report and Written Opinion in International Appln. No. PCT/US2018/036220, dated Dec. 10, 2019, 11 pages.

Pfister et al., "Marked for death: targeting epigenetic changes in cancer," Nat Rev Drug Discov., 2017, 16:241-263.

Pill et al., Combination of phenylbutyrate and 13-cis retinoic acid inhibits prostate tumor growth and angiogenesis. Cancer Res 2001;61: 1477-85.

Qian et al., In vivo imaging of retinoic acid receptor beta2 transcriptional activation by the histone deacetylase inhibitor MS-275 in retinoid-resistant prostate cancer cells. The Prostate 2005;64:20-8.

Raynal et al., "Repositioning FDA-approved drugs in combination with epigenetic drugs to reprogram colon cancer epigenome," Molecular Cancer Therapeutics, Feb. 1, 2017, 16(2):397-407.

Robinson et al., edgeR: a Bioconductor package for differential expression analysis of digital gene expression data. Bioinformatics (Oxford, England) 2010;26: 139-40.

Schlabach et al., "Cancer proliferation gene discovery through functional genomics," Science, Feb. 1, 2008, 319(5863):620-4.

Schuebel et al., Comparing the DNA hypermethylome with gene mutations in human colorectal cancer. PLoS genetics 2007;3: 1709-23.

Segura-Pacheco et al., Reactivation of tumor suppressor genes by the cardiovascular drugs hydralazine and procainamide and their potential use in cancer therapy. Clin Cancer Res 2003;9: 1596-603.

Shalem et al., "Genome-scale CRISPR-Cas9 knockout screening in human cells," Science, Jan. 3, 2014, 343(6166):84-7.

Sharma et al., Restoration of tamoxifen sensitivity in estrogen receptor-negative breast cancer cells: tamoxifen-bound reactivated ER recruits distinctive corepressor complexes. Cancer Res 2006;66: 6370-8.

Silva et al., "Second-generation shRNA libraries covering the mouse and human genomes," Nature Genetics, Nov. 2005, 37(11):1281-1288.

Sirchia et al., Endogenous reactivation of the RARbeta2 tumor suppressor gene epigenetically silenced in breast cancer. Cancer Res 2002;62: 2455-61.

Tong et al., Systematic genetic analysis with ordered arrays of yeast deletion mutants. Science (New York, NY 2001;294: 2364-8.

Wang et al., Epigenetic modulation of retinoic acid receptor beta2 by the histone deacetylase inhibitor MS-275 in human renal cell carcinoma. Clin Cancer Res 2005;11: 3535-42.

Westbrook el al., "A genetic screen for candidate tumor suppressors identifies REST," Cell, Jun. 17, 2005, 12 1(6):837-48.

Wyhs et al., "Time-resolved fluorescence resonance energy transfer assay for discovery of small-molecule inhibitors of methyl-CpG binding domain protein 2," Journal of Biomolecular Screening, Aug. 19, 2014, 19(7):1060-9.

Yang et al., Synergistic activation of functional estrogen receptor (ER)-alpha by DNA methyltransferase and histone deacetylase inhibition in human ER-alpha-negative breast cancer cells. Cancer Res 2001;61: 7025-9.

Yang et al., Transcriptional activation of estrogen receptor alpha in human breast cancer cells by histone deacetylase inhibition. Cancer Res 2000;60: 6890-4.

Yegnasubramanian et al., Hypermethylation of CpG islands in primary and metastatic human prostate cancer. Cancer Res 2004;64: 1975-86.

Zullo et al., "Aurora a kinase inhibition selectivelv synergizes with histone deacetylase inhibitor through cytokinesis failure in T-cell lymphoma," Clinical Cancer Research, Sep. 15, 2015, 21(18):4097-109.

European Extended Search Report and Written Opinion in International Appln. No. PCT/US2018/036220, dated Jan. 28, 2021, 13 pages.

Gores et al., "Combination therapy with DNA methyltransferase inhibitors in hematologic malignancies," Nature Clinical Practice Oncology, Nature Publishing Group, US, 2005, 2(Suppl. 1):S30-S35.

Giovi Nazzo et al.: 11A high-throughput screen of pharmacologically active compounds for inhibitors of UHRF1 reveals epigenetic activity of anthracycline derivative chemotherapeutic drugs, ONCOTARGET, 2019, 10(32):3040-3050.

Lessing et al: "A high-throughput small molecule screen identifies synergism between DNA methylation and Aurora kinase pathways for X reactivation", Proceedings of the National Academy of Sciences, 2016, 113(50):14366-14371.

Walker et al: ""Abstract 5390: Development of a high-throughput screening assay to identify UHRF1 inhibitors via timeresolved fluorescence resonance energy transfer (TRFRET)"", AACR Annual Meeting 2014.

(56) References Cited

OTHER PUBLICATIONS

European Extended Search Report and Written Opinion in International Appln. No. PCT/US2018/036220, dated Apr. 29, 2021, 14 pages.

* cited by examiner

Vehicle

Decitabine-Pretreatment Decitabine

Alisertib

Pretreatment+Alisertib

Vehicle

Decitabine-Pretreatment Decitabine

Alisertib

Pretreatment+Alisertib

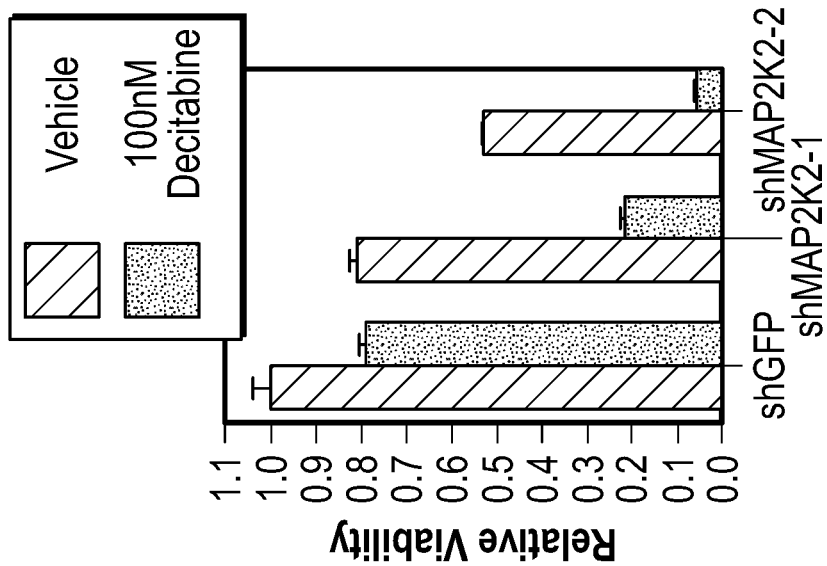
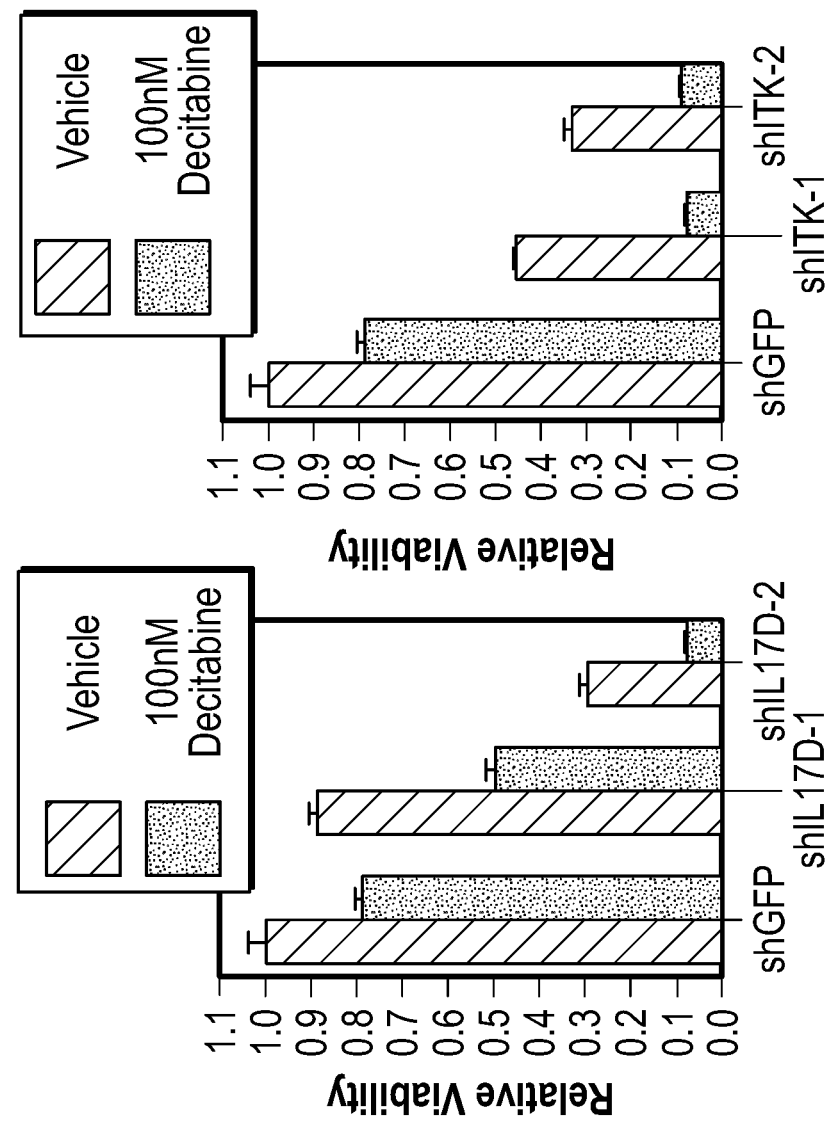
FIG. 23
FIG. 22
FIG. 21

INDUCTION OF SYNTHETIC LETHALITY WITH EPIGENETIC THERAPY

CROSS-REFERENCE TO RELATED APPLICATIONS

This application is a National Stage application under 35 U.S.C. § 371 of International Application No. PCT/US2018/036220 having an International Filing Date of Jun. 6, 2018, which claims the benefit of U.S. Patent Application No. 62/515,979, filed on Jun. 6, 2017. The disclosure of the prior applications are considered part of (and is incorporated by reference in) the disclosure of this application.

STATEMENT REGARDING FEDERALLY SPONSORED RESEARCH OR DEVELOPMENT

This invention was made with government support under award numbers R01CA113374, R03MH098712, and P50CA058236 by the National Institute of Health/National Cancer Institute. The government has certain rights in this invention.

FIELD OF THE INVENTION

The disclosure generally relates to combination therapy for the treatment of cancer, as well as screening methods for identifying compounds that can be used in combination to treat cancer.

BACKGROUND

Cancer continues to be a significant health problem and a leading cause of death worldwide. Remarkable improvements have been made in understanding the genetic basis of cancer, and considerable research has focused on specific genes that may be involved in the development of specific cancers. Oncogenes are genes that, when overexpressed, result in cancer, while tumor suppressor genes are genes that, when underexpressed, may result in cancer. Accordingly, the ability to control both oncogenes and tumor suppressor genes medicinally is of great value.

Recently, researchers have been interested in gaining a better understanding of the epigenetic factors involved in cancer and the control of both oncogenes and tumor suppressor genes. Epigenetics involves the phenotypes that arise due to factors other than the DNA sequence of a cell or organism. Alterations of epigenetic markers on DNA and histones can mediate repression of tumor suppressor genes and activation of oncogenes. Reversal of such alterations by inhibiting the epigenetic enzymes and/or machinery responsible for "writing," "erasing," and "reading" the epigenetic marks is thus an attractive cancer therapeutic strategy.

For example, DNA methylation is a chemical modification of DNA that can be performed by enzymes known as methyltransferases, in which a methyl group is added to certain cytosines of DNA. This epigenetic process, while not altering the genotype, is nonetheless important in gene expression regulation. DNA methyltransferases catalyze the transfer of methyl groups onto DNA strands. In cancer, DNA methyltransferases may cause hypermethylation to occur, wherein DNA becomes over-methylated, acting to silence genes, including, for example, tumor suppressor genes and DNA repair genes. Methylated-DNA binding (MBD) proteins can also contribute to DNA hypermethylation during cancer development and progression. MBD proteins function as "epigenetic readers," recruiting co-repressor complexes to promote gene repression. The MBD protein MBD2, for example, binds the GSTP1 promoter CpG island when it is aberrantly methylated in cancer cells. Hypermethylation of the GSTP1 promoter CpG island and accompanying epigenetic gene silencing of GSTP1 occurs frequently in several cancer types, including, for example, prostate, breast, and liver cancers. Inhibiting MBD-mediated repression has therefore become of interest in cancer research.

Therefore, it is believed that DNA methylation may be an important mechanism in the study of epigenetic cancer research. Certain DNA methyltransferase inhibitors, such as decitabine, have demonstrated chemotherapeutic efficacy. Methylated-DNA-binding protein inhibitors and DNA methyltransferase inhibitor drugs such as decitabine, however, have had limited success in the clinical setting at least partially due to their inefficacy or toxicities at therapeutically effective dosages.

In addition to epigenetic compounds, there are also a wide range of chemotherapeutic agents currently available for treatment. Chemotherapeutic agents however, may have several drawbacks, including high toxicity levels to healthy cells and varying levels of efficacy.

One known chemotherapeutic agent is Aurora kinase A inhibitors. Aurora kinases are enzymes linked to protein expression that are integral for mitotic processes, including centrosome maturation, chromosome alignment, chromosome segregation, and cytokinesis. The over-expression of Aurora kinase A is a distinguishing feature of many human malignant tumors. Accordingly, Aurora kinase A inhibitors are of interest to cancer researchers. However, like decitabine, the Aurora kinase A inhibitors, such as alisertib, have only shown modest chemotherapeutic activity in vivo, and are also limited in part due to toxicities at doses needed to achieve this modest activity.

Another known chemotherapeutic agent includes retinoic acid receptor (RAR) agonists, such as isotretinoin. Retinoic acid receptors mediate the response of retinoids in the body by binding to retinoic acid response elements of target genes. Upon binding of retinoic acid or other agonists, RARs can recruit coactivator proteins and mediate the transcription of target genes. Retinoids interact with other signaling pathways, and can promote differentiation and anti-proliferative signals; suppression of the retinoid signaling pathway has been associated with tumor development in cancers. However, RAR agonists such as isotretinoin, like the Aurora kinase A inhibitor alisertib, have not shown promising chemotherapeutic activity in vivo for the majority of cancer types as single agents.

There is thus a need in the field for improved chemotherapeutic treatments and continued research to identify compounds for the induction of synthetic lethality of cancer cells with epigenetic therapy. Furthermore, there is a need for effective chemotherapeutic treatments that have minimal or no cytotoxicity to non-malignant cells.

SUMMARY OF THE INVENTION

Disclosed herein are methods of screening for compounds that induce killing of cancer cells when combined with at least one epigenetic compound, comprising treating cancer cells with an epigenetic compound, wherein the cancer cells have been made to lose function of at least one gene or gene product. For example, in certain embodiments, the cancer cells may be treated with a library of agents thought to inhibit a target gene or gene product. In exemplary embodiments, the library of agents may be chosen from shRNA libraries, siRNA libraries, small molecule libraries, insertional mutagenesis libraries, CRISPR/Cas sgRNA libraries, and CRISPR/catalytically inactive dCas sgRNA libraries.

In embodiments, disclosed herein is a method for screening compounds that induce killing of cancer cells when combined with at least one epigenetic compound, comprising treating the cancer cells with an epigenetic compound, wherein the cancer cells have been transduced, for example with a shRNA library, wherein the shRNA library contains a plurality of shRNAs, each of which is specific for a target gene, and identifying the shRNAs of the transduced cancer cells that did not survive treatment with the epigenetic compound, and identifying the compound that induces killing of cancer cells when combined with the epigenetic compound as an inhibitor of the target gene of the shRNAs of the transduced cancer cells that did not survive treatment with the epigenetic compound or an inhibitor of a polypeptide encoded by the target gene. In certain embodiments, the epigenetic compound is chosen from DNA demethylating agents, histone deacetylase inhibitors, histone methyltransferase inhibitors, and methylated-DNA binding protein inhibitors. In certain embodiments, the epigenetic compound is a DNA methyltransferase inhibitor, and in certain embodiments, the epigenetic compound is decitabine. In other embodiments, the epigenetic compound is a methylated-DNA binding protein inhibitor, and in certain embodiments, the epigenetic compound is KCC-08. In certain embodiments, the shRNA library is a pooled lentiviral shRNA library.

Further disclosed herein are methods for treating cancer comprising administering to a subject in need thereof an effective amount of at least one epigenetic compound and an effective amount of at least one chemotherapeutic agent. In certain embodiments, the effective amount of the at least one epigenetic compound and the effective amount of at least one chemotherapeutic agent act synergistically to inhibit the growth of cancer cells. In certain embodiments, disclosed herein is a method of treating cancer comprising administering to a subject in need thereof an effective amount of at least one DNA methyltransferase inhibitor and an effective amount of at least one Aurora kinase A inhibitor, and, in other embodiments, disclosed herein is a method of treating cancer comprising administering to a subject in need thereof an effective amount of at least one MBD protein inhibitor and an effective amount of at least one RAR agonist. In certain embodiments, the effective amount of the at least one epigenetic compound, such as DNA methyltransferase inhibitor or MBD protein inhibitor, and the effective amount of the at least one chemotherapeutic, such as Aurora kinase A inhibitor or RAR agonist, act synergistically to inhibit growth of cancer cells. In certain embodiments, the at least one DNA methyltransferase inhibitor is decitabine, and in certain embodiments, the at least one Aurora kinase A inhibitor is alisertib. In other embodiments disclosed herein, the at least one MBD protein inhibitor is KCC-08, and the at least one RAR agonist is isotretinoin.

In certain embodiments, the effective amount of decitabine administered in a single administration over a 24-hour period is less than 25 mg/m² and in certain embodiments the effective amount of decitabine administered in more than a single administration over a 24-hour period is less than 150 mg/m². In some aspects, the effective amount of at least one Aurora kinase A inhibitor administered in a cycle ranges from less than about 70 mg to about 1050 mg.

In certain embodiments, the effective amount of KCC-08 administered in a single administration over a 24-hour period is less than about 5 mg/kg, and in certain embodiments the effective amount of KCC-08 administered in more than a single administration over a 24-hour period is less than about 25 mg/kg, such as about 1 mg/kg/day or about 0.5 mg/kg/day. In some aspects, the effective amount of at least one RAR agonist administered in a cycle ranges from less than about 30 mg/kg/day to less than about 60 mg/kg/day, such as about 30 mg/kg/day.

In certain embodiments disclosed herein, the cancer is chosen from prostate cancer, ovarian cancer, lung cancer, colorectal cancer, central nervous system cancer, and breast cancer. In certain embodiments, the subject in need of treatment is human.

In specific embodiments disclosed herein, the administration of the at least one epigenetic compound and the administration of the at least one chemotherapeutic agent is sequential. In certain embodiments, when the at least one epigenetic compound and the at least one chemotherapeutic agent are administered sequentially, the at least one epigenetic compound is administered first. In other embodiments disclosed herein, the administration of the at least one epigenetic compound and the administration of the at least one chemotherapeutic agent is simultaneous.

Also disclosed herein is a method of potentiating a therapeutic effect of a chemotherapeutic agent against a cancer, comprising administering to a subject having the cancer an epigenetic compound in an amount effective to potentiate the therapeutic effect of the chemotherapeutic agent against the cancer. In certain aspects, the method further comprises administering to the subject a therapeutically effective amount of the chemotherapeutic agent, and in certain aspects, the therapeutically effective amount of the chemotherapeutic agent is not therapeutically effective when administered without the epigenetic compound. In certain embodiments of the methods disclosed herein, the epigenetic compound is a DNA methyltransferase inhibitor such as decitabine, and in certain embodiments of the methods disclosed herein, the chemotherapeutic agent is an Aurora kinase A inhibitor, such as alisertib. In certain embodiments of the methods disclosed herein, the epigenetic compound is a MBD protein inhibitor such as KCC-08, and in certain embodiments of the methods disclosed herein, the chemotherapeutic agent is a RAR agonist, such as isotretinoin.

Figure 16:
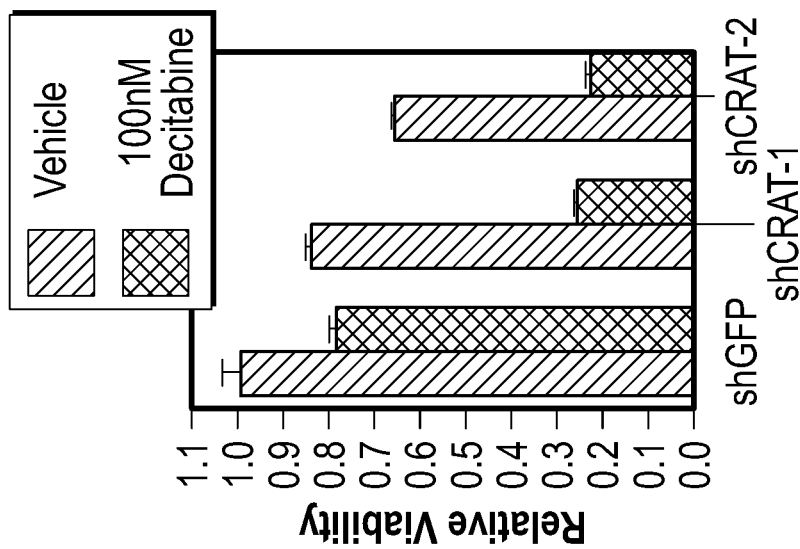

FIG. 16 is a bar graph illustrating DU145 cells treated with two different shRNA sequences targeting CRAT, each combined with vehicle control or 100 nM decitabine, compared to DU145 cells treated with non-targeting shRNAs (shGFP) in combination with a vehicle control and with 100 nM decitabine.

Figure 17:
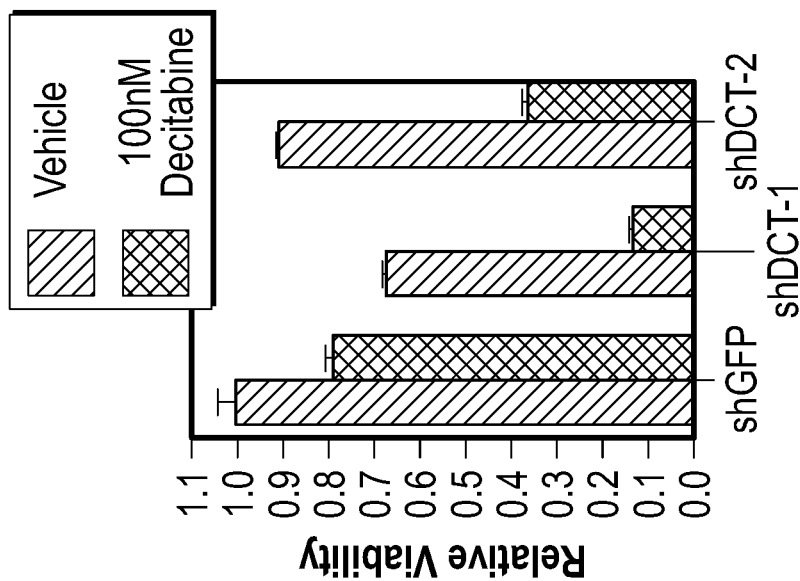

FIG. 17 is a bar graph illustrating DU145 cells treated with two different shRNA sequences targeting DCT, each combined with vehicle control or 100 nM decitabine, compared to DU145 cells treated with non-targeting shRNAs (shGFP) in combination with a vehicle control and with 100 nM decitabine.

Figure 18:
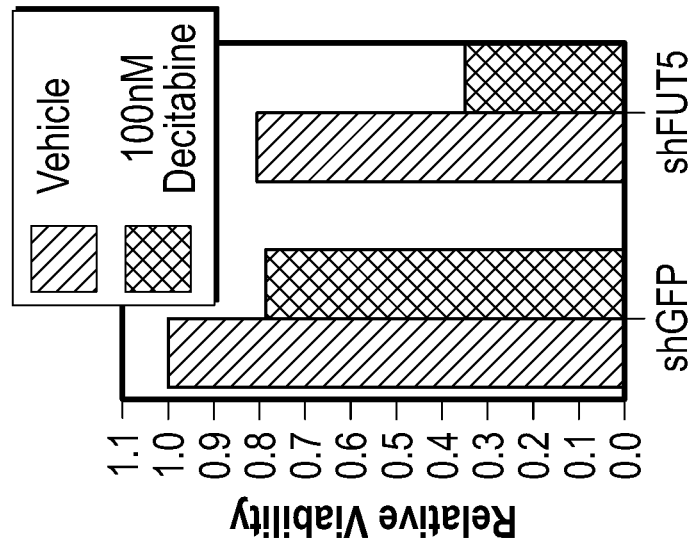

FIG. 18 is a bar graph illustrating DU145 cells treated with an shRNA sequence targeting FUT5 combined with vehicle control or 100 nM decitabine, compared to DU145 cells treated with non-targeting shRNAs (shGFP) in combination with a vehicle control and with 100 nM decitabine.

Figure 19:
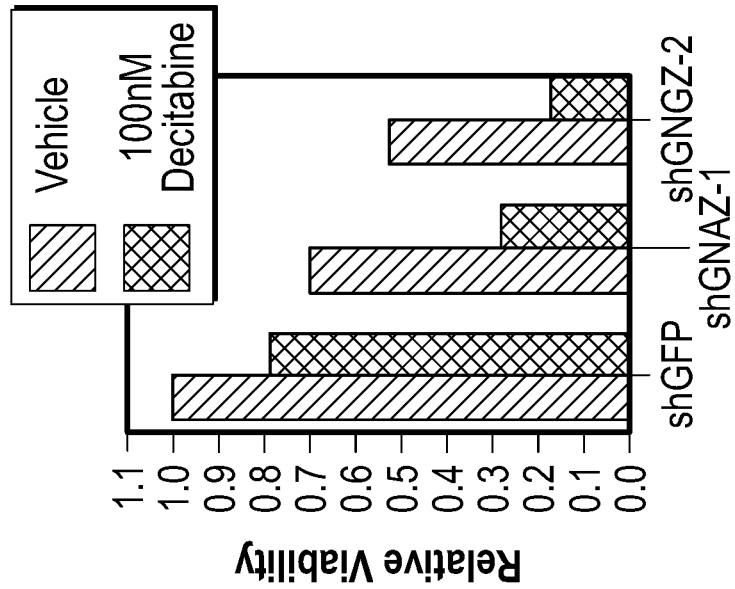

FIG. 19 is a bar graph illustrating DU145 cells treated with two different shRNA sequences targeting GNAZ, each combined with vehicle control or 100 nM decitabine, compared to DU145 cells treated with non-targeting shRNAs (shGFP) in combination with a vehicle control and with 100 nM decitabine.

Figure 20:
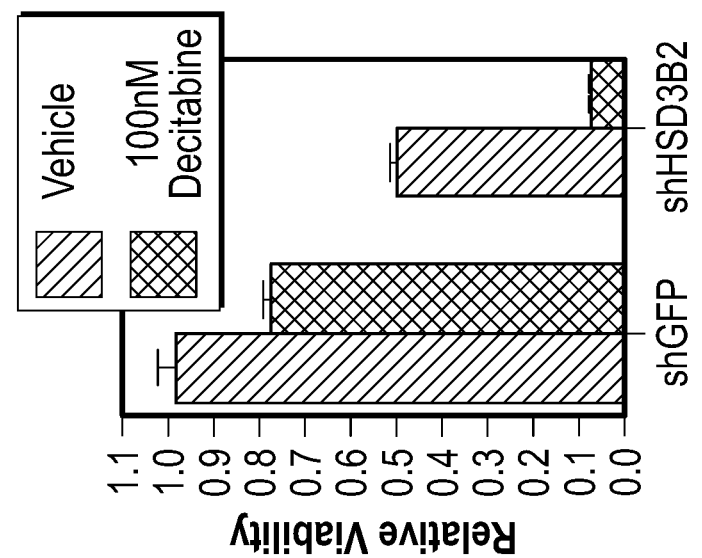

FIG. 20 is a bar graph illustrating DU145 cells treated with an shRNA sequence targeting HSD3B2 combined with vehicle control or 100 nM decitabine, compared to DU145 cells treated with non-targeting shRNAs (shGFP) in combination with a vehicle control and with 100 nM decitabine.

FIG. 21 is a bar graph illustrating DU145 cells treated with two different shRNA sequences targeting IL17D, each combined with vehicle control or 100 nM decitabine, compared to DU145 cells treated with non-targeting shRNAs (shGFP) in combination with a vehicle control and with 100 nM decitabine.

FIG. 22 is a bar graph illustrating DU145 cells treated with two different shRNA sequences targeting ITK, each combined with vehicle control or 100 nM decitabine, compared to DU145 cells treated with non-targeting shRNAs (shGFP) in combination with a vehicle control and with 100 nM decitabine.

FIG. 23 is a bar graph illustrating DU145 cells treated with two different shRNA sequences targeting MAP2K2, each combined with vehicle control or 100 nM decitabine, compared to DU145 cells treated with non-targeting shRNAs (shGFP) in combination with a vehicle control and with 100 nM decitabine.

Figure 24:
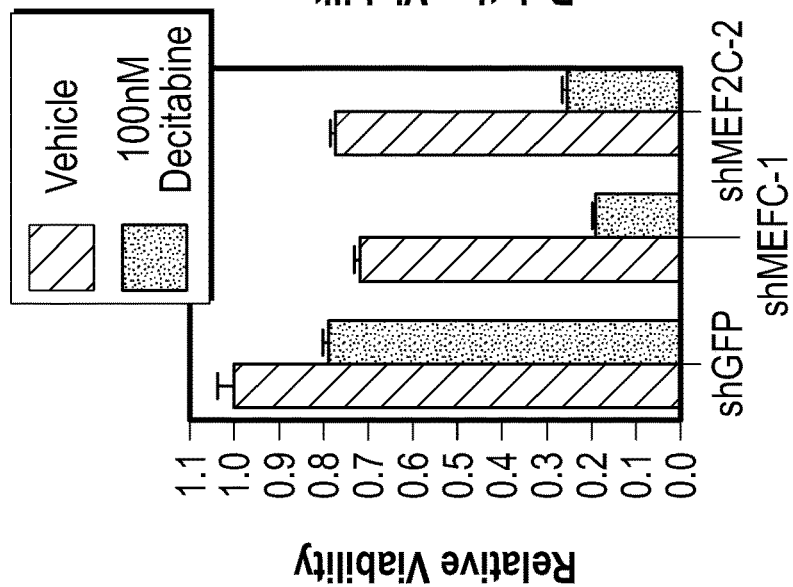

FIG. 24 is a bar graph illustrating DU145 cells treated with two different shRNA sequences targeting MEF2C, each combined with vehicle control or 100 nM decitabine, compared to DU145 cells treated with non-targeting shRNAs (shGFP) in combination with a vehicle control and with 100 nM decitabine.

Figure 25:
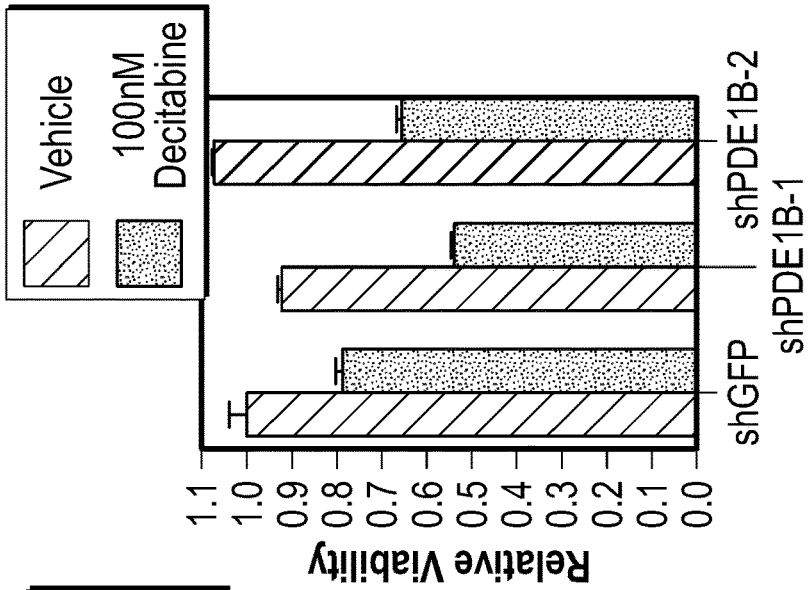

FIG. 25 is a bar graph illustrating DU145 cells treated with two different shRNA sequences targeting PDE1B, each combined with vehicle control or 100 nM decitabine, compared to DU145 cells treated with non-targeting shRNAs (shGFP) in combination with a vehicle control and with 100 nM decitabine.

Figure 26:
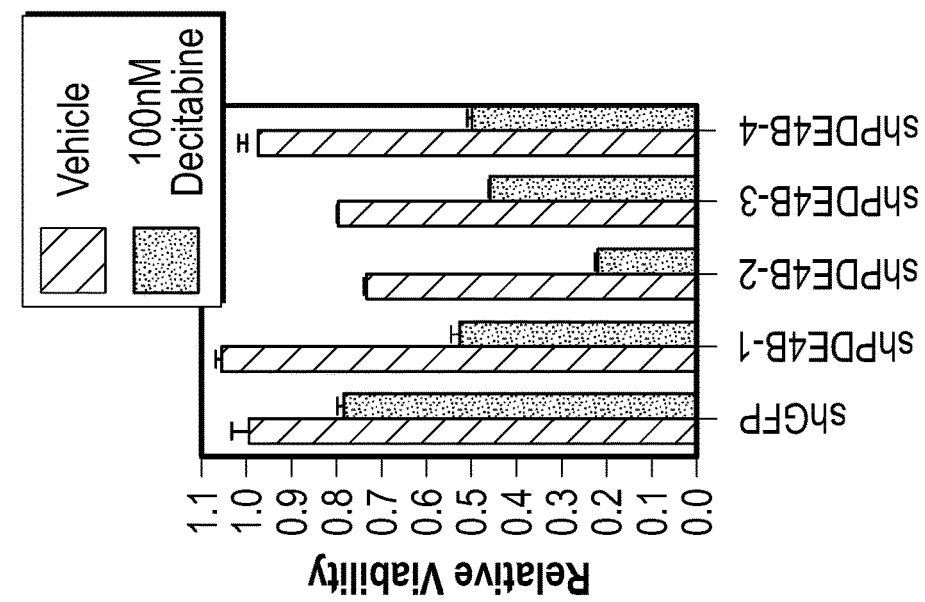

FIG. 26 is a bar graph illustrating DU145 cells treated with four different shRNA sequences targeting PDE4B, each combined with vehicle control or 100 nM decitabine, compared to DU145 cells treated with non-targeting shRNAs (shGFP) in combination with a vehicle control and with 100 nM decitabine.

Figure 27:
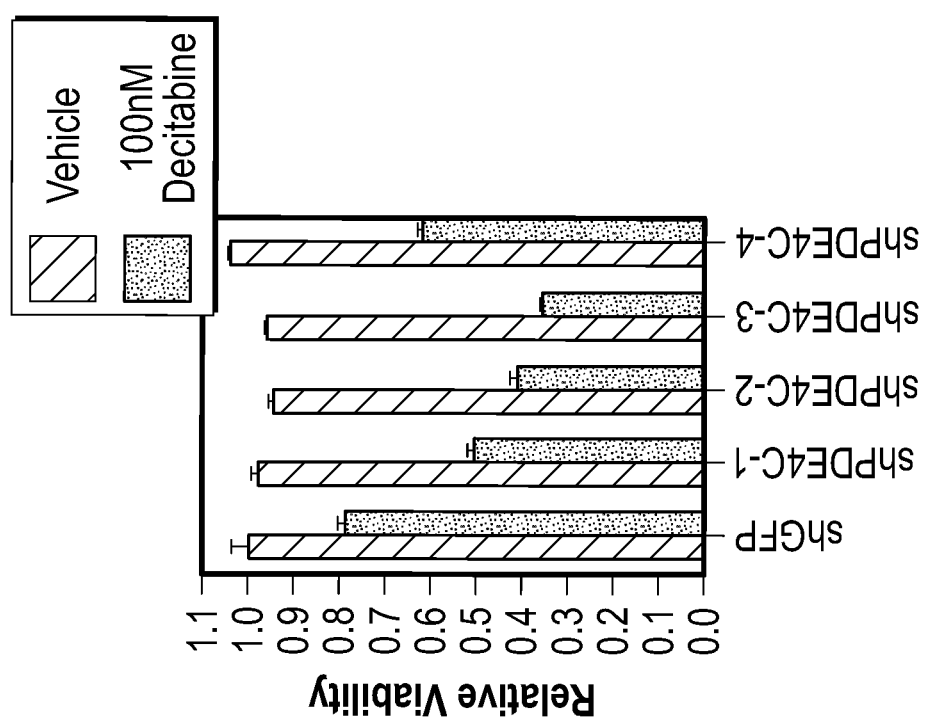

FIG. 27 is a bar graph illustrating DU145 cells treated with four different shRNA sequences targeting PDE4C, each combined with vehicle control or 100 nM decitabine, compared to DU145 cells treated with non-targeting shRNAs (shGFP) in combination with a vehicle control and with 100 nM decitabine.

Figure 28:
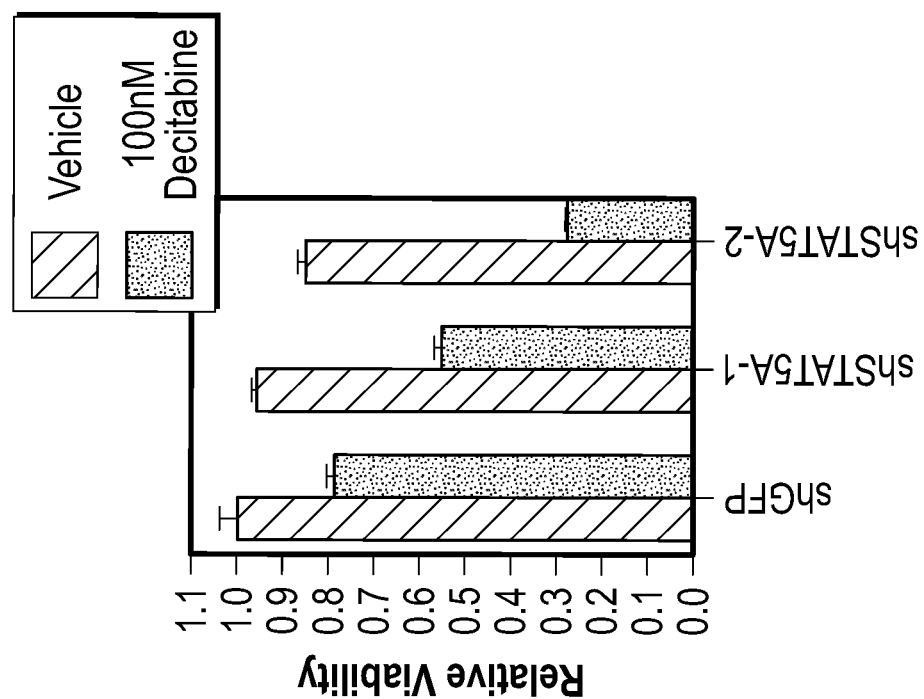

FIG. 28 is a bar graph illustrating DU145 cells treated with two different shRNA sequences targeting STAT5A, each combined with vehicle control or 100 nM decitabine, compared to DU145 cells treated with non-targeting shRNAs (shGFP) in combination with a vehicle control and with 100 nM decitabine.

Figures 29A, 29B:
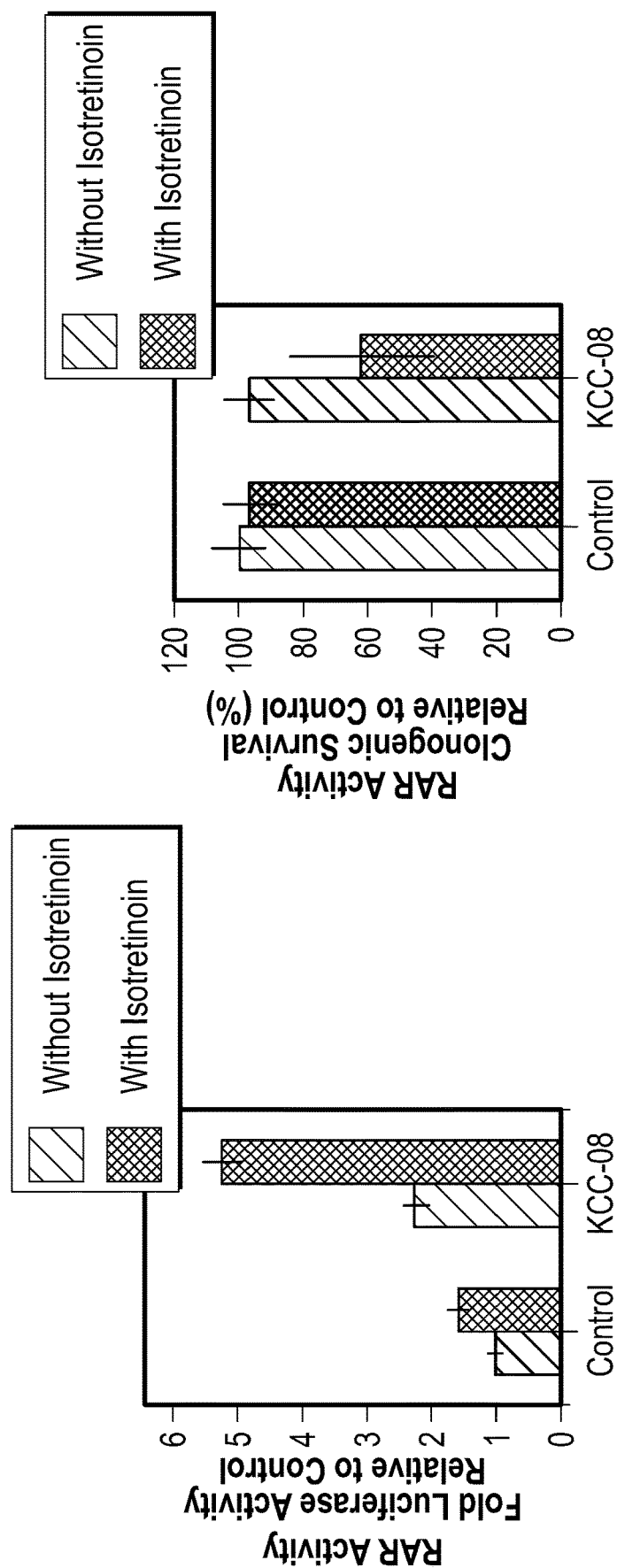

FIG. 29A is a bar graph showing the reactivation of retinoid signaling in PC-3 cells treated with KCC-08 both with and without isotretinoin.

FIG. 29B is a bar graph showing clonogenic survival in PC-3 cells treated with KCC-08 both with an without isotretinoin.

Figure 29C:
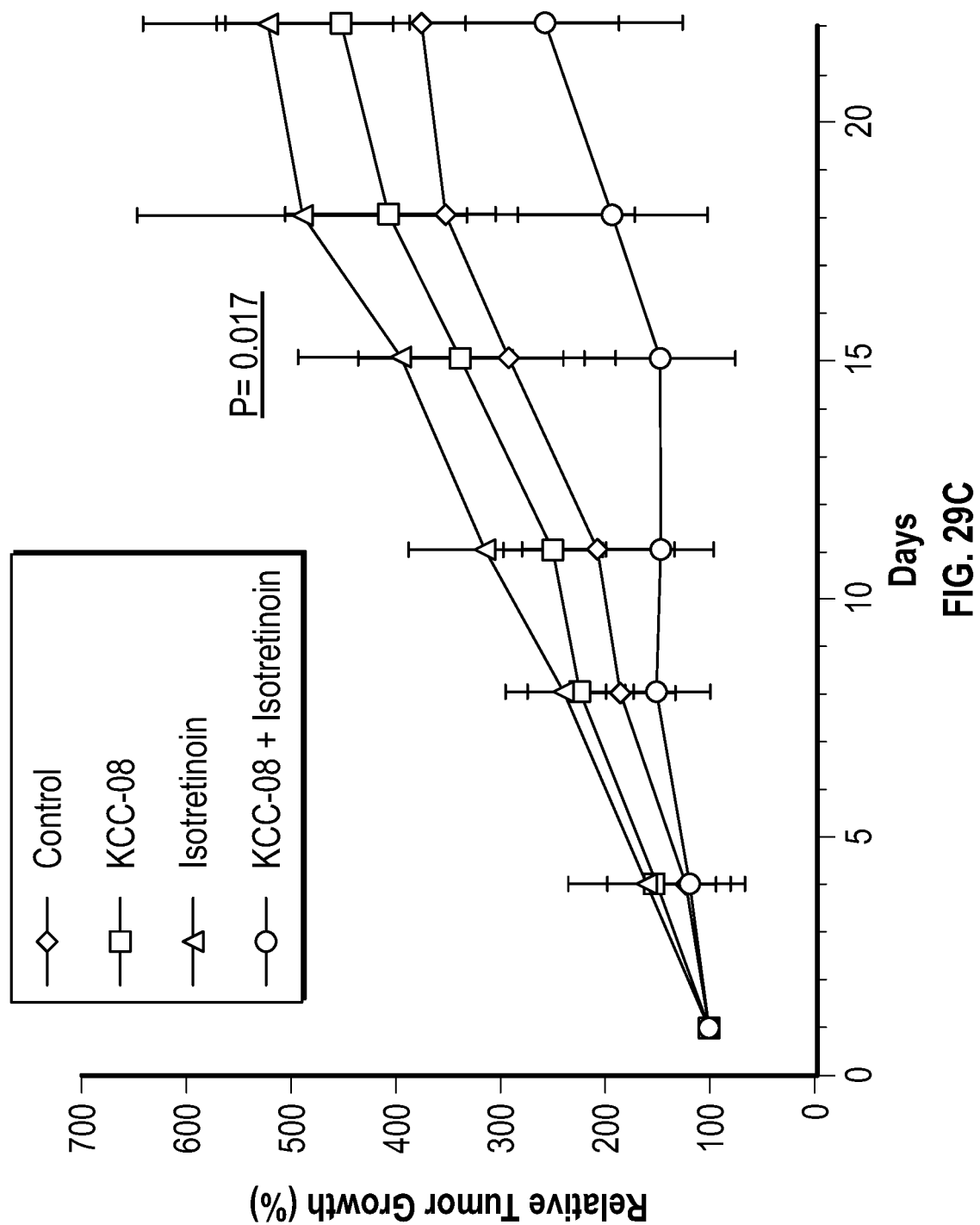

FIG. 29C is graph showing the PC-3 xenograft tumor growth in nude mice treated with a vehicle control, KCC-08 alone, isotretinoin alone, and a combination of both KCC-08 and isotretinoin, given at the doses and schedules indicated in Example 8.

Figure 30:
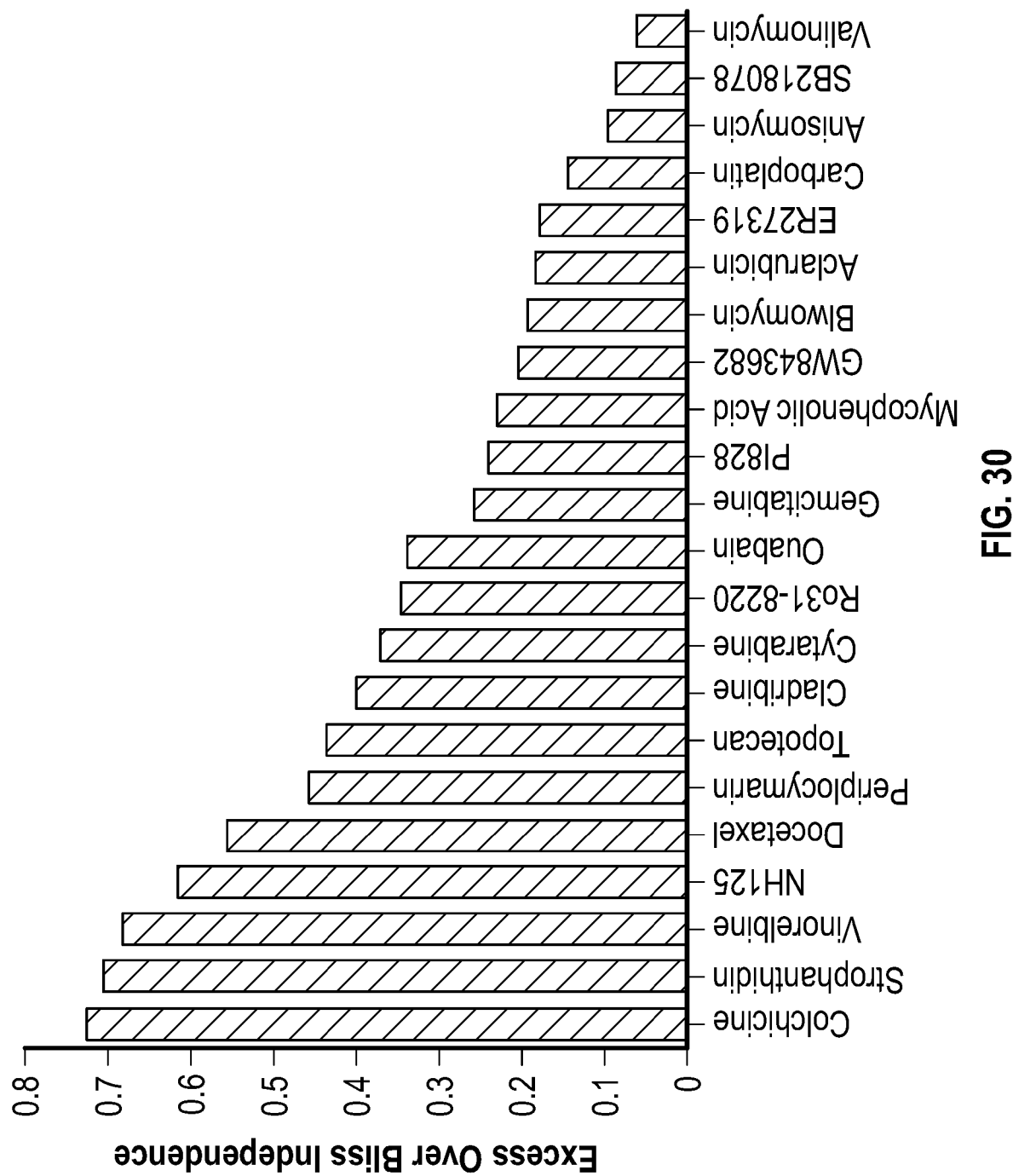

FIG. 30 is a bar graph showing the excess over Bliss Independence score values for PC-3 cancer cells treated with decitabine administered prior to administration of 22 different compounds.

DETAILED DESCRIPTION OF THE INVENTION

Disclosed herein are methods of screening compounds for the induction of synthetic lethality with epigenetic therapy (ISLET). In the past, new drug combinations have typically been identified by randomly combining two drugs that are each known to have some therapeutic efficacy and assessing the therapeutic effect and toxicity of the combination. The ISLET screening method, on the other hand, provides a new, systematic platform for identifying unique drug combinations. Typically, the drug combination includes an epigenetic compound and a chemotherapeutic agent. Without intending to be bound by any theory, it appears that exposure to the epigenetic compound, typically given at a low dosage with little to no toxicity, modifies cancer cells in a way that exposes the cancer cells to new vulnerabilities, thus making the cancer cells susceptible to other chemotherapeutic agents that target one of the newly exposed vulnerabilities. Using this screening platform, chemotherapeutic agents have been identified that have little to no therapeutic effect on cancer cells when administered at non-toxic doses without the epigenetic compound but surprisingly demonstrate therapeutic effects when administered in combination with the epigenetic compound. Compounds other than epigenetic compounds and/or chemotherapeutic agents can also be plugged into this unique, screening platform design, to identify new, therapeutic drug combinations for cancer.

In certain embodiments, the screening method comprises treating cancer cells with an agent such that the cancer cells are made to lose function of at least one gene or gene product, for example treating the cancer cells from a library of agents, wherein at least one agent inhibits a target gene or gene product; then treating the cancer cells with a compound, such as an epigenetic compound; identifying the target gene of the treated cancer cells that did not survive treatment with the epigenetic compound; and identifying the compound that induces killing of cancer cells when combined with the epigenetic compound as an inhibitor of the target gene or gene product of the cancer cells that did not survive treatment with the epigenetic compound. As used herein, the term "gene product" refers to any material resulting from expression of a gene, such as RNA, polypeptides, and proteins.

In certain embodiments the screening method comprises transducing cancer cells with an shRNA library, treating the transduced cancer cells with a compound, such as an epigenetic compound, and identifying the shRNAs of the transduced cancer cells that did not survive treatment with the compound. In certain embodiments, the epigenetic compound is a DNA demethylating agent, a histone deacetylase inhibitor, a histone methyltransferase inhibitor, or an MBD protein inhibitor. In certain embodiments, the compound is a DNA methyltransferase inhibitor, and in certain embodiments, the compound is decitabine. In certain other embodiments, the compound is an MBD protein inhibitor, such as KCC-08, KCC-03, and KCC-07. In certain embodiments, the shRNA library is a pooled lentiviral shRNA library. In certain embodiments the screening method comprises transducing cancer cells with a CRIPSR-Cas9 sgRNA screening library, which, for example, may comprise comprising a Cas9 endonuclease or dCas9 catalytically inactive mutant, a CRISPR RNA (crRNA), and a transactivating RNA (tracrRNA) to create a pooled knockout cell library, treating the transduced cancer cells with a compound, such as an epigenetic compound, and identifying the sgRNAs of the transduced cancer cells that did not survive treatment with the compound. The crRNA and tracrRNA may be combined into a single guide RNA ("sgRNA").

Epigenetic therapy relates to the use of drugs to influence gene expression without altering the nucleic acid sequence of the gene(s). As used herein, an "epigenetic compound" is a compound that affects the expression of a gene without altering the nucleic acid sequence (genotype) of the gene. For example, DNA methyltransferases act to chemically modify DNA by methylating certain cytosine residues of the DNA that are followed by guanine residues. As other example, MBD protein inhibitors act to inhibit binding of methyl-CpG binding proteins to DNA, which in turn results in a reduction of the promotion of chromatin condensation and inactivation. Other examples of epigenetic modifications include histone modifications and microRNA regulations. These epigenetic processes, while not altering the genotype, are nonetheless important in gene expression and protein regulation. Furthermore, the modifications induced by epigenetic compounds typically affect cancer cells differently than non-cancerous cells. For example, in cancer, DNA methyltransferases may cause hypermethylation to occur, where DNA becomes over-methylated, acting to silence genes, including, for example, tumor suppressor genes and DNA repair genes. Epigenetic compounds, such as DNA methyltransferase inhibitors, may therefore have chemotherapeutic effect by inhibiting the action of the DNA methyltransferases, which are active in malignant cells. Many known DNA methyltransferase inhibitors, however, such as decitabine, either have low chemotherapeutic activity in vivo or their toxicity of non-malignant cells at chemotherapeutic levels is intolerable, limiting their use as chemotherapeutic agents.

As disclosed herein, it has been discovered that epigenetic compounds may be combined with other chemotherapeutic agents to induce synthetic lethality in cancer cells. In certain embodiments, the therapeutic effect of the combination of an epigenetic compound with a chemotherapeutic agent may be synergistic, meaning the therapeutic effect of the combination is greater than either the epigenetic compound or the chemotherapeutic agent separately or the sum of the two, as discussed infra. This induction of synthetic lethality with epigenetic therapy is surprising and unexpected.

ISLET provides a new screening platform for identifying unique combinations of chemotherapeutic agents. In certain embodiments, disclosed herein are methods for screening compounds for ISLET comprising treating cancer cells with a library of agents wherein at least one agent inhibits a target gene or gene product (such as a polypeptide). For example, in certain embodiments, the screening methods disclosed herein may comprise transducing cancer cells with a shRNA library, treating the transduced cells with a compound, and identifying the shRNAs of the cells that did not survive treatment of the compound. shRNAs are short hairpin RNAs, which are artificially synthesized small RNA molecules comprising a hairpin turn and are known in the art. Schlabach M. R. et al., *Cancer Proliferation Gene Discovery through Functional Genomics*, SCIENCE, 319, 5863:620-4 (2008). shRNAs include a region that is complementary to a section of a target gene of interest, thereby making the shRNA specific for the target gene of interest. As such, the shRNA may be used to down regulate or upregulated expression of the specific target gene of interest.

In certain embodiments, the cancer cells are transduced with shRNA by means of a retroviral or lentiviral delivery of the shRNA. In certain embodiments, the cancer cells are transduced with shRNA by means of a lentiviral vector. In certain embodiments, the lentiviral vector comprises a shRNA that is specific for a target gene; a means for identifying the shRNA, such as a nucleic acid having a unique identifying nucleotide sequence; an antibiotic resistance gene; and a marker gene to track transduction levels, such as a fluorescence marker gene. In certain embodiments, the target gene is a gene that encodes a protein known to or suspected of playing a role in the cancer.

The shRNA transduced cancer cells may then be harvested and the DNA isolated by means known in the art. In certain embodiments, the means for identification of the shRNA, such as the unique identifying nucleotide sequence (or shRNA "barcodes"), may be amplified and identified by nucleic acid sequencing (e.g., next generation sequencing). A unique identifying nucleotide sequence, such as a 60-nucleotide "barcode," is described, for example, in Silva, J. M., et al., *Second-Generation shRNA Libraries Covering the Mouse and Human Genomes*, NATURE GENETICS, 37:11, 1281-88 (2005) and Westbrook, T. F., et al., A Genetic Screen for Candidate Tumor Suppressors Identifies REST, CELL, 121: 837-48 (2005). Other unique identifying nucleotide sequences may include, for example, half hairpin tags and full-length hairpin tags, such as those described in Boettcher, M. and Hoheisel, J. D., *Pooled RNAi Screens—Technical and Biological Aspects*, CURR GENOMICS, 11(3): 162-67 (2010). By using PCR amplification followed by hybridization to DNA microarrays containing complimentary probe sequences, the unique identifying nucleotide sequence may be used to identify the presence of and determine the relative frequency of specific shRNAs. In the screening methods disclosed herein, the shRNAs that are not identified following the treatment steps represent shRNAs from cells that did not survive the treatment of the suspected epigenetic compound when used in combination with the shRNA.

In certain embodiments of the disclosure, the shRNAs target specific oncogenes and inhibit expression of those oncogenes. In certain embodiments, the shRNAs target specific tumor suppressor genes and increase expression of those tumor suppressor genes. As disclosed herein, in certain embodiments when cancer cells are exposed to the epigenetic compound and an shRNA that targets a specific gene, the cancer cells do not survive. Therefore, agents that directly or indirectly reduce or increase expression of the specific gene targeted by such shRNAs (or alter expression of a polypeptide encoded by the gene by reducing or increasing expression of the polypeptide) may be selected as ISLET targets for combination therapy with the epigenetic compound.

In certain embodiments of the screening methods disclosed herein, the library of agents may comprise siRNA libraries, CRISPR-Cas9 sgRNA libraries, insertional mutagenesis libraries, or other small molecule and/or nucleic acid inhibitor molecule libraries known to those of ordinary skill in the art in lieu of shRNA libraries. For example, in certain embodiments, a CRISPR system may be used. Typically, a CRISPR system includes a Cas9 endonuclease, a CRISPR RNA (crRNA), and a transactivating RNA (tracrRNA) and may be used to create transduced cell libraries for pooled knockout screens. The crRNA and tracrRNA may be combined into single guide RNA ("sgRNA"). CRISPR stands for Clustered Regularly Interspaced Short Palindromic Repeats and is a system for genome engineering that may be used to create gene knockout pools. The crRNA contains a nucleotide sequence of approximately 20 nucleotides that may be used as the targeting sequence, as well as other nucleic acids that hybridize with the tracrRNA. This targeting sequence can be altered to suppress or activate specific genes in order to create a customized knockout pool. The tracrRNA hybridizes to the crRNA and binds to the Cas9 endonuclease activating the complex to create double-stranded breaks at specific sites within a target sequence, followed by repair of the double-stranded break after cleavage. Shalem et al., *Genome-Scale CRISPR-Cas9 Knockout Screening in Human Cells*, SCIENCE, 343; 6166, 84-87 (2014). In this way, a specific gene knockout pool may be created.

Further disclosed herein are methods for treating cancer, the methods comprising administering to a subject in need of treatment an effective amount of at least one epigenetic compound, such as DNA methyltransferase inhibitor or MBD protein inhibitor, and an effective amount of at least one chemotherapeutic agent. In certain embodiments, the at least one chemotherapeutic agent is chosen from RAR agonists, kinase inhibitors such as an Aurora kinase A inhibitor, G-protein coupled receptor inhibitors, guanine nucleotide exchange factor inhibitors, phosphatase inhibitors, sulfotransferase inhibitors, acetyltransferase inhibitors, dopachrome tautomerase inhibitors, fucosyltransferase inhibitors, steroid hormone biosynthesis inhibitors, cytokine inhibitors, phosphodiesterase inhibitors, JAK/Stat inhibitors, microtubule agents, nucleoside analogs, and antibiotics. In certain embodiments, the at least one epigenetic compound and the at least one chemotherapeutic agent target at least one pathway chosen from hypoxia pathways, apical junction pathways, DNA repair pathways, complement pathways, glycolysis pathways, coagulation pathways, fatty acid metabolism pathways, allograft rejection pathways, inflammatory response pathways, MTORC1 signaling pathways, oxidative phosphorylation pathways, and peroxisome pathways.

In certain embodiments, the DNA methyltransferase inhibitor is decitabine, and in certain embodiments, the Aurora kinase A inhibitor is alisertib. In other embodiments disclosed herein, the MBD protein inhibitor is KCC-08, and in certain embodiments the RAR agonist is isotretinoin. In certain aspects, the cancer is chosen from prostate, ovarian, lung, colon, central nervous system, and breast cancers.

As used herein, a "cancer" in an animal refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells. A cancer can include, but is not limited to, lung cancer, breast cancer, prostate cancer, central nervous system cancer, colorectal cancer, esophageal cancer, stomach cancer, leukemia/lymphoma, uterine cancer, skin cancer, endocrine cancer, urinary cancer, pancreatic cancer, gastrointestinal cancer, ovarian cancer, cervical cancer, and adenomas. In certain embodiments, the cancer is chosen from prostate cancer, ovarian cancer, lung cancer, colorectal cancer, and breast cancer.

The term "effective amount" used herein refers to an amount of a compound or composition sufficient to treat a specified disorder, condition, or disease such as ameliorate, palliate, lessen, and/or delay one or more of its symptoms. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some variations, an effective amount is an amount sufficient to prevent or delay occurrence and/or recurrence. An effective amount can be administered in one or more administrations. In the case of cancer, the effective amount of the compound or composition may: (i) reduce the number of cancer cells; (ii) reduce tumor size; (iii) inhibit, retard, slow to some extent and, in some embodiments, stop cancer cell infiltration into peripheral organs; (iv) inhibit (i.e., slow to some extent and in some embodiments stop) tumor metastasis; (v) inhibit tumor growth; (vi) prevent or delay occurrence and/or recurrence of tumor; and/or (vii) relieve to some extent one or more of the symptoms associated with the cancer.

In certain embodiments, the epigenetic compound is a histone deacetylase inhibitor or a histone methyltransferase inhibitor. Histone deacetylase inhibitors inhibit histone deacetylases, which are enzymes responsible for removing acetyl groups on a histone, allowing the DNA to wrap around the histone more tightly. Histone deacetylase inhibitors result in hyperacetylation of the histones, which thereby affects gene expression. Exemplary histone deacetylases include those acting on Class I, Class II, Class III, and Class IV histone deacetylases, such as hydroxymates, cyclic tetrapeptides, depsipeptides, benzamides, ketones, and aliphatic acid compounds such as phenylbutyrate and valproic acid. Histone deacetylase inhibitors that may be mentioned include, for example, romidepsin (Istodax®), vorinostat, and etinostat (SNDX-275, MS-275). Likewise, histone methyltransferase inhibitors also affect gene expression. By inhibiting methylation of the histone at, for example, the histone's lysine or arginine methylation sites, histone methyltransferase inhibitors work to silence, or in some cases activate, gene expression. Exemplary histone methyltransferase inhibitors include pinometostat (EPZ5676), EPZ005687, GSK343, BIX01294, tazemetostat (EPZ-6438), MI-503, MI-463, EPZ020411, MS049, UNC3866, CPI-1205, A-366, MI-136, GSK591, HLCL061 hydrochloride, UNC1999, MM-102, SGC 0946, UNC0379, EPZ015666 (GSK3235025), PFI-2, UNC0631, SGC707, MS023, MI-3 (Menin-MLL inhibitor), BRD4770, MI-2

(Menin-MLL inhibitor), E11, GSK503, EPZ004777, GSK126, CPI-360, CPI-169, AMI-1, and OICR-9429.

In certain embodiments, the histone deacetylase inhibitor is a nucleic acid inhibitor molecule that targets the gene encoding histone deacetylase. In certain embodiments, the histone methyltransferase inhibitor is a nucleic acid inhibitor molecule that targets the gene encoding histone methyltransferase. The nucleic acid inhibitor molecules include, but are not limited to, an antisense oligonucleotide or RNA interference molecules, such as microRNA, short interfering RNA, or piwi-interacting RNA.

In certain embodiments, the epigenetic compound is a MBD protein inhibitor. As used herein, a MBD protein inhibitor is a compound that can inhibit binding of methyl-CpG binding proteins. In some embodiments, the MBD protein inhibitor is an MBD2 protein inhibitor. In particular embodiments, the MBD2 protein inhibitor may be chosen from the compounds KCC-08, KCC-03, and KCC-07. KCC-08 is represented by the following Formula (I):

Formula (I)

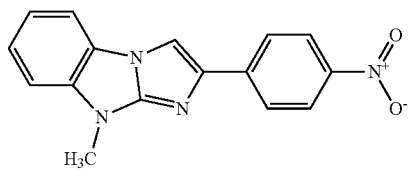

KCC-03 is represented by the following Formula (II), and KCC-07 is represented by the following Formula (III):

Formula (II)

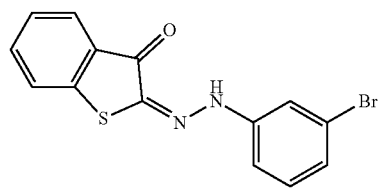

Formula (III)

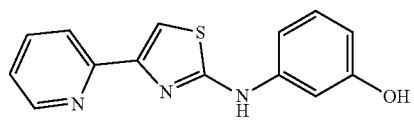

Another exemplary epigenetic compound is a DNA demethylating agent. As used herein, a DNA demethylating agent is a compound that can inhibit methylation of DNA. In some embodiments, the DNA demethylating agent is a DNA methyltransferase inhibitor. A DNA methyltransferase inhibitor is a compound that inhibits an enzyme that catalyzes the transfer of a methyl group to DNA. In particular embodiments, the DNA methyltransferase inhibitor may be chosen from 5-azacitidine (azacytidine, 4-amino-1-ß-D-ribofuranosyl-s-triazin-2(1H)-one, Vidaza®), decitabine (5-aza-2'-deoxycytidine, Dacogen®), SGI-110 (2'-deoxy-5-azacytidylyl-(3'-5')-deoxyguanosine), RG108 (N-phthalyl-L-tryptophan), DZNep (SGI-1036, 3-deazaneplanocin A), Zebularine (pyrimidin-2-one beta-ribofuranoside), disulfiram (a DNMT1 inhibitor), procainamide, and ASTX-727.

In certain embodiments, the DNA methyltransferase inhibitor is a nucleic acid inhibitor molecule that targets the gene encoding DNA methyltransferase. The nucleic acid inhibitor molecules include, but are not limited to, an antisense oligonucleotide or RNA interference molecules, such as microRNA, short interfering RNA, or piwi-interacting RNA.

Also disclosed herein are chemotherapeutic agents that may be used in combination with the epigenetic compound. In certain embodiments, the chemotherapeutic agent is used together with the epigenetic compound in an amount that is synergistic to inhibit the growth of cancer cells. Any known chemotherapeutic may be used. In certain embodiments, the chemotherapeutic agent is a nucleic acid inhibitor molecule, such as an antisense oligonucleotide or a RNA interference molecule, such as microRNA, short interfering RNA, or piwi-interacting RNA.

As used herein, a RAR agonist is an exemplary chemotherapeutic agent that can enhance target gene expression. Retinoic acid receptors can bind to corepressor proteins to inhibit gene expression; RAR agonists result in the dissociation of the corepressor proteins and in turn promote binding and recruitment of co-activator proteins, leading to downstream expression of the target gene. In particular embodiments, RAR agonists may be chosen from, for example, isotretinoin, alitretinoin, tretinoin, bexarotene, tazarotene, MDI 301, R667, 9-cis UAB30, Adapalene, AC 261066, AC 55649, AM 580, AM 80, BMS 753, CD 1530, CD 2314, CD 437, Ch 55, TTNPB, BMS 453, EC 19, EC 23, and fenretinide.

As used herein, an Aurora kinase inhibitor is another exemplary chemotherapeutic compound that can inhibit the progression of a cell through mitosis. Aurora kinase enzymes are known to play a key role in cell mitosis, including regulating functions such as centrosome maturation, chromosome alignment, chromosome segregation, and cytokinesis. Human cells contain an Aurora kinase family of enzymes that comprises Aurora kinase A, Aurora kinase B, and Aurora kinase C, each of which serve different roles during the process of mitosis. It has been discovered that Aurora kinase A, for example, may be overexpressed in certain types of cancers. Accordingly, the study of Aurora kinase A inhibitors is of interest to investigators for its potential chemotherapeutic properties. In particular embodiments, the Aurora kinase A inhibitor disclosed herein may be chosen from alisertib (MLN8237), AMG-900, barasertib, CYC116, danusertib (PHA-739358) MLN8054, VX-680 (MK-0457, tozasertib), and TAS-119.

In certain embodiments, the chemotherapeutic agent is a compound that is chosen because it inhibits a gene that is or is believed to be associated with cancer. In certain embodiments disclosed herein, the chemotherapeutic agent is a compound that inhibits at least one of the following genes: PLAS2G12A, EIF4A2, GNAZ, DCT, SULT1C4, HLX, ITK, AURKA, CHST3, MAP2K2, AADAT, CRAT, SULT4A1, PDE4D, THY1, PDE1B, BDH2, QPRT, STAT5A, PHF21A, MEF2C, IL17D, SEL1L, COMT, GLRX, AKR1C4, GNA12, B4GALT1, LEF1, XYLT1, GNAQ, GCA, AGXT2, DPM2, OGDHL, UGT2B10, PDESA, GPSM1, LIG3, PDE4B, LCMT1, DHX58, GBGT1, DUSP9, DCI, B4GALT2, MTR, NT5C2, HSD3B2, ARL4D, GPT2, OAT, RFXAP, PDE11A, BCR, GNA11, PDE4C, DHRS3, FOXN1, PDE6G, G6PC2, RPIA, IDI1, ACSS1, FHIT, UGT1A3, FARS2, A4GALT, GATM, CHST1, AGPAT4, NTSM, MVK, UGT2B17, ARHGEF1, NEURL, QPCT, GNAI3, ATIC, PLA2G12A, DARS, AKRIC1, B4GALT5, FUT5, COX10, AKAP13, AGXT, GNMT, HOXB4, CAND1, CLC, TFAP2A, HMGN1, RAD9A, GNB3, ECGF1, ARPC3, ACVR1B, CKS1B, SLC1A2, UROS, CHST4, NTSE, PIGL, CIGALT1, PDE1A, ACP6, NOS1, RECQL4, NOS3, RNF2, LSS, ANP32A, RAG2, BCL2L2, CPE, CAPN9, PRKAR2A, EP300, FGFR2, ISYNA1, ARF3, IPMK, BCL11B, HMGCS1, GALNT14, GALNS, FAH, AK3L1, SULT1C2, GLP1R, AGPAT2, and FOXP1.

In some embodiments, the epigenetic compound or chemotherapeutic agent may be inactive until converted to the active form in vivo in a subject. For example, inactive versions of decitabine, such as SGI-110 (Astex®), are within the scope of the present disclosure as they may be converted to decitabine in vivo.

In some embodiments, the methylated-DNA binding protein inhibitor is KCC-08 and the dosage administered in a single administration over a 24-hour period may be less than about 25 mg/kg, such as less than about 20 mg/kg, less than about 10 mg/kg, less than about 5 mg/kg, or less than about 2 mg/kg, or about 1 mg/kg. In certain embodiments, the KCC-08 may be administered over the course of multiple consecutive days, such as, for example, administered once a day for 2-7 days, such as once a day for 5 days. KCC-08 may also be administered in multiple cycles (e.g., 2, 3, 4, or more than 4 cycles), typically with 0-6 weeks between each cycle, such as, for example, administered every 5 days over a 3-week cycle or over a 4-week cycle. In certain embodiments, the KCC-08 may be administered in an amount of about 1 mg/kg/day every 5 days during a 4-week cycle.

In some embodiments, the DNA methyltransferase inhibitor is decitabine and the dosage administered in a single administration over a 24-hour period may be less than about 25 mg/m$^2$, such as less than about 20 mg/m$^2$, less than about 10 mg/m$^2$, less than about 5 mg/m$^2$, or less than about 3.5 mg/m$^2$. In certain embodiments, when the decitabine is administered more than once over a 24-hour period, the dosage administered over the 24-hour period may be less than 150 mg/m$^2$, such as less than about 125 mg/m$^2$, less than about 100 mg/m$^2$, less than about 40 mg/m$^2$, less than about 35 mg/m$^2$, less than about 30 mg/m$^2$, less than about 25 mg/m$^2$, less than about 20 mg/m$^2$, or less than about 15 mg/m$^2$. In certain embodiments, the decitabine may be administered over the course of multiple consecutive days, such as, for example, administered once a day for 2-7 days, such as once a day for 5 days. Decitabine may also be administered in multiple cycles (e.g., 2, 3, 4, or more than 4 cycles), typically with 4-6 weeks between each cycle, such as, for example, administered every 5 days over a 4-week cycle. In certain embodiments, the decitabine may be administered in an amount of about 20 mg/m$^2$ every 5 days during a 4-week cycle. In certain embodiments, the decitabine may be administered in an amount of about 5 mg/m$^2$ or less every 5 days during a 4-week cycle, and in certain other embodiments, the decitabine may be administered in an amount of about 3.5 mg/m$^2$ or less every 5 days during a 4-week cycle. In other embodiments, the dosage concentration may range from about 1 nM to about 500 nM, such as about 10 nM to about 250 nM, or about 100 nM.

In some embodiments, the RAR agonist is isotretinoin and the dosage concentration may range from about 5 mg/kg to about 150 mg/kg per dosage, such as about 90 mg/kg, 60 mg/kg, about 30 mg/kg, about 15 mg/kg, and 10 mg/kg per dosage. In certain embodiments, the RAR agonist may be administered once or twice a day, such as, for example, 15 mg/kg administered twice a day or about 30 mg/kg administered once a day. In certain embodiments, the dosage may be less than about 60 mg/kg per dosage. In certain embodiments, when the RAR agonist is administered in a cycle, the dosage administered during the entirety of the cycle may range from about 30 mg/kg to about 300 mg/kg, such as about 90 mg/kg to about 250 mg/kg, or about 150 mg/kg. In certain embodiments, the dosage administered during the entirety of the cycle may be less than about 200 mg/kg.

In some embodiments, the Aurora kinase A inhibitor is alisertib and the dosage concentration may range from about 5 nM to about 150 nM, such as about 10 nM, about 50, or about 100 nM. In certain embodiments, the dosage concentration may range from about 10 mg/kg to about 30 mg/kg, such as about 15 mg/kg or about 25 mg/kg. In certain embodiments, the dosage administered may range from about 25 mg to about 75 mg per dosage, such as about 10 mg, 30 mg, about 35 mg, about 40 mg, and 50 mg per dosage. In certain embodiments, the Aurora kinase A inhibitor may be administered once or twice a day, such as, for example, 30 mg administered twice a day or 50 mg administered twice a day. In certain embodiments, the dosage may be less than about 50 mg per dosage. In certain embodiments, when the Aurora kinase A inhibitor is administered in a cycle, the dosage administered during the entirety of the cycle may range from about 70 mg to about 1050 mg, such as about 350 mg to about 700 mg, about 1050 mg, or about 700 mg. In certain embodiments, the dosage administered during the entirety of the cycle may be less than about 700 mg.

In certain embodiments, the at least one epigenetic compound, such as a DNA demethylating agent or methylated-DNA binding protein inhibitor, may be administered sequentially to the at least one chemotherapeutic agent, such as Aurora kinase A inhibitor or RAR agonist, and in certain embodiments it may be administered simultaneously with the at least one chemotherapeutic agent. The term "sequential administration" as used herein means that the at least one epigenetic compound and the at least one chemotherapeutic agent are administered with a time separation of more than about one day. In certain embodiments, when the at least one epigenetic agent is administered sequentially, it may be administered prior to or after the administration of the at least one chemotherapeutic agent, and in certain embodiments administration may overlap such that it is both sequential and simultaneous (e.g., the at least one epigenetic compound is administered first for a period of time, followed by the at least one chemotherapeutic agent administered alone, followed by simultaneous administration of both the at least one epigenetic compound and the at least one chemotherapeutic agent). In some embodiments, the at least one epigenetic compound may be administered for a period of days such as about 1 day to about 12 days, or for a period of weeks, such as about 1 week to about 10 weeks, or may be administered in a cycle, such as about every 5 to about every 7 days in a 28-day cycle.

The term "simultaneous administration," as used herein, means that the compounds are administered with a time separation of no more than about 1 day, such as no more than about 12 hours, no more than about 6 hours, or no more than about 1 hour. In certain embodiments of simultaneous administration, the compounds are administered with a time separation of no more than about 15 minutes, such as no more than about 10 minutes, no more than about 5 minutes, or no more than about 1 minute. When the compounds are administered simultaneously, they may be contained in the same composition (e.g., a pharmaceutical composition comprising both an epigenetic compound and a chemotherapeutic agent) or in separate compositions (e.g., the at least one epigenetic compound is contained in one composition and the at least one chemotherapeutic agent is contained in another composition).

In certain embodiments disclosed herein, the administration of the at least one epigenetic compound and the at least one chemotherapeutic agent are concurrent, i.e., the administration period of the at least one epigenetic compound and the at least one chemotherapeutic agent overlap with each other. In some embodiments, the administration of the at least one epigenetic compound and the at least one chemotherapeutic agent are non-concurrent. For example, in some embodiments, the administration of the at least one epigenetic compound is terminated before the at least one chemotherapeutic agent is administered. In some embodiments, the administration of the at least one chemotherapeutic agent is terminated before the at least one epigenetic compound is administered. In certain embodiments, time period between these two non-concurrent administrations can range from about one day to about eight weeks, such as about two weeks or about four weeks.

Treatment according to the methods disclosed herein can results in complete relief or cure from the cancer, or partial amelioration of one or more symptoms of the cancer, and can be temporary or permanent. In certain embodiments, in the methods disclosed herein the administration of an effective amount of at least one epigenetic compound and an effective amount of at least one chemotherapeutic agent, such as decitabine and an Aurora kinase A inhibitor or an MBD protein inhibitor and a RAR agonist, may result a in decrease in the cancer in a subject of at least about 10%, at least about 20%, at least about 30%, at least about 40%, at least about 50%, at least about 60%, at least about 70%, at least about 80%, at least about 90%, at least about 100%, and a 100% decrease in the cancer in a subject.

In some embodiments, the effect of the at least one epigenetic compound, such as DNA methyltransferase inhibitor or MBD protein inhibitor, and the at least one chemotherapeutic agent, such as Aurora kinase A inhibitor or RAR agonist, is synergistic. As used herein, the terms "synergy," "synergistically," and derivations thereof, indicate that the biological activity of the combination of the at least one epigenetic compound and the at least one chemotherapeutic agent is greater than the sum of the biological activities of the respective agents when administered individually. The synergy may occur when the respective agents are administered at the same time or if one of the agents is administered before the other. In some embodiments, the at least one epigenetic compound and the at least one chemotherapeutic agent have minimal tumor growth inhibitory activity when administered to a patient separately; however, the same dosages of the at least one epigenetic compound and the at least one chemotherapeutic agent, when administered to a patient in combination, may have a high tumor growth inhibitory activity. This synergy of the at least one epigenetic compound and at least one chemotherapeutic agent is surprising and unexpected.

Synergy may be measured by various methods, including, for example, the Bliss synergy method. See Bliss, C. I., *The Toxicity of Poisons Applied Jointly*, ANN. APPL. BIO. 26:3 585-615 (1939). The Bliss value may be defined as the difference between the experimental response and the calculated Bliss Independence value. The Bliss value indicates whether the effect of two compounds in combination is merely additive or is synergistic. A Bliss value of zero is considered additive, wherein the term "additive" means that the result of the combination of the two compounds is the sum of each compound individually, and the compounds are not considered synergistic. A negative Bliss value indicates antagonism, wherein one of the compounds acts to inhibit the effect of the other. A positive Bliss value indicates synergy, wherein the combined effect of the two compounds is greater than their sum. The higher the positive Bliss value, the greater the synergy of the two compounds.

In certain embodiments disclosed herein, the at least one epigenetic compound and the at least one chemotherapeutic agent have a Bliss synergy value on cancerous cells of greater than about 0, such as greater than about 0.1, greater about 0.25, greater than about 0.4, greater than about 0.5, or greater than about 0.7.

In one embodiment disclosed herein, the synergy of the at least one epigenetic compound, such as a DNA methyltransferase inhibitor such as decitabine, and the at least one chemotherapeutic agent, such as an Aurora kinase A inhibitor such as alisertib, is such that the doses administered of the epigenetic compound and/or the chemotherapeutic agent to achieve a therapeutically effective amount may be lower than what is normally required when each agent is administered alone. In certain embodiments, the synergy of the MBD protein inhibitor such as KCC-08, and the at least one chemotherapeutic agent, such as a RAR agonist such as isotretinoin, is such that the doses administered of the MBD protein inhibitor and/or the chemotherapeutic agent to achieve a therapeutically effective amount may be lower than what is normally required when each agent is administered alone. Thus, in some embodiments, a subtherapeutic amount of the at least one epigenetic compound and/or the at least one chemotherapeutic agent may be administered. "Subtherapeutic amount" or "subtherapeutic level" refer to an amount that is less than the therapeutic amount, that is, less than the amount normally used when the compound is administered alone for chemotherapeutic or epigenetic purposes. The reduction may be reflected in terms of a reduced amount of administration and/or a reduced frequency of administration.

Administration to a subject for therapy can occur by any suitable route of administration, including, for example, orally, nasally, transmucosally, ocularly, rectally, intravaginally, parentally, including intramuscularly, subcutaneously, intramedullary injections, as well as intrathecal, direct intraventricular, intravenous, intra-articular, intra-sternal, intrasynovial, intra-hepatic, intralesional, intracranial, intraperitoneal, intranasal, or intraocular injections, intracisternally, topically, as by powders, ointments, or drops (including eye drops), including buccally and sublingually, transdermally, through an inhalation spray, or other modes of delivery known in the art.

Also disclosed herein are pharmaceutically acceptable compositions for treating cancer comprising an effective amount of at least one epigenetic compound, such as a DNA methyl transferase inhibitor or an MBD protein inhibitor, and an effective amount of at least one chemotherapeutic agent, such as an Aurora kinase A inhibitor or a RAR agonist, wherein the at least one epigenetic compound and the at least one chemotherapeutic compound synergistically inhibit growth of cancer cells. The pharmaceutically acceptable composition that comprises the combinations disclosed herein may be admixed with any pharmaceutically acceptable carrier, such as a non-toxic pharmaceutical organic or inorganic carrier, in order to provide a pharmaceutically acceptable composition. Typical pharmaceutically acceptable carriers include, for example, mannitol, urea, dextrans, lactose, potato starches, maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid, and other conventionally employed acceptable carriers. The pharmaceutical dosage form can also contain non-toxic auxiliary substances such as emulsifying agents, preserving agents, wetting agents, and the like.

Further disclosed herein are kits for the treatment of cancer, wherein the kits comprise an effective amount of at least one epigenetic compound, such as a DNA methyl transferase inhibitor or an MBD protein inhibitor, and an effective amount of at least one chemotherapeutic agent, such as an Aurora kinase A inhibitor or a RAR agonist, and wherein the at least one epigenetic agent and the at least one chemotherapeutic agent synergistically inhibit growth of cancer cells. In certain embodiments the at least one epigenetic compound in the kit may be decitabine, and in certain embodiments, the at least one chemotherapeutic agent in the kit may be alisertib. In certain embodiments the at least one epigenetic compound in the kit may be KCC-08, and in certain embodiments, the at least one chemotherapeutic agent in the kit may be isotretinoin. In further embodiments, the kit may comprise instructions for administration or formulation of the compounds.

The dosing frequency of the at least one epigenetic compound and the at least one chemotherapeutic agent may be adjusted over the course of treatment, based on the judgment of the administrator. When administrated separately, the at least one epigenetic compound and the at least one chemotherapeutic agent can be administered at different frequencies and/or intervals. The at least one epigenetic compound and the at least one chemotherapeutic agent can be administered using the same route of administration or different routes of administration.

In certain embodiments disclosed herein, a combination of at least one epigenetic compound and at least one chemotherapeutic agent, wherein the combination is effective to synergistically inhibit cancer cell growth, does not synergistically inhibit noncancerous cell growth, such that the effect is merely additive or less than additive on noncancerous cells. In certain embodiments, the noncancerous cells are primary hepatocytes. In certain embodiments of the disclosure, a combination of a DNA methyltransferase inhibitor, such as decitabine, and an Aurora kinase A inhibitor, such as alisertib, does not synergistically inhibit noncancerous cell growth, such that the effect is merely additive or less than additive on noncancerous cells, and in certain embodiments, a combination of an MBD protein inhibitor, such as KCC-08, and a RAR agonist, such as isotretinoin, does not synergistically inhibit noncancerous cell growth, such that the effect is merely additive or less than additive on noncancerous cells. In certain embodiments disclosed herein, the at least one epigenetic compound and the at least one chemotherapeutic agent have a Bliss synergy value on noncancerous cells of 0 or less than about 0, such as about −0.05 or about −0.10.

In certain embodiments disclosed herein, the at least one epigenetic compound, such as DNA methyltransferase inhibitor or MBD protein inhibitor, is heritable, such that it induces an epigenetic memory that persists and sensitizes at least one targeted agent, such as an Aurora kinase A inhibitor or a RAR agonist, even after removal of the initial epigenetic compound. This allows for the possibility of sequential therapy that may further minimize unwanted toxicity. Accordingly, in another embodiment, disclosed herein is a method for sensitizing a cell to a chemotherapeutic agent, such as Aurora kinase A inhibitor or a RAR agonist, the method comprising contacting the cell with an effective amount of a low dose of an epigenetic compound prior to contacting the cell with an effective amount of the chemotherapeutic agent. In certain embodiments, the low dose of the epigenetic compound may be about 100 nM of a DNA methyltransferase inhibitor, such as decitabine. In certain embodiments, the low dose of the epigenetic compound may be about 1 mg/kg/day of an MBD protein inhibitor, such as KCC-08. In certain embodiments, the chemotherapeutic agent to which the cell is sensitized is an Aurora kinase A inhibitor such as alisertib, and in certain embodiments, the chemotherapeutic agent to which the cell is sensitized is a RAR agonist such as isotretinoin.

EXAMPLES

Example 1—Identification of Aurora Kinase A

A pooled lentiviral shRNA negative functional screen was carried out on a sample of DU145 prostate cancer cells, adapted from the procedure previously described in Schlabach M. R. et al., *Cancer Proliferation Gene Discovery through Functional Genomics*, SCIENCE, 319, 5863:620-4 (2008). DU145 prostate cancer cells were first treated with pooled lentiviral shRNA, resulting in the transduction of the RNA library. The lentiviral-transduced DU145 cells were then treated with decitabine, which is lethal to only a selective number of the transduced cells (i.e., the shRNA "dropouts" or "hits"). Accordingly, targets were identified that, when knocked down, were selectively lethal in DU145 cells when treated with the DNA methyltransferase inhibitor (DNMTi) decitabine relative to control treated cells.

Flasks of DU145 cells were transduced with a genome-scale pooled lentiviral shRNA library from Cellecta® (the Decipher Collection). Each lentivirus in the pool encoded each of 27,000 shRNA constructs, shRNA specific barcodes, a puromycin resistance gene, and a fluorescence marker gene to track transduction levels. Each of 5,000 human genes were targeted by 5 to 6 shRNA encoding lentiviruses in the pool, and transduction was carried out at a low multiplicity of infection (MOI of approximately 0.3), in order to ensure that the majority of transduced cells would only receive a single lentiviral particle. Enough viruses and cells were transduced such that under this low MOI, each shRNA would be represented about 100 to about 1000 times in the population.

Figure 1A:
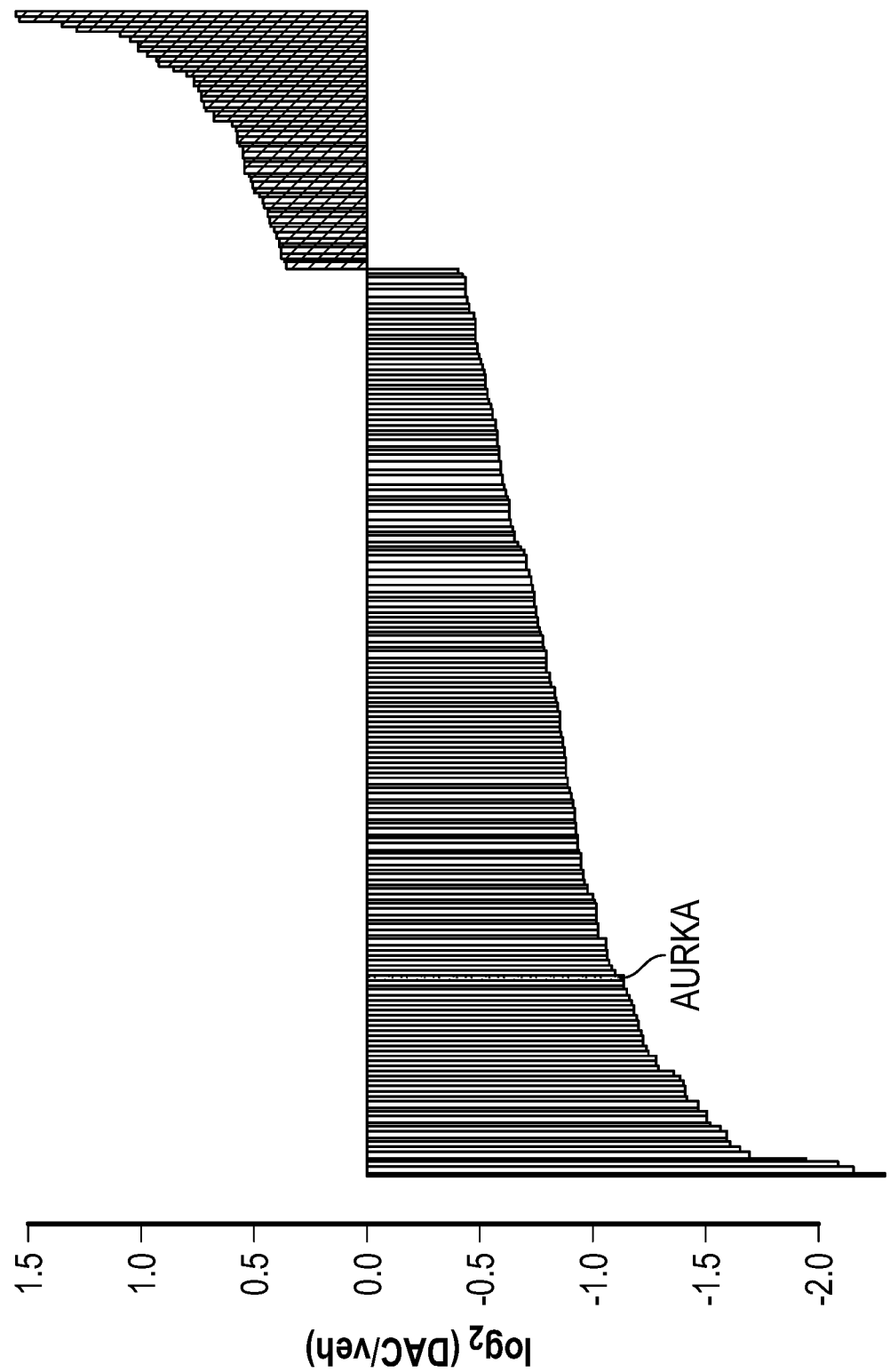
FIG. 1A is a waterfall plot of altered shRNA barcodes in the population of decitabine-treated vs. control cells, wherein bars falling below 0.0 on the x-axis [$\log_2$(decitabine/control)] indicate shRNAs sensitizing to decitabine, and bars falling above 0.0 on the x-axis indicate shRNAs resistant to decitabine.

The library of transduced cells was then treated with decitabine (100 nM or 500 nM) or vehicle control, for 4 days or 7 days, all in 2 to 3 replicate experiments. After treatments, cells were harvested, DNA isolated, and 50 μg of genomic DNA was used to amplify the shRNA specific barcodes in surviving cells. These barcodes were then identified by next generation sequencing, and the number of each barcode corresponding to an individual shRNA in the population was used as the measure of the representation of that shRNA in the vehicle and decitabine treated cells. "Hits" were identified as those shRNAs that "dropped out" in the population of decitabine treated cells compared to the population of vehicle treated cells. Conversely, shRNAs that were enriched in the population of decitabine treated cells compared to the population of vehicle treated cells were considered to confer resistance to decitabine treatment. FIG. 1A shows a waterfall plot of all significantly altered shRNA barcodes in the population of decitabine-treated vs. control cells, with bars falling below 0.0 on the x-axis indicating shRNAs that sensitized to decitabine, and bars falling above 0.0 on the x-axis indicating shRNAs that conferred resistance to decitabine.

Figure 1B:
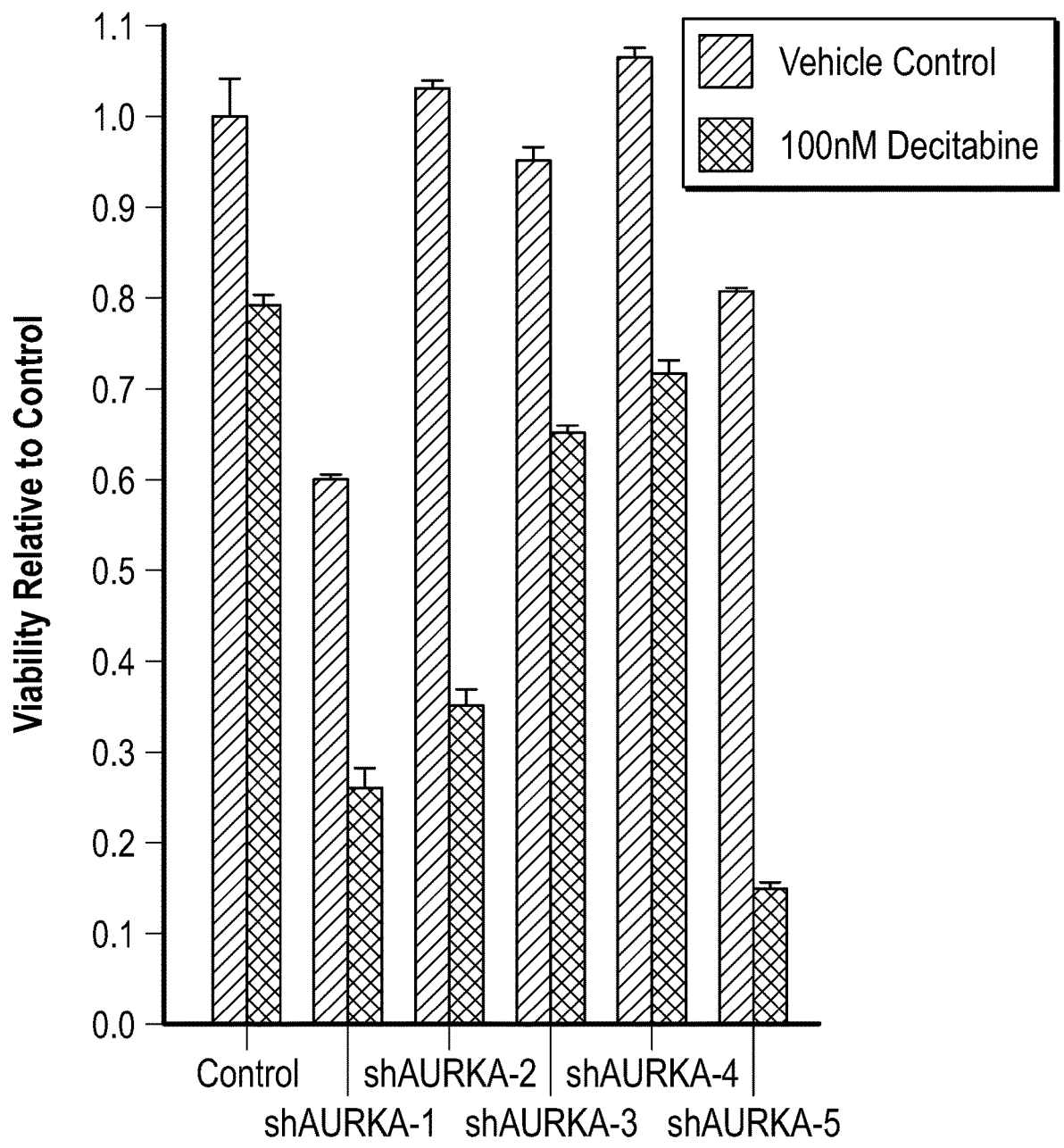
FIG. 1B is a bar graph illustrating five samples comprising DU145 cells with shRNA targeting AURKA in combination with 100 nM decitabine compared to DU145 cells with the vehicle control and with decitabine but without AURKA.

Among the top sensitizing hits, shRNA targeting the Aurora kinase A (AURKA) gene, which had a $\log_2$(DAC/veh) value of −1.13, was the top hit for which pharmacological agents are already under clinical development. FIG. 1B shows independent validation of AURKA as an Induced Synthetic Lethality with Epigenetic Therapy (ISLET) target in combination with decitabine. Five different shRNAs targeting AURKA in combination with 100 nM decitabine each caused significantly decreased DU145 cancer cell viability compared to the AURKA shRNAs alone or decitabine alone. Thus, AURKA was selected as an ISLET target for rapid translation. As shown in FIG. 1B, the overall viability of DU145 cells was markedly higher for the vehicle control with decitabine but without AURKA than for any of the five samples comprising DU145 with shRNA targeting AURKA together with decitabine.

Example 2—Synergistic Growth Inhibition Effect of DNMTi and AURKA on Cancer Cells Pharmacological inhibitors of Aurora kinases in combination with decitabine were tested. Both AURKA selective (e.g., alisertib and MLN8054) and non-selective (e.g., AMG-900) Aurora kinase inhibitors showed synergistic growth inhibition of DU-145 cells, and alisertib, the furthest along in clinical development, was selected for additional study. Alisertib and decitabine showed significant synergy in cell viability, cell growth, and clonogenic survival assays in a wide array of cancer cell lines in vitro.

Figure 2A:
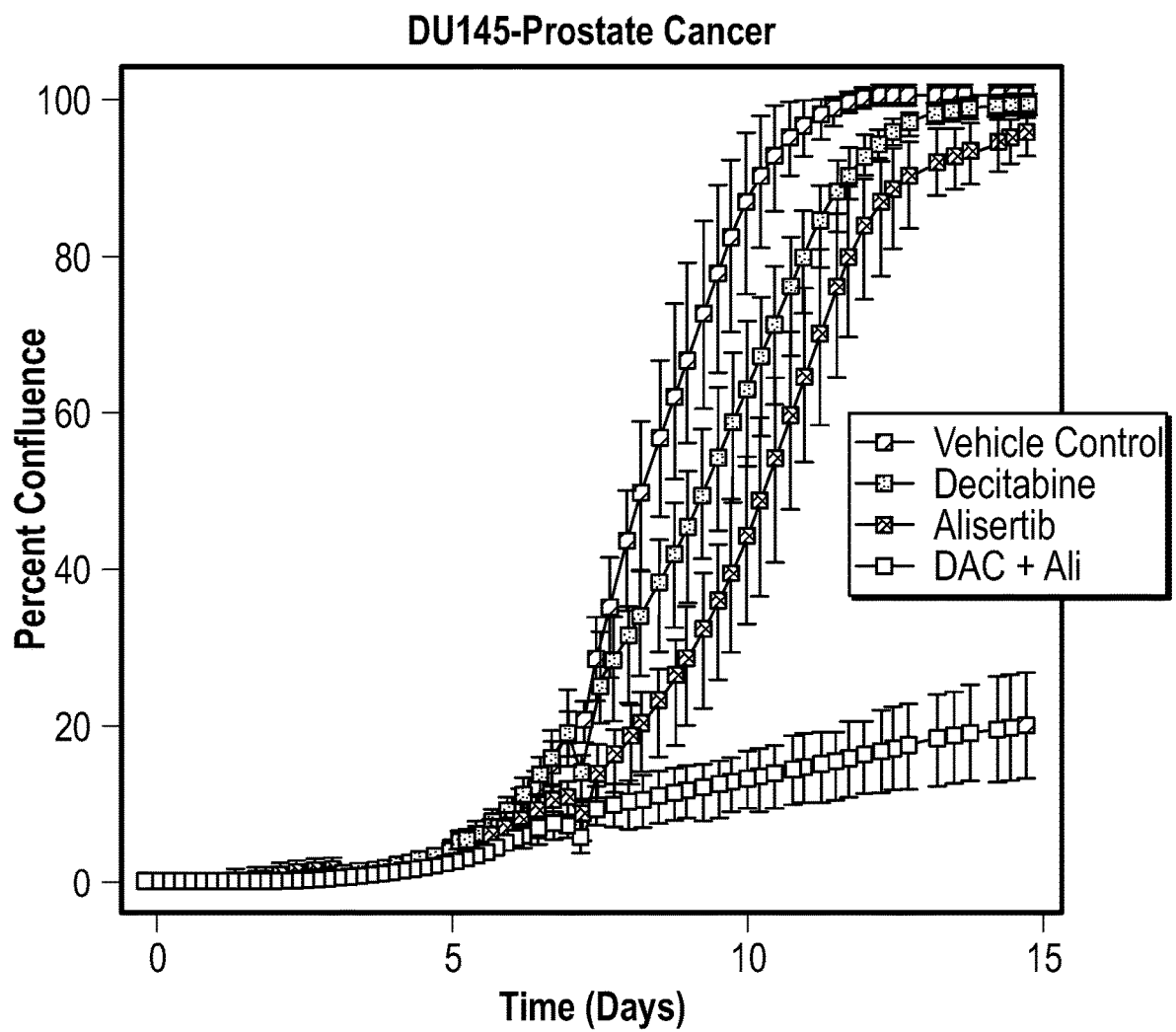
FIG. 2A is a graph showing the growth curve of the DU145 prostate cancer cells for decitabine and alisertib separately, a vehicle control, and decitabine and alisertib together.
Figure 2B:
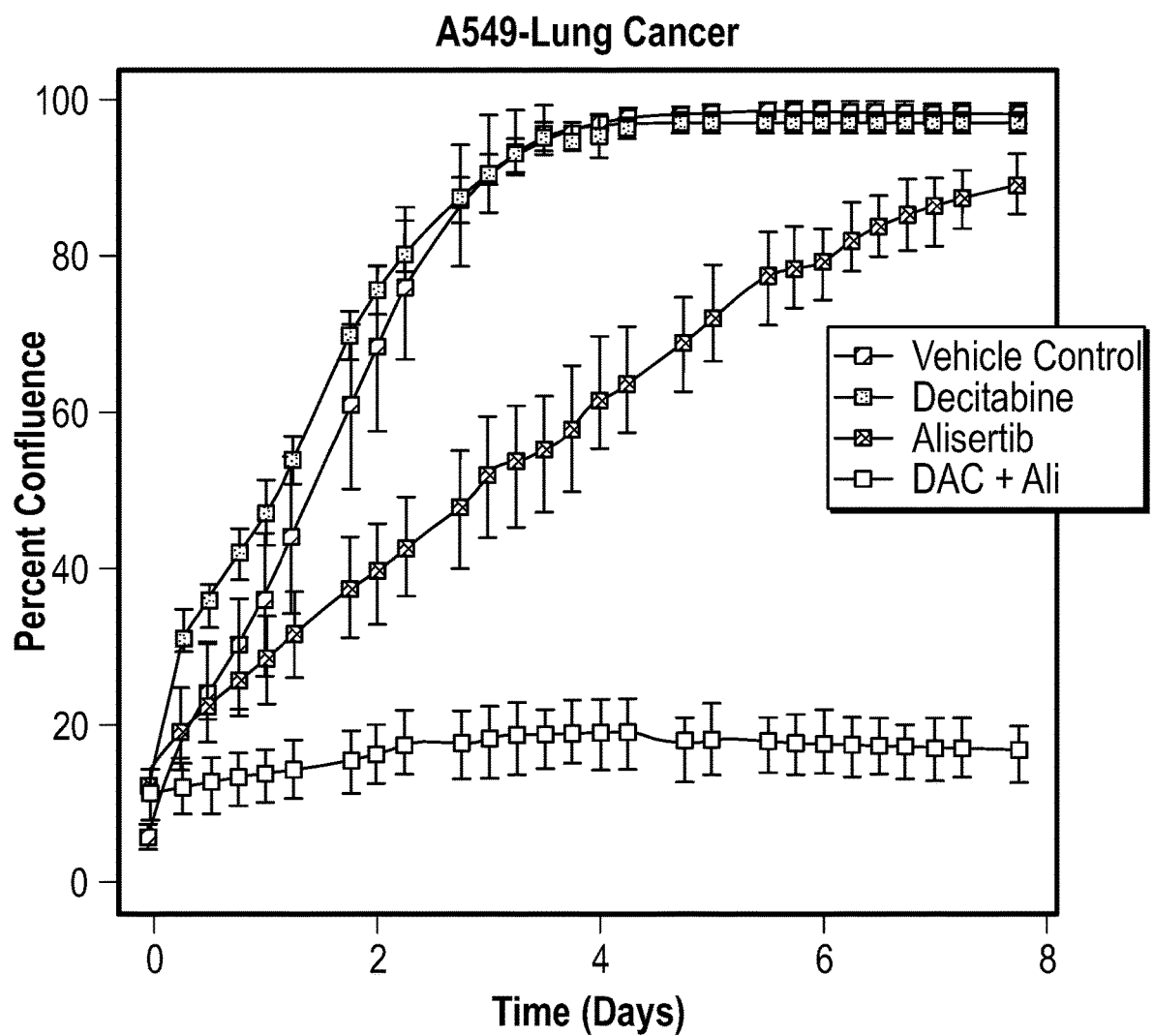
FIG. 2B is a graph showing the growth curve of the A549 lung cancer cells for decitabine and alisertib separately, a vehicle control, and decitabine and alisertib together.

DU145 prostate cancer cells and A549 lung cancer cells were treated with varying concentrations (0 nM, 10 nM, 50 nM, and 100 nM) of alisertib in addition to varying concentrations of decitabine (0 nM, 50 nM, 100 nM, and 250 nM). Representative data are shown in FIGS. 2A and 2B, as well as the Tables below. Table 1 below shows the percent growth inhibition for the DU145 prostate cancer cells with the varying amounts of alisertib together with varying amounts of decitabine. As shown in Table 1, 100 nM of alisertib and 250 nM of decitabine exhibited the greatest percent growth inhibition (0.93).

TABLE 1

Percent Growth Inhibition of DU145 Prostate Cancer Cells

| Conc. of DAC [nM] | Conc. of Alisertib [nM] | | | |
|---|---|---|---|---|
| | 0 nM | 10 nM | 50 nM | 100 nM |
| 0 nM | 0 | 0 | 0 | 0.02 |
| 50 nM | 0.04 | 0.14 | 0.42 | 0.64 |
| 100 nM | 0.08 | 0.11 | 0.33 | 0.82 |
| 250 nM | 0.77 | 0.80 | 0.90 | 0.93 |

Table 2 below shows the Bliss synergy values for varying amounts of alisertib together with varying amounts of decitabine in DU145 prostate cancer cells. As shown in Table 2, the highest Bliss synergy value (0.72) was observed with 100 nM of alisertib in combination with 100 nM of decitabine. In each panel, a dose response of each drug alone and in combination was used in Alamar blue cell viability assays.

TABLE 2

Bliss Synergy Values of DU145 Prostate Cancer Cells

| Conc. of DAC [nM] | Conc. of Alisertib [nM] | | |
|---|---|---|---|
| | 10 nM | 50 nM | 100 nM |
| 50 nM | 0.09 | 0.38 | 0.58 |
| 100 nM | 0.03 | 0.24 | 0.72 |
| 250 nM | 0.04 | 0.13 | 0.16 |

Likewise, Table 3 shows the percent growth inhibition and Table 4 shows the Bliss synergy values for varying amounts of alisertib together with varying amounts of decitabine in A549 lung cancer cells. As shown in Table 4, the highest Bliss synergy value (0.68) was observed with 100 nM of alisertib in combination with 250 nM of decitabine.

TABLE 3

Percent Growth Inhibition of A549 Lung Cancer Cells

| Conc. of DAC [nM] | Conc. of Alisertib [nM] | | | |
|---|---|---|---|---|
| | 0 nM | 10 nM | 50 nM | 100 nM |
| 0 nM | 0 | 0 | 0 | 0.01 |
| 50 nM | 0.03 | 0.03 | 0.07 | 0.30 |
| 100 nM | 0 | 0 | 0.15 | 0.52 |
| 250 nM | 0.14 | 0.46 | 0.67 | 0.83 |

TABLE 4

Bliss Synergy Values of A549 Lung Cancer Cells

| Conc. of DAC [nM] | Conc. of Alisertib [nM] | | |
|---|---|---|---|
| | 10 nM | 50 nM | 100 nM |
| 50 nM | 0 | 0.04 | 0.26 |
| 100 nM | 0 | 0.15 | 0.51 |
| 250 nM | 0.32 | 0.53 | 0.68 |

While each drug alone, at the doses tested, had minimal effect on cell viability in the DU-145 and A549 cancer cell lines, the two drugs combined showed significant reduction of cell viability. Formal synergy analyses were performed using the Bliss independence score (where values greater than zero indicate greater than additive effect).

For the doses of each agent showing the greatest synergy (i.e., 100 nM alisertib and 100 nM decitabine for DU145 and 100 nM alisertib and 250 nM decitabine for A549), growth curves are also shown in the graphs of FIGS. 2A and 2B. The graph of FIG. 2A is a growth curve of the DU145 prostate cancer cells for the agents alone (decitabine and alisertib separately), a vehicle control, and the agents in combination (decitabine and alisertib together). As shown in FIG. 2A, the combination of decitabine and alisertib together acted synergistically to inhibit cell growth of DU145 cells. Likewise, the graph of FIG. 2B is a growth curve of the A549 lung cancer cells for the agents alone (decitabine and alisertib separately), a vehicle control, and the agents in combination (decitabine and alisertib together). As shown in FIG. 2B, the combination of decitabine and alisertib together acted synergistically to inhibit cell growth of A549 lung cancer cells.

Interestingly, although the combination of decitabine and alisertib showed significant synergy for growth inhibition of multiple cancer cell lines, the combination did not significantly alter the growth of primary hepatocytes, with formal synergy analysis showing a less than additive effect. As shown in Table 5 below, both alisertib and decitabine, acting alone, have some degree of growth inhibition on primary hepatocytes. One would therefore expect at least an additive effect; however, as shown in Table 6 below, the formal synergy analysis indicated the combined effect of decitabine and alisertib on hepatocytes had a less than additive effect (i.e., negative Bliss synergy values).

TABLE 5

Percent Growth Inhibition of Primary Hepatocyte Cells

| Conc. of DAC [nM] | Conc. of Alisertib [nM] | | | |
| --- | --- | --- | --- | --- |
| | 0 nM | 10 nM | 50 nM | 100 nM |
| 0 nM | 0 | 0.1 | 0.21 | 0.15 |
| 50 nM | 0.16 | 0.20 | 0.28 | 0.28 |
| 100 nM | 0.30 | 0.24 | 0.27 | 0.29 |
| 250 nM | 0.29 | 0.33 | 0.31 | 0.34 |

TABLE 6

Bliss Synergy Values of Primary Hepatocyte Cells

| Conc. of DAC [nM] | Conc. of Alisertib [nM] | | |
| --- | --- | --- | --- |
| | 10 nM | 50 nM | 100 nM |
| 50 nM | −0.05 | −0.06 | −0.01 |
| 100 nM | −0.13 | −0.17 | −0.11 |
| 250 nM | −0.03 | −0.13 | −0.06 |

Figure 2C:
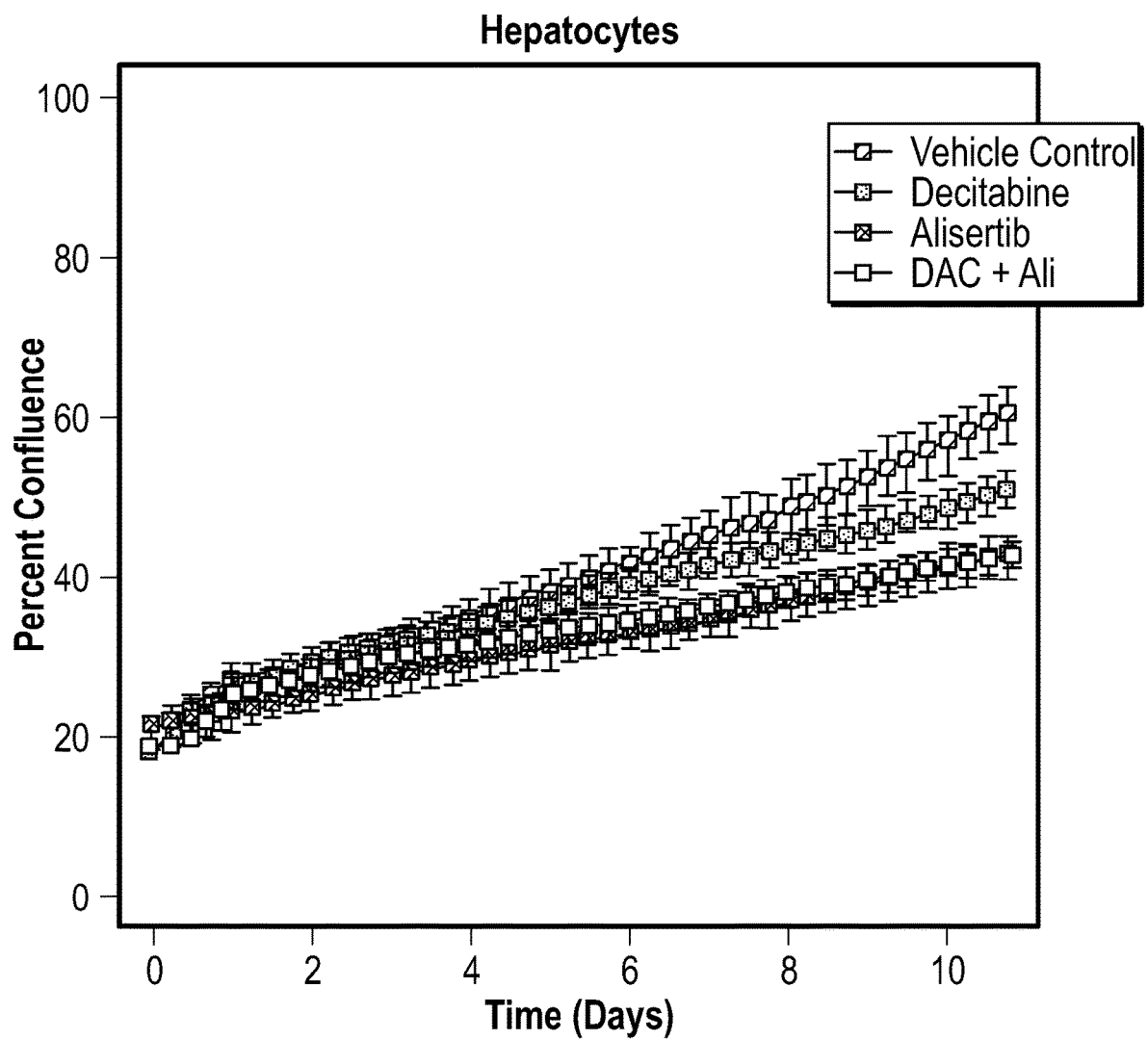
FIG. 2C is a graph showing the growth curve of hepatocyte cells for decitabine and alisertib separately, a vehicle control, and decitabine and alisertib together.

The graph of FIG. 2C is a growth curve of the hepatocyte cells for the agents alone (decitabine and alisertib separately), a vehicle control, and the agents in combination (decitabine and alisertib together). As shown in FIG. 2C, the combination of decitabine and alisertib together did not significantly affect cell growth over time.

Figure 3:
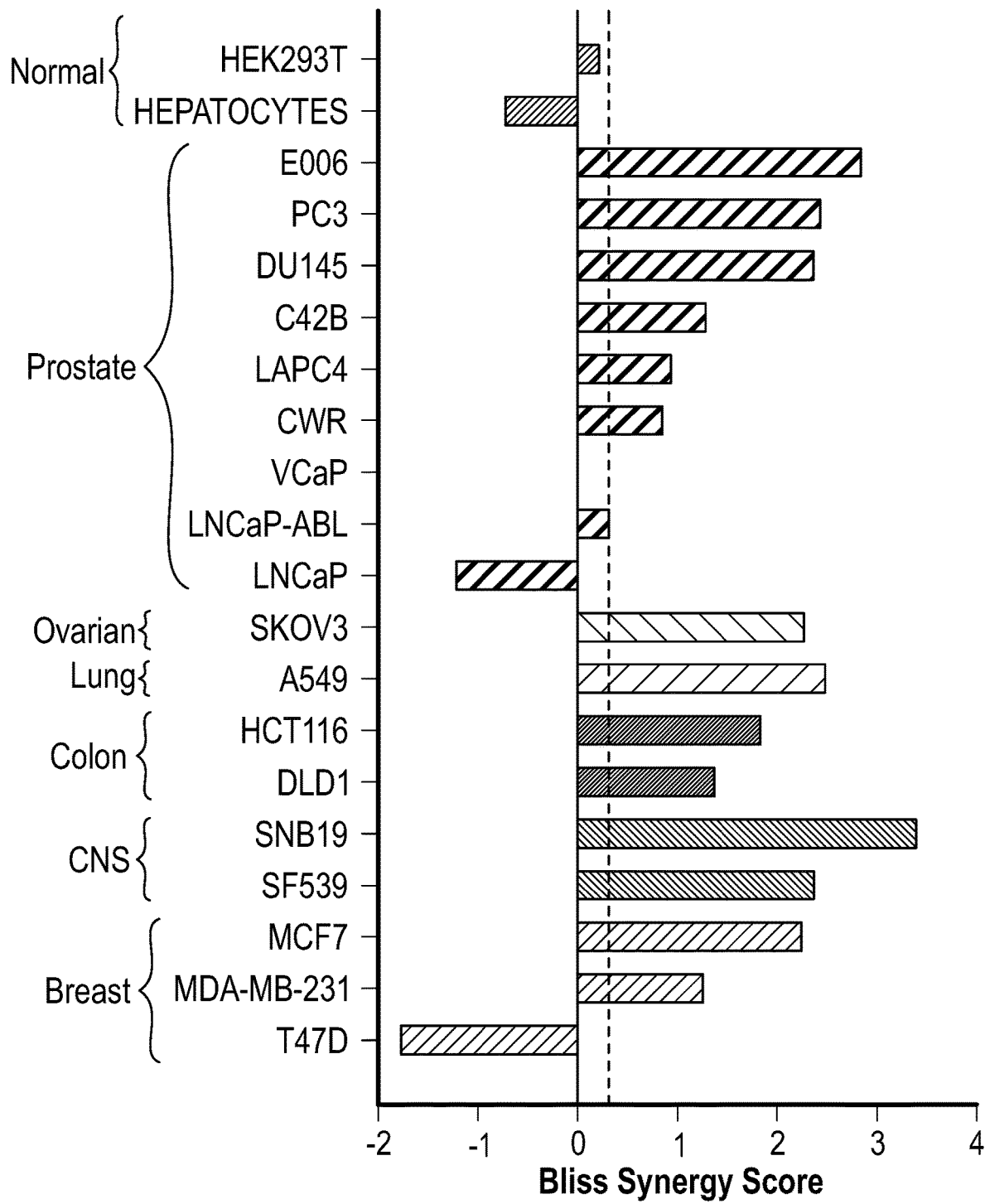
FIG. 3 is a bar graph illustrating Bliss synergy scores for the combined treatment of decitabine and alisertib on 18 cancer cells lines.

The synergy analysis of the combination of decitabine and alisertib was evaluated in a series of 18 cancer cell lines (9 prostate, 1 ovarian, 1 lung, 2 colon, 2 central nervous system, and 3 breast cancer cell lines) and 2 non-cancer cell models. A final cumulative Bliss synergy score was calculated based on the sum of the synergy values from each of the 16 combinations of 0 nM, 10 nM, 50 nM, and 100 nM of alsertib together with 0 nM, 50 nM, 100 nM, and 250 nM of decitabine. As shown in FIG. 3 and as listed in Table 7 below, the majority of the cancer cell lines evaluated were synergistically inhibited by the combination of decitabine and alisertib with cumulative Bliss synergy scores greater than 0.5 (i.e., sum of Bliss synergy across all dose combinations tested).

TABLE 7

Cumulative Bliss Synergy Scores for Cancer Cell Lines

| Cell Line | Organ | Bliss Synergy Score |
| --- | --- | --- |
| HEK293T | Normal | 0.205527622 |
| HEPS | Normal | −0.736108968 |
| E006 | Prostate | 2.826403774 |
| PC3 | Prostate | 2.431564737 |
| DU145 | Prostate | 2.350314854 |
| C42B | Prostate | 1.264130879 |
| LAPC4 | Prostate | 0.932239125 |
| CWR | Prostate | 0.843192034 |
| VCaP | Prostate | 0.395932069 |
| LNCaP-ABL | Prostate | 0.298191692 |
| LNCaP | Prostate | −1.207701763 |
| SKOV3 | Ovarian | 2.280471702 |
| A549 | Lung | 2.498945516 |
| HCT116 | Colon | 1.822309858 |
| DLD1 | Colon | 1.365102134 |
| SNB19 | CNS | 3.383951368 |
| SF539 | CNS | 2.3571 |
| MCF7 | Breast | 2.235554779 |
| MDA-MB-231 | Breast | 1.240749909 |
| T47D | Breast | −1.781394458 |

Both of the non-cancer cell models (hepatocytes and HEK293T cells) were not synergistically inhibited by the combination. Although the combination of decitabine and alisertib were antagonistic in LNCaP and T47D cells, the mechanistic dissection of this antagonism is ongoing. Nonetheless, these data suggest that combination therapy with DNMTi and AURKAi may have broad therapeutic benefit in multiple cancer types. Additionally, the very low activity of the single agents in the cancer cells across the doses tested and the high degree of growth inhibition in the combination is consistent with the predictions of the ISLET paradigm.

Figure 4:
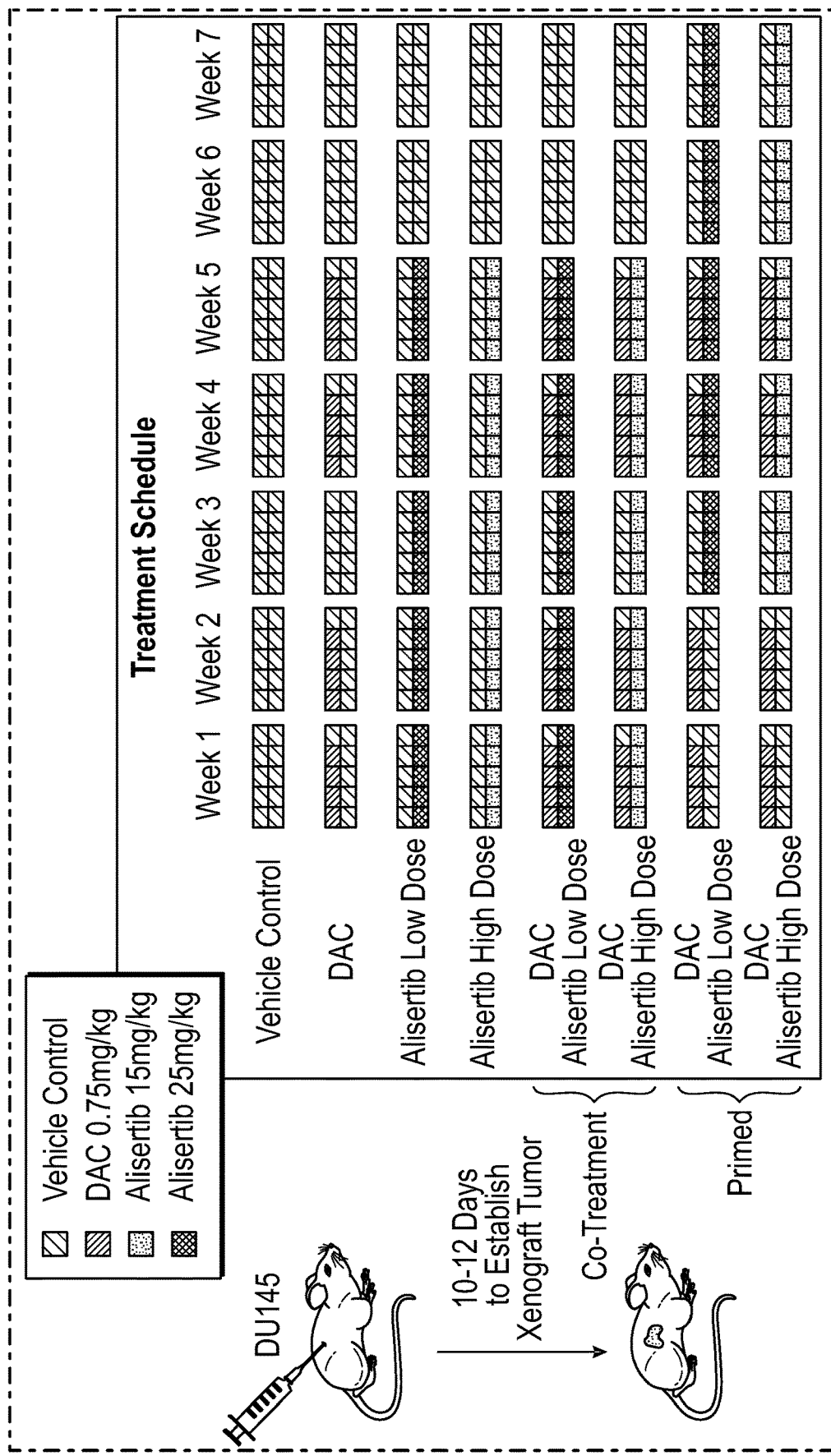
FIG. 4 shows an illustration of the treatment schedule for administration of decitabine and alisertib received by the nude mice of Example 3.

Example 3—Combination of DNMTi and AURKAi Showed Cancer Growth Inhibition In Vivo Using in vivo xenograft studies of the DU145 prostate cancer cell line, the effect was explored of the treatment of two dose levels of alisertib alone or in combination with decitabine using two different treatment time schedules over a period of seven weeks. First, nude mice were inoculated with DU145 cells that were allowed to incubate for 10-12 days to establish xenograft tumor. The inoculated mice were then treated concomitantly with both a high dose and a low dose of alisertib and decitabine in the first two weeks or primed with decitabine alone for two weeks followed by alisertib alone in the first cycle. The treatment time schedules and dosage levels are shown in FIG. 4. The dose of decitabine was held constant at 0.75 mg/kg and given with either low-dose (15 mg/kg) or high-dose (25 mg/kg) alisertib, as indicated in FIG. 4. The cumulative number of doses of decitabine and alisertib was the same in all combination treatment arms in both schedules.

Figure 5A:
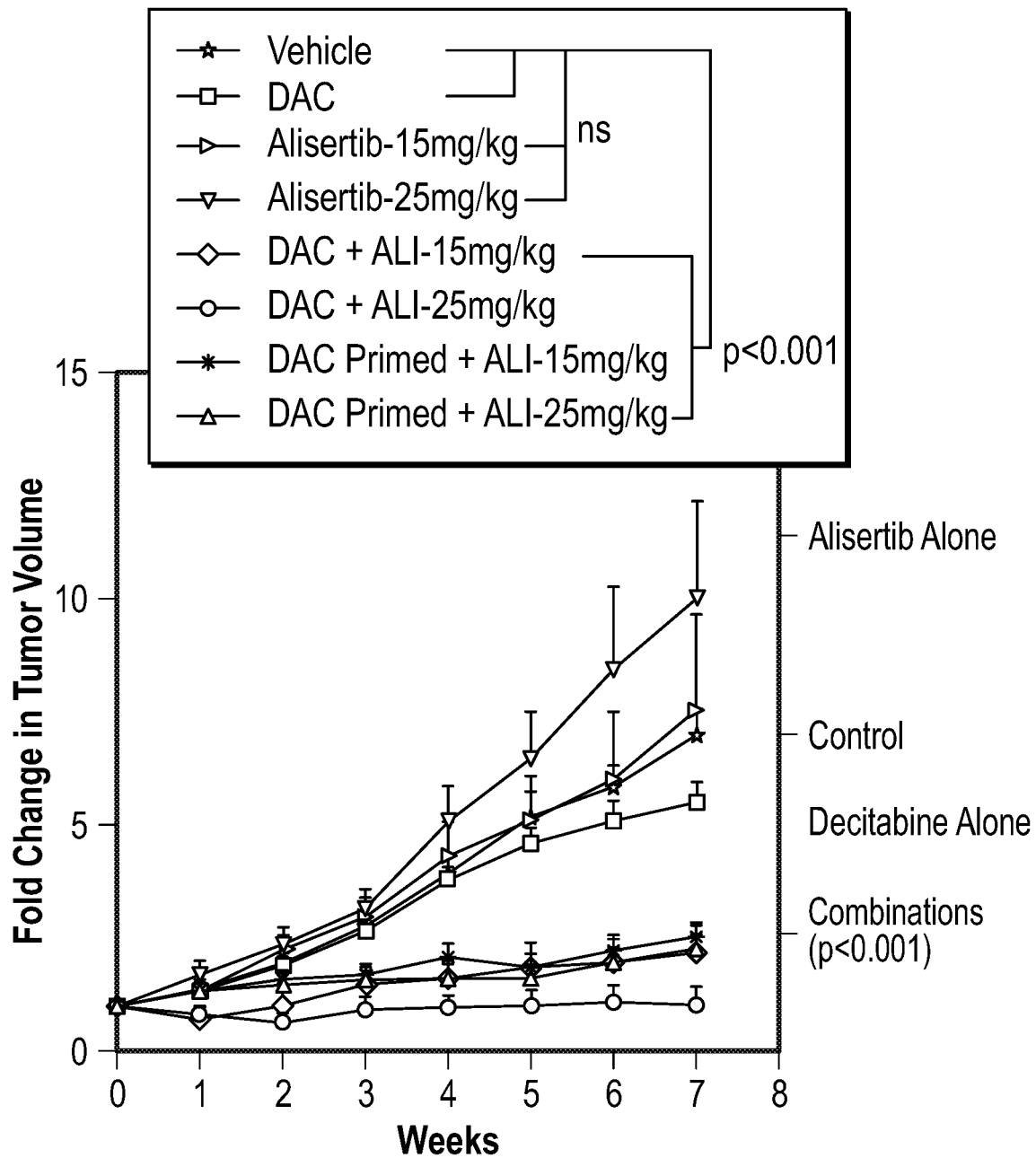
FIG. 5A is a graph showing the fold change in volume of tumors from mice administered a vehicle control, decitabine alone, high dose alisertib alone, low dose alisertib alone, decitabine concurrently with both high and low doses of alisertib, and decitabine as a primer followed by both high and low doses of alisertib.
Figure 5B:
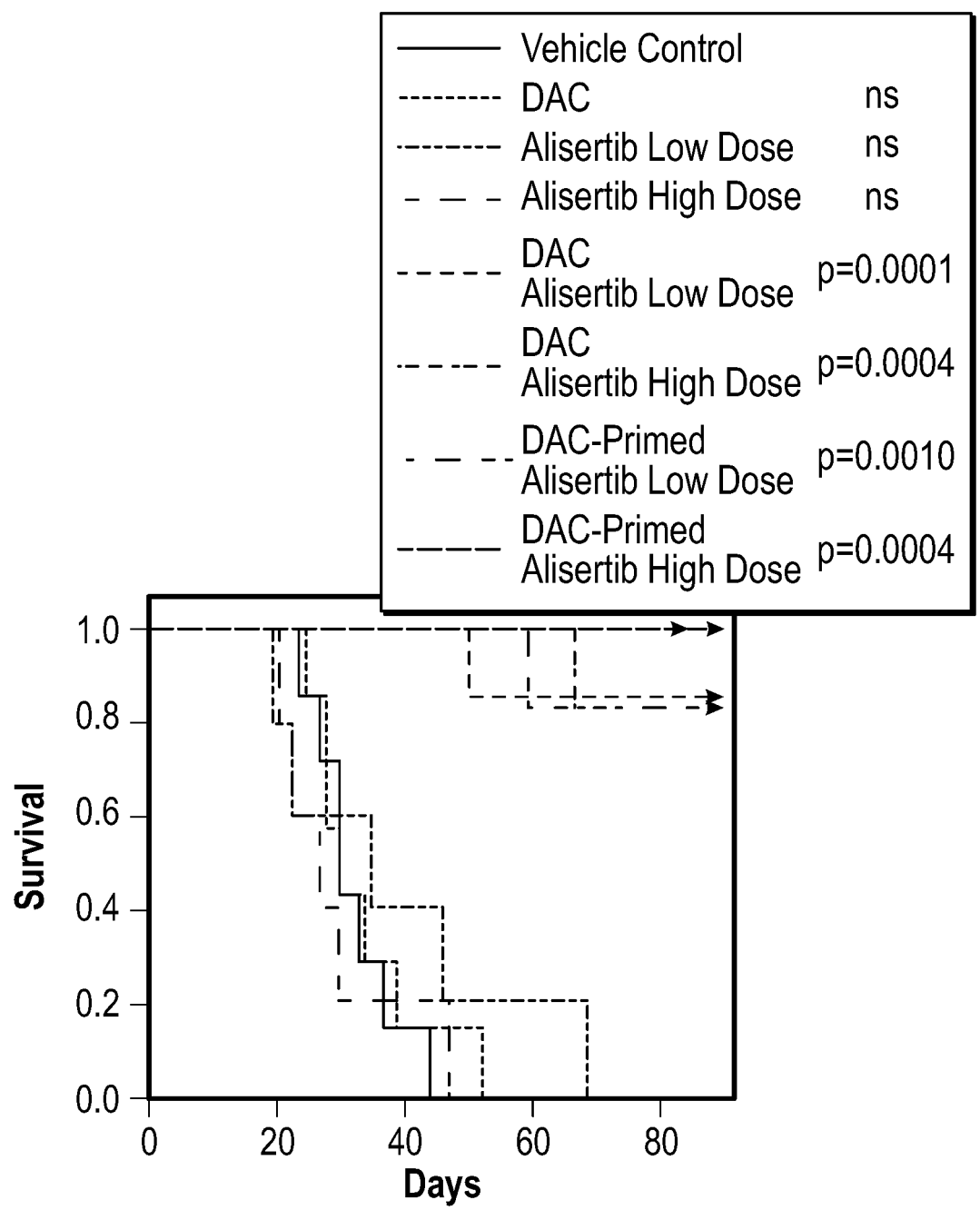
FIG. 5B is a graph showing the survival rates in days of mice administered a vehicle control, decitabine alone, high dose alisertib alone, low dose alisertib alone, decitabine concurrently with both high and low doses of alisertib, and decitabine as a primer followed by both high and low doses of alisertib.
Figure 6A:
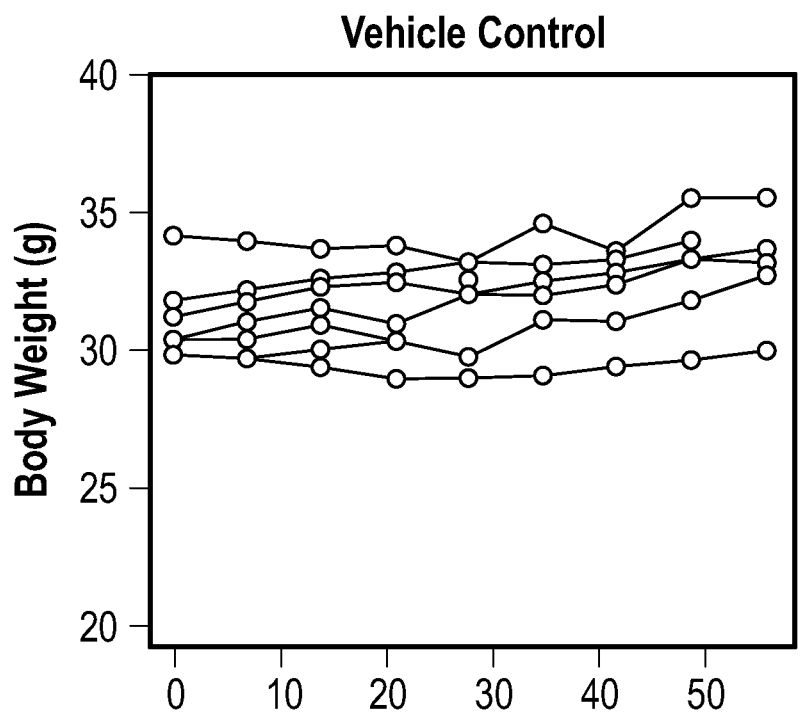
FIG. 6A is a graph showing the change in mice body weight over time during administration of a vehicle control.
Figure 6B:
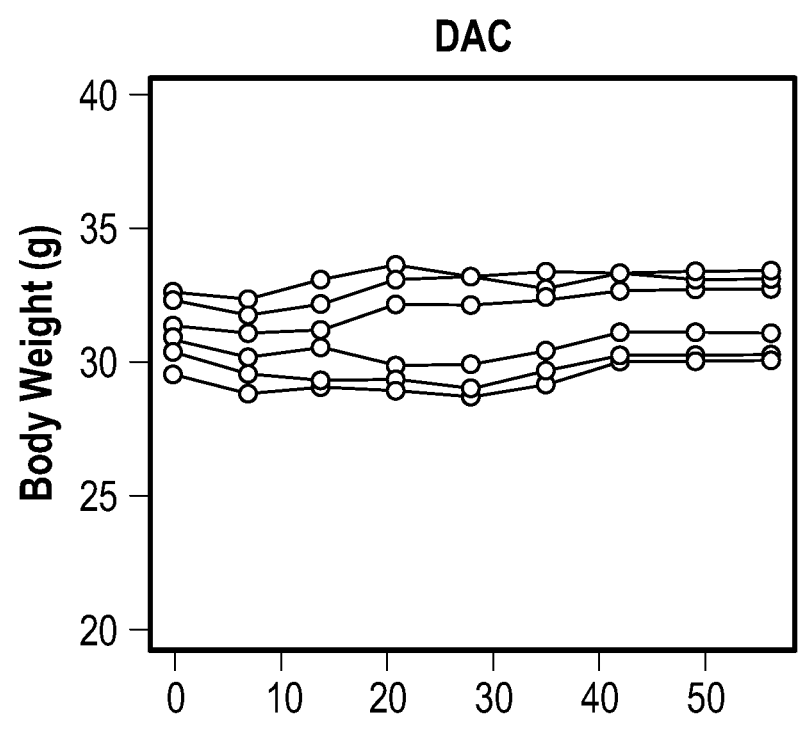
FIG. 6B is a graph showing the change in mice body weight over time during administration of decitabine.
Figure 6C:
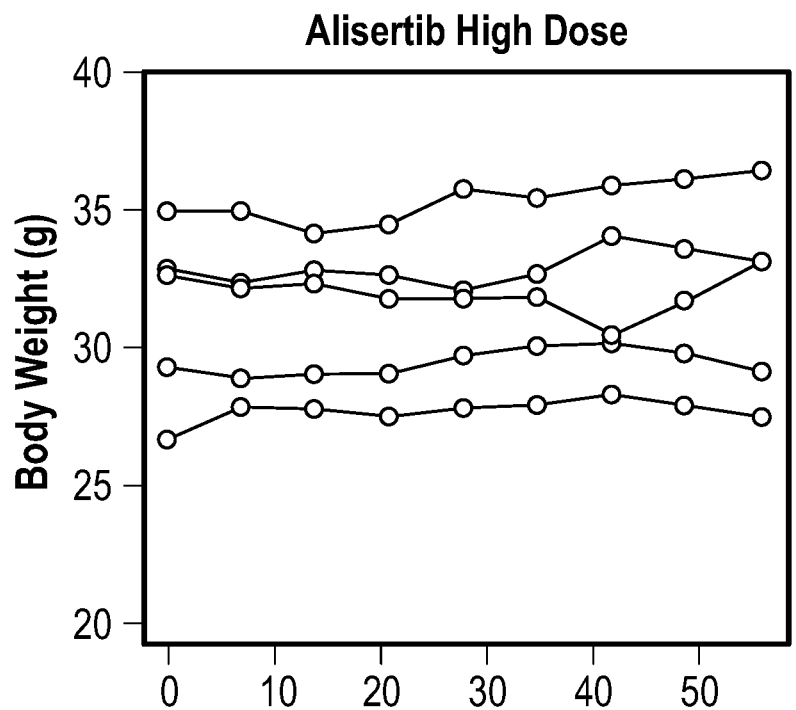
FIG. 6C is a graph showing the change in mice body weight over time during administration of a low dose (15 mg/kg) of alisertib.
Figure 6D:
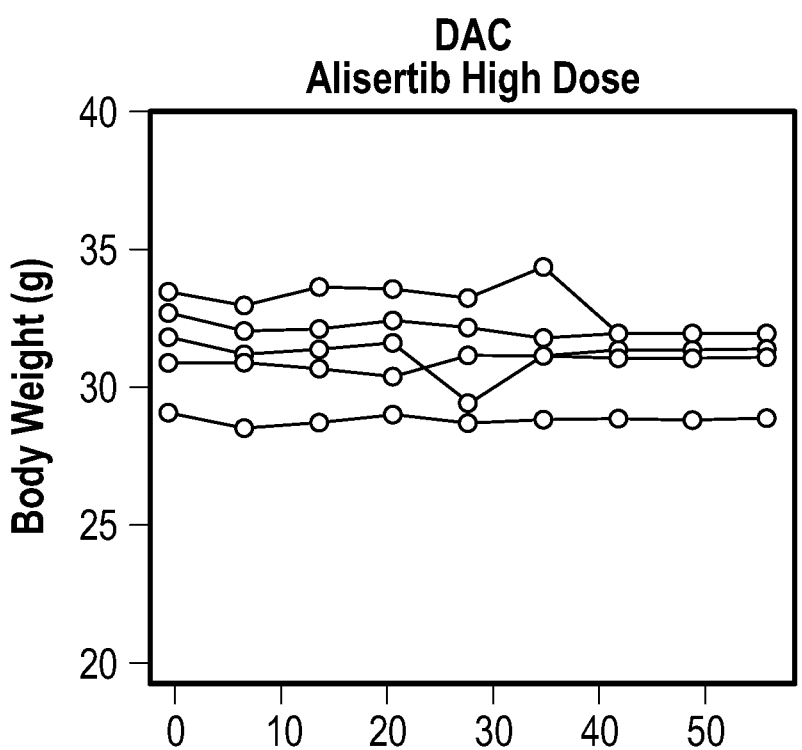
FIG. 6D is a graph showing the change in mice body weight over time during administration of a high dose (25 mg/kg) of alisertib.

Results of these studies are shown in FIGS. 5A and 5B and in Tables 8 and 9 below, indicating a fold change in tumor size from the initial tumor size, i.e., a ratio of the tumor size at the given time to the initial tumor size. Single agent therapy with decitabine or alisertib alone at the doses tested did not significantly alter xenograft tissue growth or survival compared to the vehicle control.

TABLE 8

Fold Change in Tumor Size

| Time (weeks) | Vehicle Control | | DAC | | Alisertib (low dose; 15 mg/kg) | | Alisertib (high dose; 25 mg/kg) | |
| --- | --- | --- | --- | --- | --- | --- | --- | --- |
| | Mean | SEM | Mean | SEM | Mean | SEM | Mean | SEM |
| 0 | 1 | 0 | 1 | 0 | 1 | 0 | 1 | 0 |
| 1 | 1.37 | 0.08 | 1.31 | 0.10 | 1.31 | 0.14 | 1.69 | 0.29 |
| 2 | 1.93 | 0.15 | 1.90 | 0.20 | 2.25 | 0.25 | 2.35 | 0.42 |
| 3 | 2.75 | 0.20 | 2.68 | 0.25 | 2.96 | 0.47 | 3.16 | 0.43 |
| 4 | 3.92 | 0.35 | 3.81 | 0.27 | 4.33 | 0.79 | 5.08 | 0.81 |
| 5 | 5.19 | 0.53 | 4.60 | 0.43 | 5.12 | 0.98 | 6.47 | 1.07 |
| 6 | 5.85 | 0.46 | 5.10 | 0.45 | 6.02 | 1.46 | 8.46 | 1.83 |
| 7 | 7.01 | 0.57 | 5.49 | 0.47 | 7.54 | 2.10 | 9.98 | 2.20 |

TABLE 2

| | Fold Change in Tumor Size | | | | | | | |
|---|---|---|---|---|---|---|---|---|
| | DAC + Alisertib (low dose; 15 mg/kg) | | DAC + Alisertib (high dose; 25 mg/kg) | | DAC Primed + Alisertib (low dose; 15 mg/kg) | | DAC Primed + Alisertib (high dose; 25 mg/kg) | |
| Time (weeks) | Mean | SEM | Mean | SEM | Mean | SEM | Mean | SEM |
| 0 | 1 | 0 | 1 | 0 | 1 | 0 | 1 | 0 |
| 1 | −1.17 | 0.64 | −0.76 | 0.66 | 1.30 | 0.09 | 1.32 | 0.12 |
| 2 | −0.66 | 1.09 | −1.97 | 0.83 | 1.59 | 0.11 | 1.48 | 0.26 |
| 3 | −0.66 | 1.84 | −1.10 | 1.00 | 1.70 | 0.18 | 1.26 | 0.53 |
| 4 | −0.77 | 1.99 | −0.81 | 1.13 | 2.06 | 0.31 | 1.22 | 0.66 |
| 5 | −1.01 | 2.34 | −1.50 | 1.35 | 1.88 | 0.26 | 1.27 | 0.58 |
| 6 | −0.91 | 2.37 | −1.33 | 1.62 | 2.22 | 0.24 | 1.63 | 0.58 |
| 7 | −0.68 | 2.43 | −2.71 | 2.38 | 2.52 | 0.23 | 1.92 | 0.64 |

As shown in FIG. 5A, the tumors continued to grow at a significant rate for the mice inoculated with all of vehicle control, decitabine alone, high dose alisertib, and low dose alisertib. To the contrary, little, if any, significant tumor growth was observed for the mice inoculated with decitabine concurrently with both low dose and high dose alisertib and decitabine primed before administration of both low dose and high dose alisertib.

In addition to resulting in significantly enhanced growth inhibition of DU145 xenografts, combinations of decitabine and alisertib also enhanced survival of the nude mice at both alisertib dose levels and time schedules. As shown in FIG. 5B, the mice inoculated with all of the vehicle control, decitabine only, high- and low-dose alisertib only had a mean survival of less than 40 days post-inoculation. To the contrary, the mice inoculated with combinations of decitabine and alisertib at both alisertib dose levels and time schedules had mean survival times that reached past the experimental threshold.

Example 4—In Vivo Toxicity Profile of the Combination of Decitabine and Alisertib The toxicity profile of the treated mice was observed, and the animals were weighed over the course of the experiment. As shown in FIGS. 6A-D, the mouse weights remained relatively stable throughout the experimental time course in all the treatment groups, suggesting that this regimen is relatively well-tolerated.

Figure 7A:
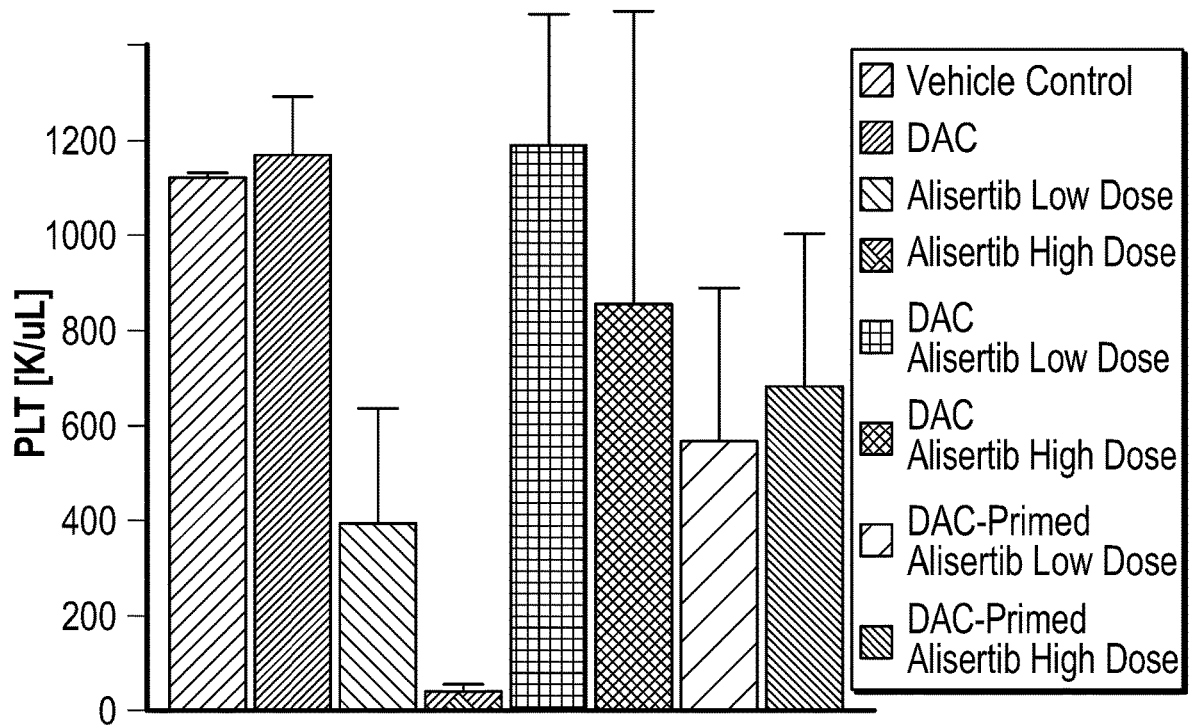
FIG. 7A is a bar graph showing mouse platelet (PLT) levels after administration of a vehicle control, decitabine alone, high dose alisertib alone, low dose alisertib alone, decitabine concurrently with both high and low doses of alisertib, and decitabine as a primer and then followed by both high and low doses of alisertib.
Figure 7B:
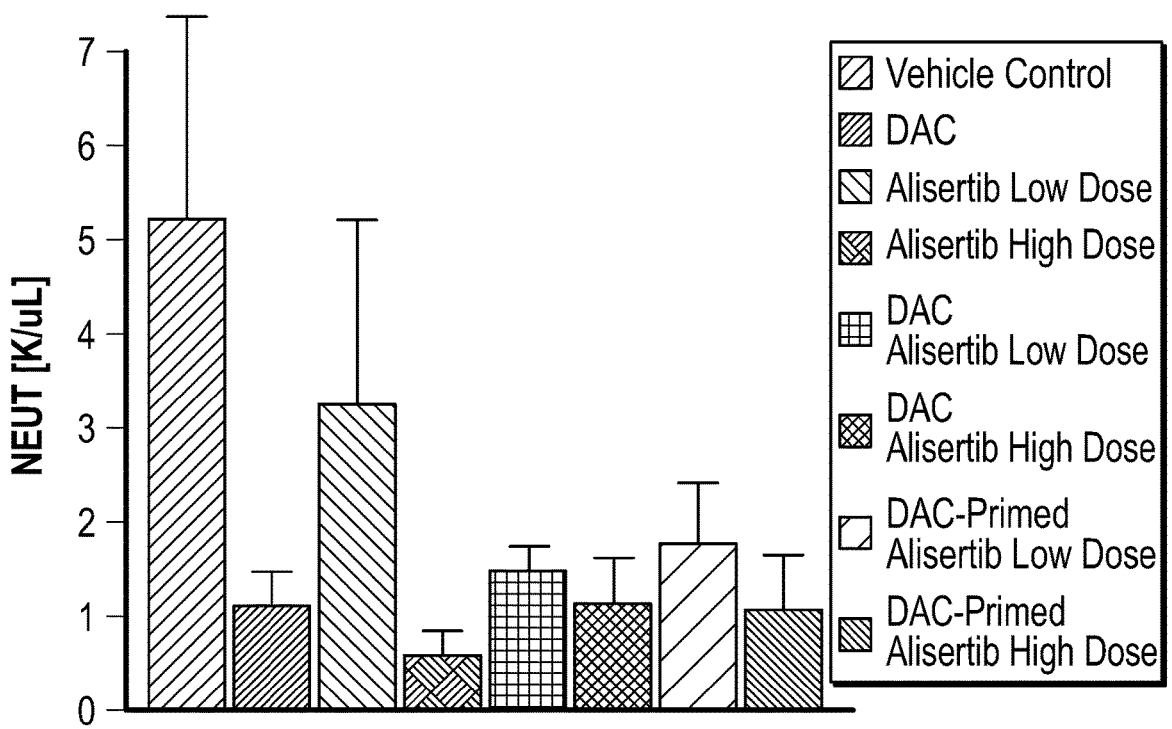
FIG. 7B is a bar graph showing mouse neutrophil (NEUT) levels after administration of a vehicle control, decitabine alone, high dose alisertib alone, low dose alisertib alone, decitabine concurrently with both high and low doses of alisertib, and decitabine as a primer and then followed by both high and low doses of alisertib.
Figure 7C:
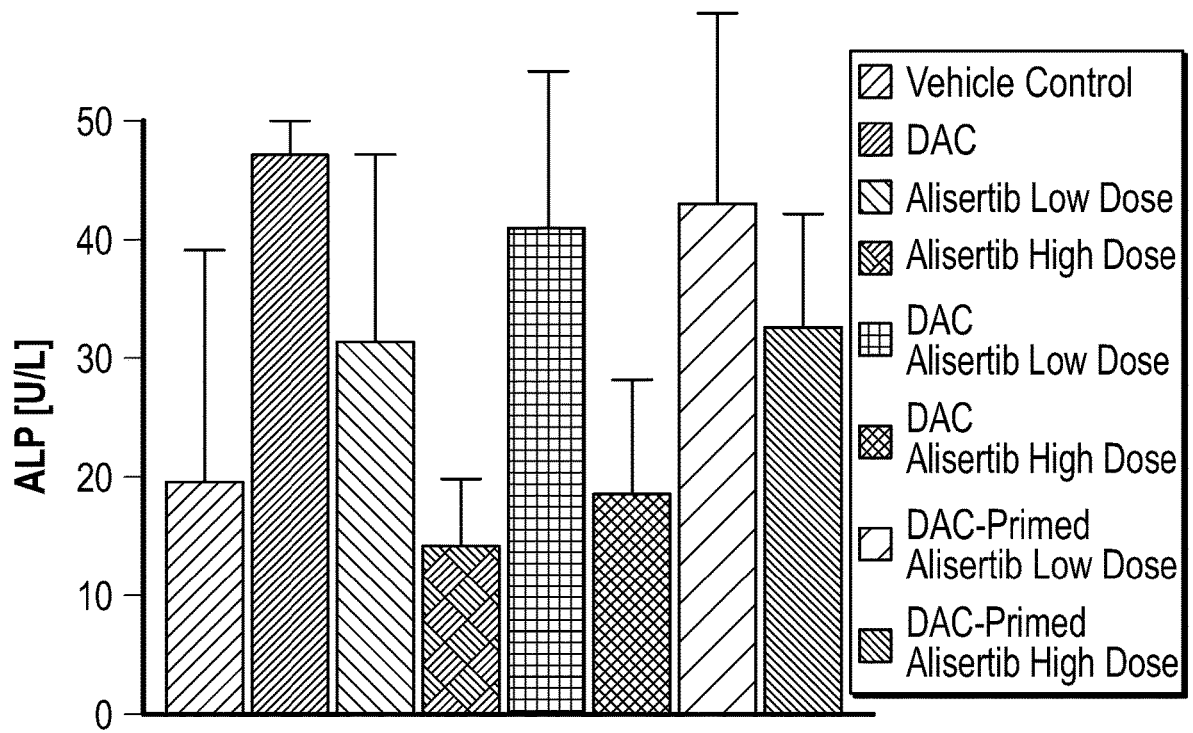
FIG. 7C is a bar graph showing mouse alkaline phosphatase (ALP) levels after administration of a vehicle control, decitabine alone, high dose alisertib alone, low dose alisertib alone, decitabine concurrently with both high and low doses of alisertib, and decitabine as a primer and then followed both high and low doses of alisertib.
Figure 7D:
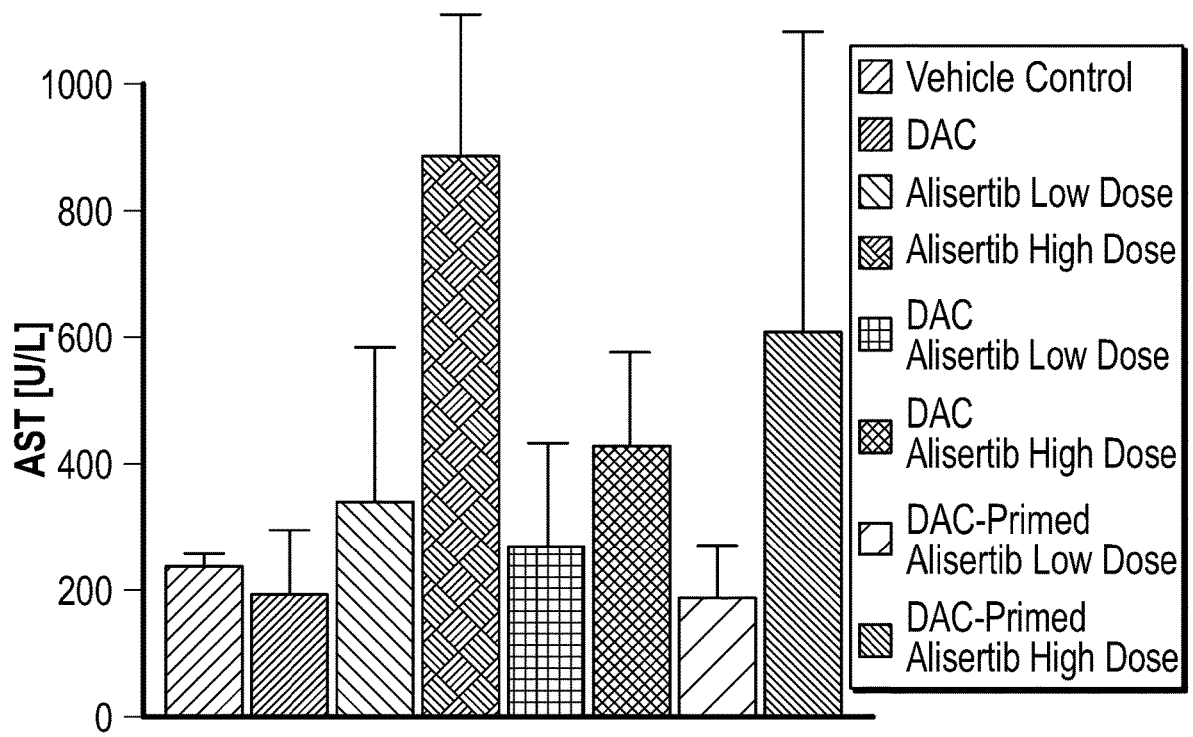
FIG. 7D is a bar graph showing mouse aspartate transaminase (AST) levels after administration of a vehicle control, decitabine alone, high dose alisertib alone, low dose alisertib alone, decitabine concurrently with both high and low doses of alisertib, and decitabine as a primer and then followed both high and low doses of alisertib.
Figure 7E:
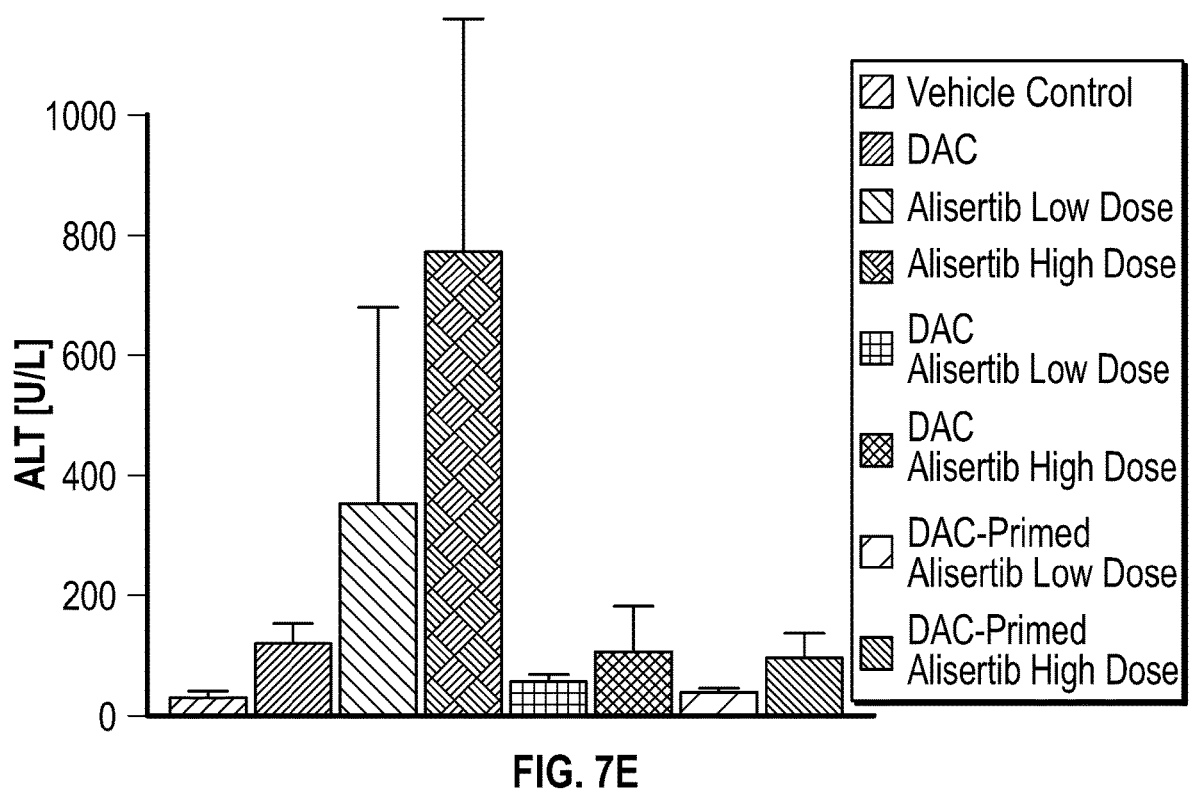
FIG. 7E is a bar graph showing mouse alanine aminotransferase (ALT) levels after administration of a vehicle control, decitabine alone, high dose alisertib alone, low dose alisertib alone, decitabine concurrently with both high and low doses of alisertib, and decitabine as a primer and then followed by both high and low doses of alisertib.

Combination therapy did not appear to worsen any hematological parameters, such as thrombocytopenia and neutropenia, compared to each drug alone, as shown in FIGS. 7A-E. In the case of thrombocytopenia, the combination appeared to be protective compared to alisertib alone, as shown in FIG. 7A.

With respect to liver function, elevated AST and ALT were observed with single agent alisertib treatment. See FIGS. 7D and 7E. However, as the graphs illustrate, the combination of decitabine and alisertib again appeared to be protective in this regard. Overall, the studies demonstrate protective effects and a lack of additive toxicities in the animal models for the combination of decitabine and alisertib.

Example 5—DNMTi can Induce a Long-Term Sensitization to AURKAi

It was investigated herein whether treatment with a DNMTi (decitabine) would induce a lasting epigenetic reprogramming and epigenetic memory that could later sensitize to an Aurora kinase A inhibitor (AURKAi) such as alisertib. DU145 cells were treated with a vehicle control or low dose decitabine (100 nM, similar to that used in the Examples above) in tissue culture. At this low dose, most of the cells survived and were allowed to recover with no drug for 4 days.

The vehicle and decitabine pre-treated cells were then implanted into nude mice and allowed to establish xenograft tumors for 3 weeks. The animals were then treated with either vehicle control or alisertib (MLN8237 at 15 mg/kg by oral gavage) every day for 5 weeks. Accordingly, four groups were established: (1) untreated DU145 mice receiving vehicle control; (2) untreated DU145 mice receiving alisertib; (3) decitabine pretreated DU145 mice receiving vehicle control; and (4) decitabine pretreated DU145 mice receiving alisertib.

Figure 8A:
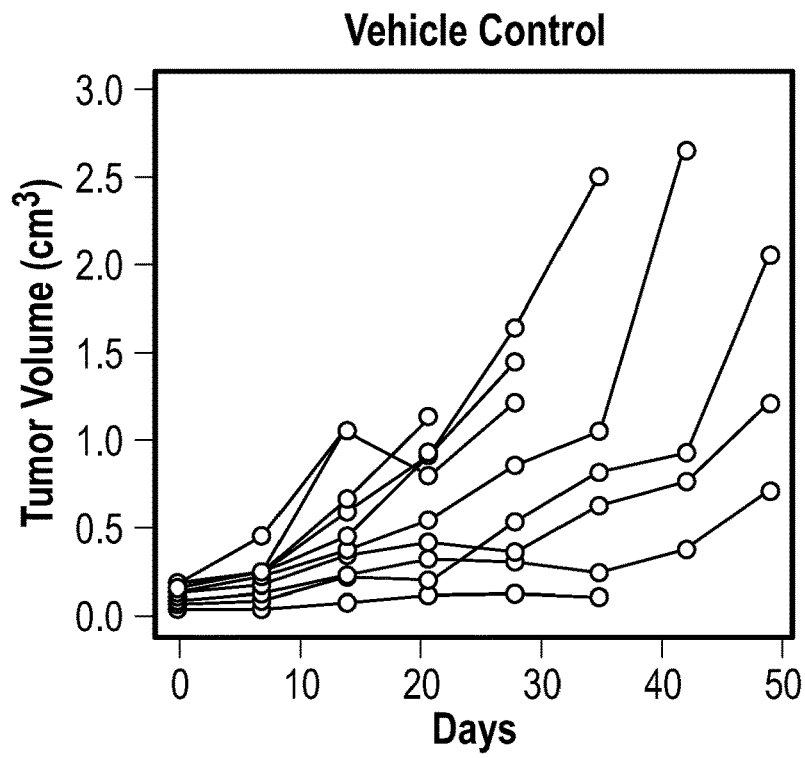
FIG. 8A is a graph showing the change in tumor volume over days in mice after administration of a vehicle control.
Figure 8B:
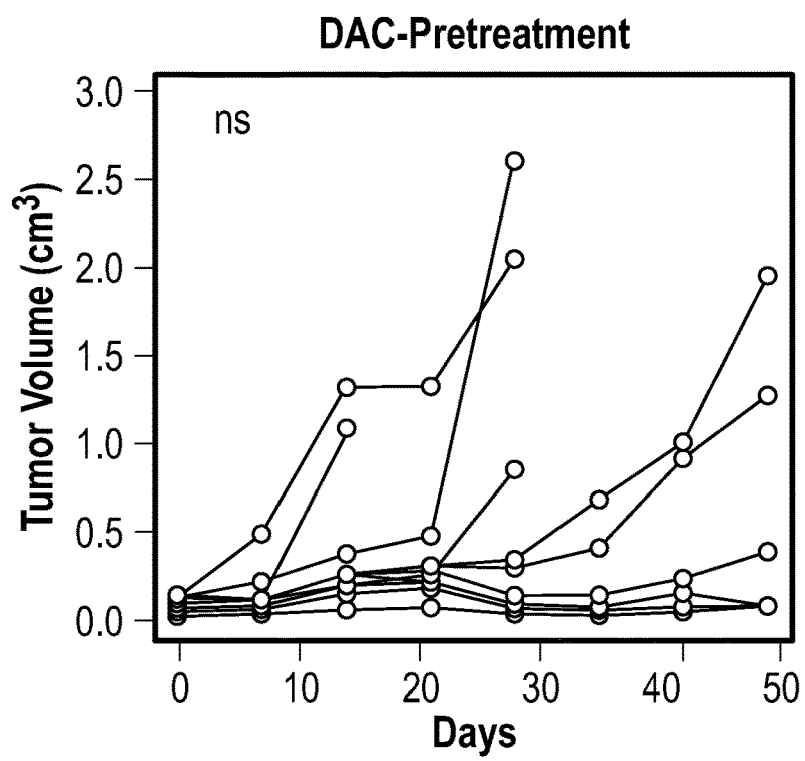
FIG. 8B is a graph showing the change in tumor volume over days in mice after pretreatment with decitabine (DAC).
Figure 8C:
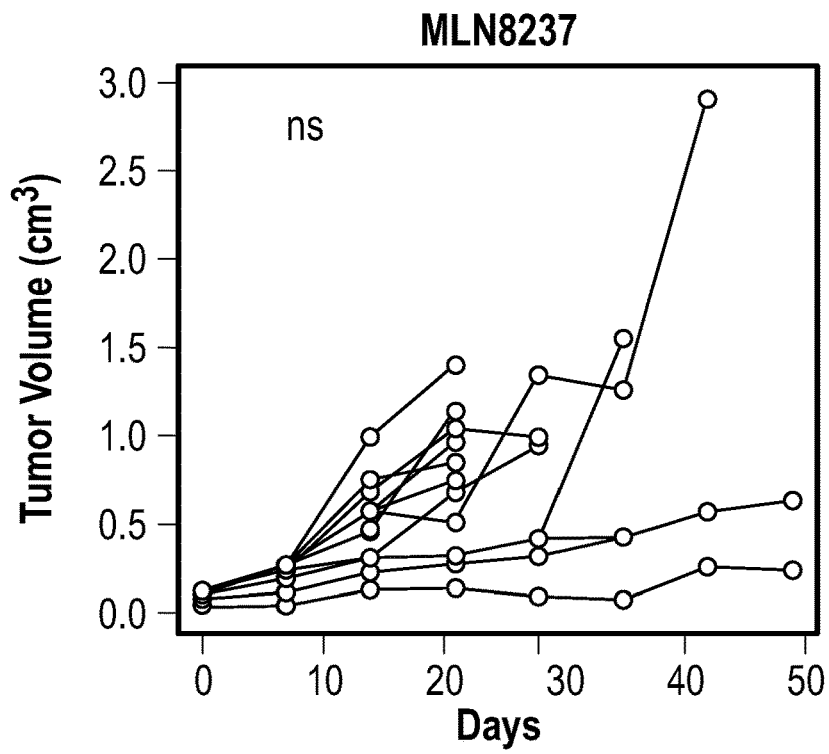
FIG. 8C is a graph showing the change in tumor volume over days in mice after administration of alisertib (MLN8237) with no pretreatment of decitabine.
Figure 8D:
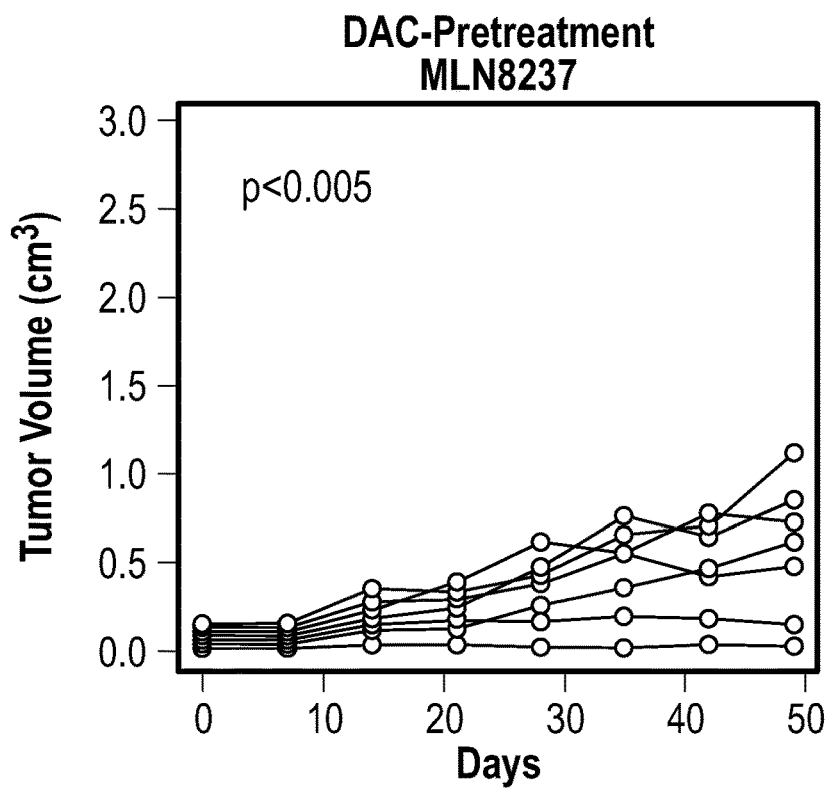
FIG. 8D is a graph showing the change in tumor volume over days after pretreatment with decitabine (DAC) followed by administration of alisertib (MLN8237).
Figure 9:
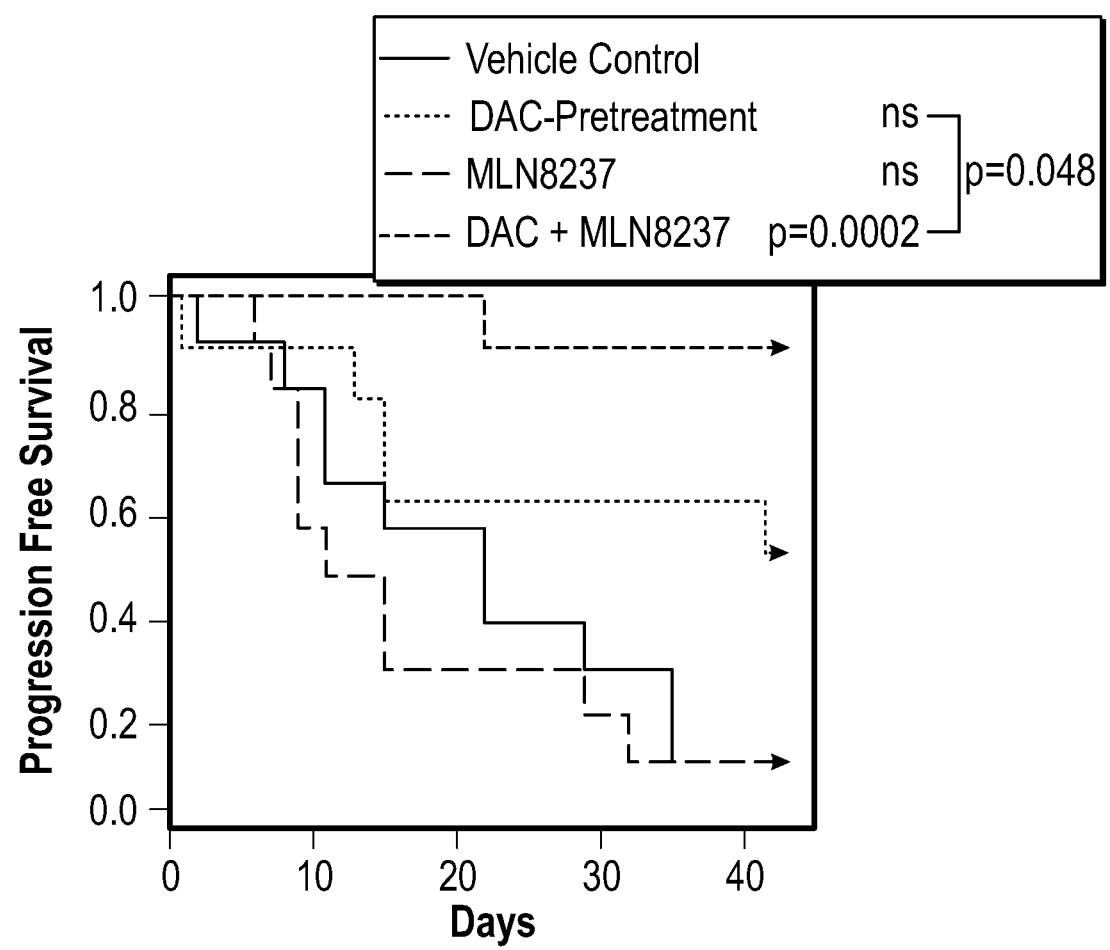
FIG. 9 is a graph illustrating the survival rates of mice administered a vehicle control and alisertib versus mice pretreated with decitabine and then administered alisertib.
Figure 10A:
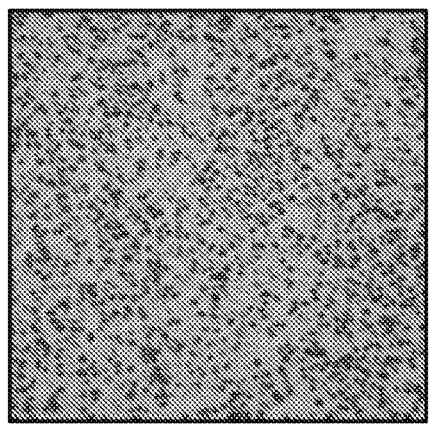
FIG. 10A is an image of sample cells stained with KI-67 from the vehicle control of Example 5.
Figure 10B:
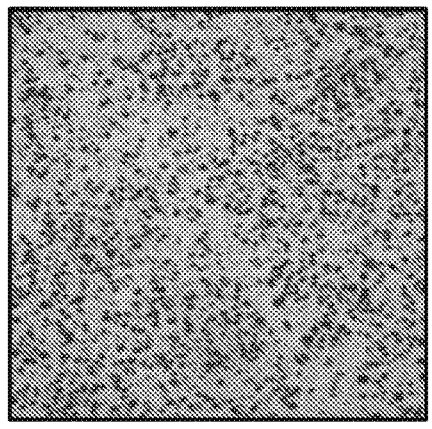
FIG. 10B is an image of sample cells stained with KI-67 that were pretreated with decitabine from Example 5.
Figure 10C:
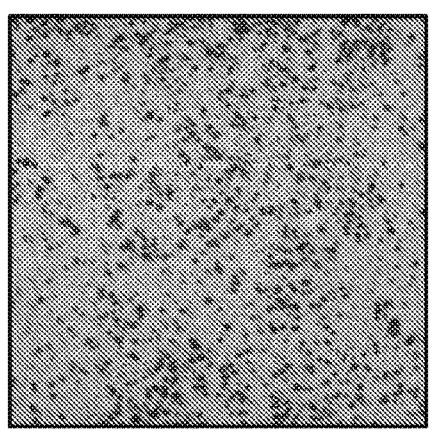
FIG. 10C is an image of sample cells stained with KI-67 from Example 5 not pretreated with decitabine and administered alisertib.
Figure 10D:
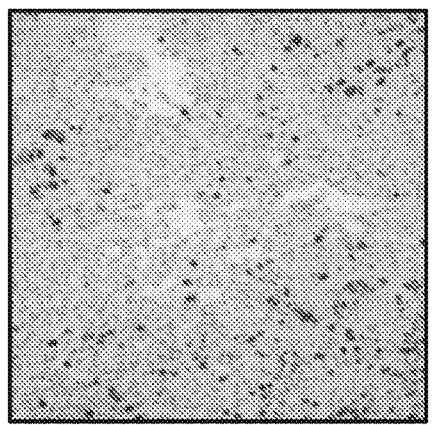
FIG. 10D is an image stained with KI-67 of sample cells from Example 5 pretreated with decitabine and administered alisertib.
Figure 10E:
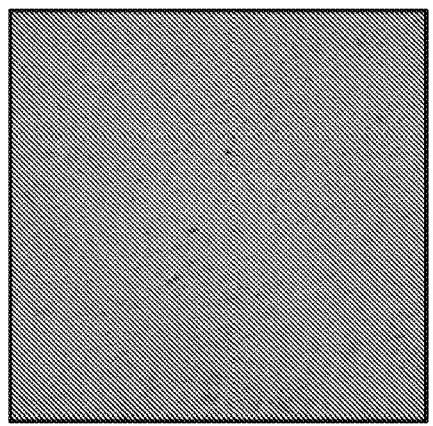
FIG. 10E is an image of sample cells stained using Caspase 3A from the vehicle control of Example 5.
Figure 10F:
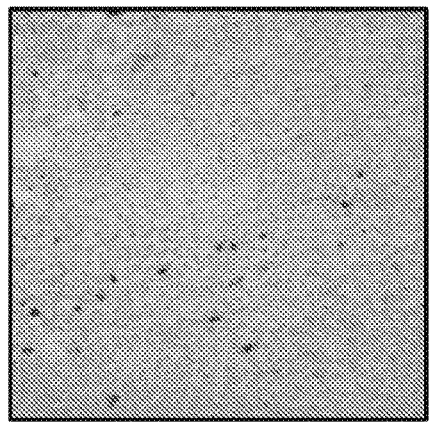
FIG. 10F is an image of sample cells stained using Caspase 3A that were pretreated with decitabine from Example 5.
Figure 10G:
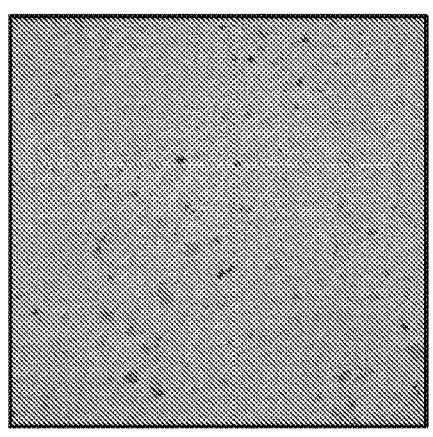
FIG. 10G is an image of sample cells stained using Caspase 3A from Example 5 not pretreated with decitabine and administered alisertib.
Figure 10H:
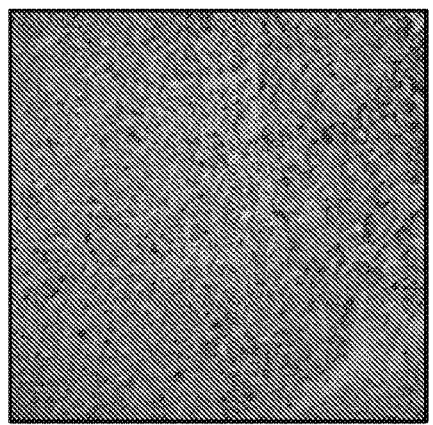
FIG. 10H is an image stained using Caspase 3A of sample cells from Example 5 pretreated with decitabine and administered alisertib.

FIG. 8A is a spider plot illustrating xenograft growth of the group administered a vehicle control. Spider plots of the xenograft growth revealed that the group with decitabine pre-treatment in culture and alisertib (MLN8237) treatment in vivo had significantly reduced xenograft growth, as shown FIG. 8D, compared to decitabine pre-treatment alone or alisertib alone, as shown in FIGS. 8B and 8C. This translated to significantly improved survival, as shown in FIG. 9. Thus, the pre-treatment with decitabine in vitro appeared to induce a long-term sensitization to AURKAi that could be observed even after the cells were allowed to recover and establish as xenograft tumors over a multiple-week period.

The proliferative index and apoptotic fraction in residual xenograft tumors from the decitabine pre-treatment experiment was then examined Sample cells from each of the vehicle control, decitabine pre-treatment alone, alisertib alone, and decitabine pretreatment in combination with alisertib were stained with either KI-67 or Caspase 3A. As shown in FIGS. 10A-D, there was a profound reduction in KI-67 staining (indicative of reduced cell proliferation). Furthermore, as shown in FIGS. 10E-H, there was a significant increase in Caspase 3A staining (indicative of increased apoptosis) in the decitabine pre-treated and alisertib treated group. However, in the vehicle control, decitabine pre-treatment alone, and alisertib treatment alone groups, there were almost no alteration in the KI-67 and Caspase 3A immunohistochemical (IHC) levels. See FIGS. 10A-H. This suggests that the pre-treatment with decitabine induced a long-term sensitization to the AURKAi that manifested as a profound reduction in proliferation and increase in apoptosis upon treatment with the AURKAi in the animals even weeks after the tumor cells were initially treated with low-dose decitabine.

Example 6—Mechanism of Action of ISLET by DNMTi and AURKAi

Figure 11A:
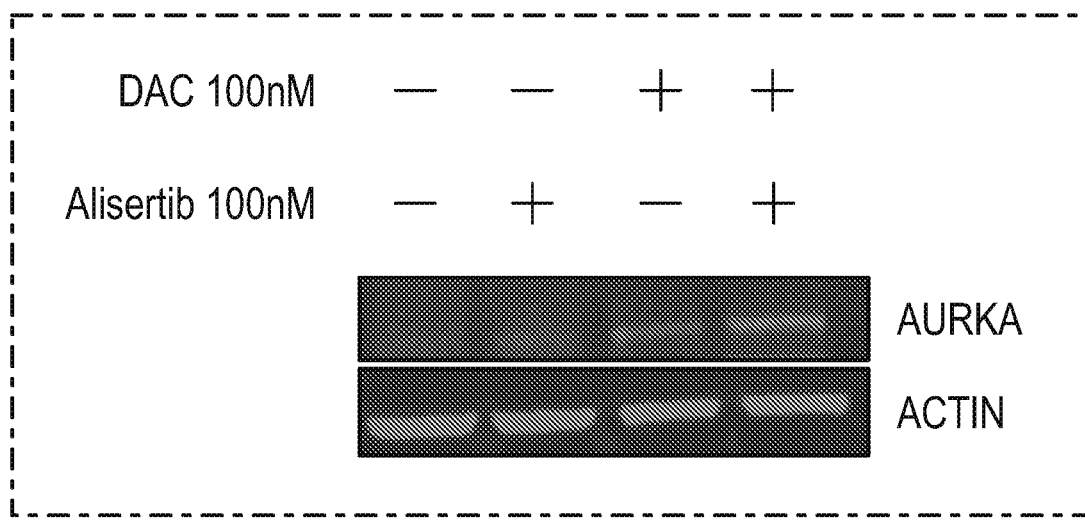
FIG. 11A is an image of Western Blot analyses for Aurora kinase A performed on DU145 cell tissue sample treated with vehicle control; 100 nM alisertib alone; 100 nM decitabine alone; and 100 nM of decitabine in combination with 100 nM of alisertib.

To begin investigating the mechanism of action of the induced synthetic lethality by the DNMTi (decitabine) and the AURKAi (alisertib), the effects of each inhibitor on DNA methyltransferase and Aurora Kinase A protein expression levels in DU145 cells were examined Western Blot analyses for AURKA were performed on DU145 cell tissue sample treated with vehicle control; 100 nM alisertib alone; 100 nM decitabine alone; and 100 nM of decitabine in combination with 100 nM of alisertib. It was found that decitabine treatment at low doses could significantly induce AURKA protein levels, and that this was further enhanced in combination with alisertib. See FIG. 11A.

Figure 11B:
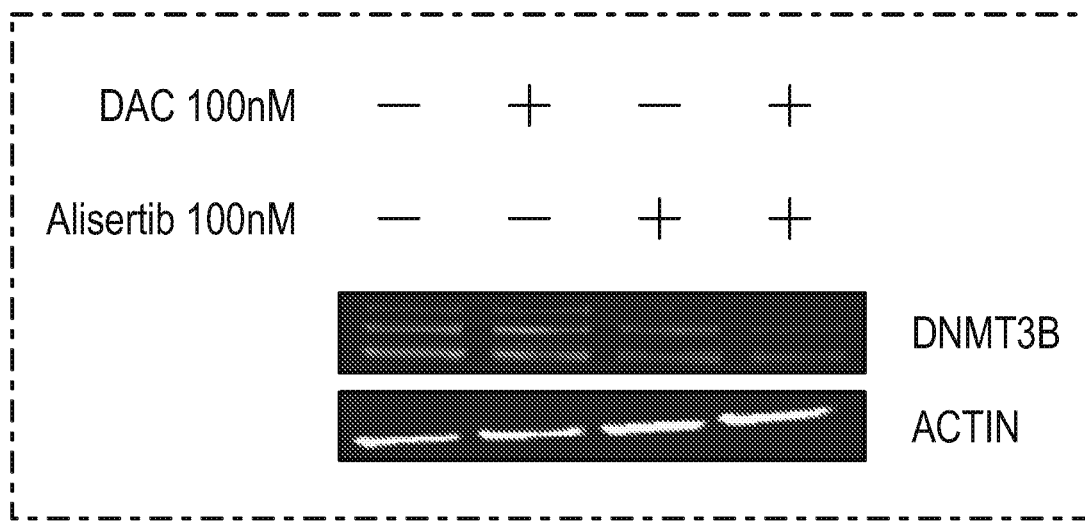
FIG. 11B is an image of Western Blot analyses for DNA methyltransferase 3-beta (DNMT3B) performed on DU145 cell tissue sample treated with vehicle control; 100 nM alisertib alone; 100 nM decitabine alone; and 100 nM of decitabine in combination with 100 nM of alisertib.

DNA methyltransferase enzymes comprise a family of enzymes including DNMT1, DNMT3A, and DNMT3B. Decitabine is known to significantly reduce DNMT1 levels via covalent trapping and degradation; however, it is thought that decitabine alone does not reduce DNMT3B levels significantly. This latter observation was confirmed in studies in the DU-145 cells, as shown in FIG. 11B. In this study, Western Blot analyses for DNMT3B were performed on DU145 cell tissue sample treated with vehicle control; 100 nM alisertib alone; 100 nM decitabine alone; and 100 nM of decitabine in combination with 100 nM of alisertib. Decitabine significantly reduced DNMT1 levels (data not shown), but did not significantly alter DNMT3B levels. Alisertib alone did not significantly affect DNMT1 or DNMT3A levels (data not shown), but did significantly reduce DNMT3B levels, as shown in FIG. 11B. This DNMT3B depletion was further enhanced in the decitabine and alisertib combination treatment. In additional preliminary studies, it has been observed that the depletion of DNMT3B by alisertib may be due to decreased protein stability and enhanced proteasomal degradation of DNMT3B upon alisertib treatment rather than due to decreased production of DNMT3B.

These data suggest that AURKA may play a role in stabilization of DNMT3B, a hypothesis that may be investigated further. Overall, these data suggest that AURKAi and DNMTi can lead to reciprocal regulation of their target enzymes with decitabine leading to an unanticipated upregulation of AURKA and alisertib leading to an unanticipated downregulation of the DNA methyltransferase DNMT3B.

Figure 12A:
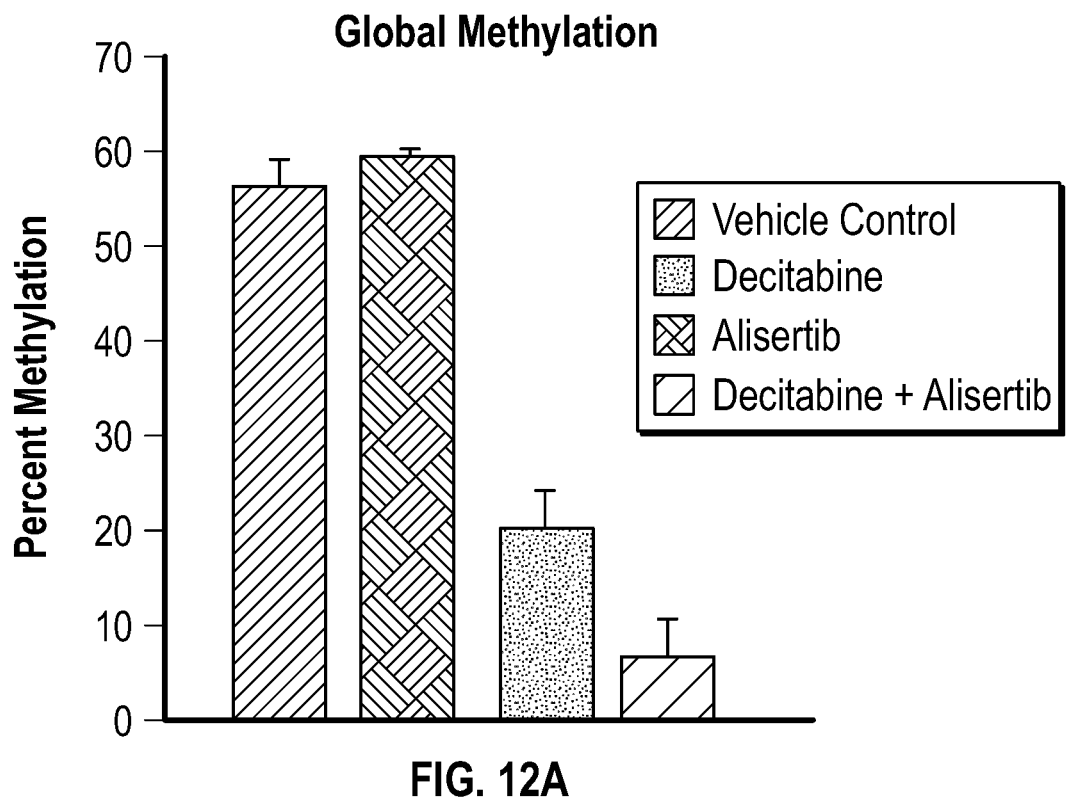
FIG. 12A is a bar graph illustrating the percent methylation, as measured by the LUMA assay, in DU145 cells containing vehicle control compared to cells containing decitabine or alisertib alone and cells containing a combination of decitabine and alisertib.

Because the combination of decitabine and alisertib leads to a significant reduction of both DNMT1 and DNMT3B, it is hypothesized that the combination treatment may lead to enhanced DNA demethylation. Luminometric Methylation Assay (LUMA) was used to measure DNA methylation for DU145 cells containing a vehicle control; decitabine; alisertib; and decitabine in combination with alisertib. It was found that global methylation levels, as measured by the LUMA assay, were significantly decreased in the combination treatment in DU145 cells compared to cells containing decitabine or alisertib alone. See FIG. 12A.

Figure 12B:
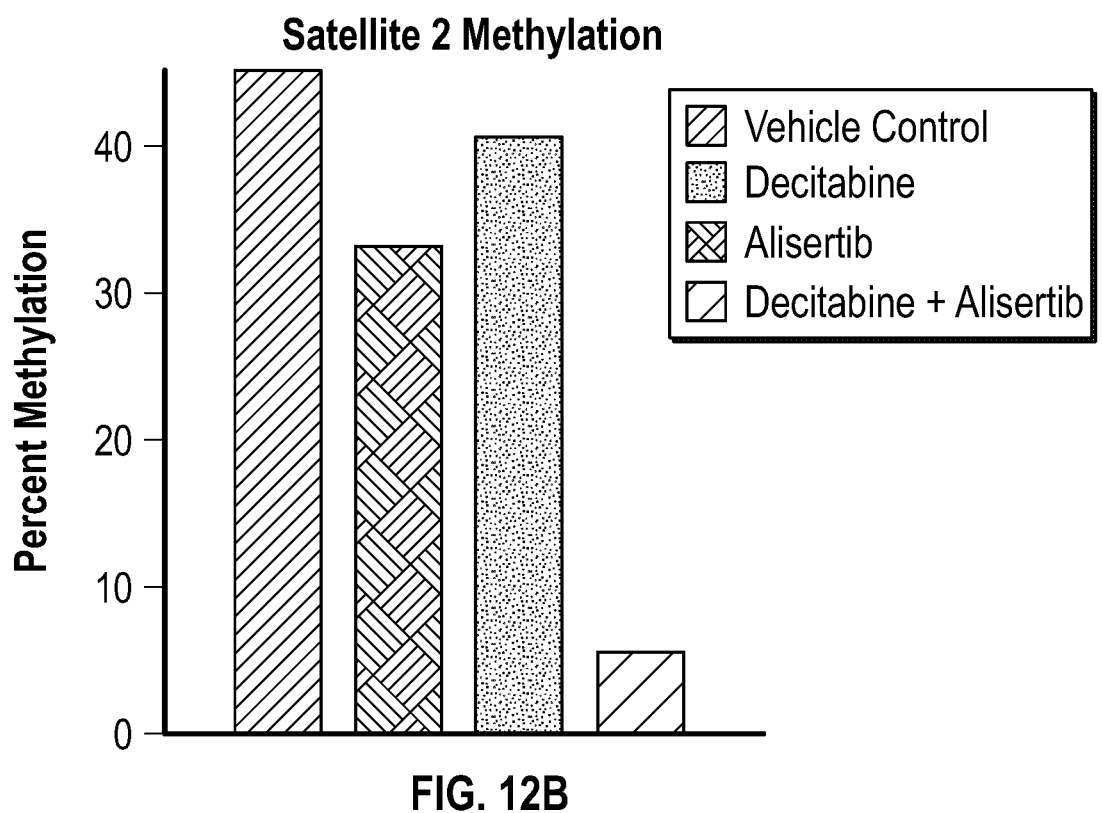
FIG. 12B is a bar graph illustrating percent of Satellite 2 methylation after bisulfite genomic sequencing in DU145 cells containing vehicle control compared to cells containing decitabine or alisertib alone and cells containing a combination of decitabine and alisertib.

As shown in FIG. 12B, bisulfite genomic sequencing of multiple classes of repetitive elements showed that pericentromeric sequences, such as Satellite 2 sequences, showed a particularly enhanced demethylation in the combination treatment of decitabine and alisertib compared to either drug alone. The percent of Satellite 2 methylation was significantly decreased below 10% in the combination treatment as compared to the vehicle control or either drug alone, all of which were above 30%. For the vehicle control, the percent of CpG Satellite 2 methylation was 45.09%, while it was 33.33% for decitabine alone and 40.6% for alisertib alone. The combination of decitabine and alisertib, however, resulted in a Satellite II methylation of 5.46%. See FIG. 12B. These findings are suggestive that depletion of both DNMT1 and DNMT3B by the combination of decitabine and alisertib may be able to precipitously reduce DNA methylation at the pericentromeric sequences.

Establishment and maintenance of the appropriate epigenetic marks, including DNA methylation, at pericentromeric regions may be relevant for chromosomal condensation, centromeric heterchromatinization, and appropriate centromeric function. AURKA activity is also important for appropriate centromere structure and spindle attachment during mitosis. Thus, it is hypothesized that the combination of decitabine and alisertib, by altering pericentromeric DNA methylation and preventing appropriate AURKA activity would lead to increased mitotic catastrophe compared to either agent alone.

Figure 13A:
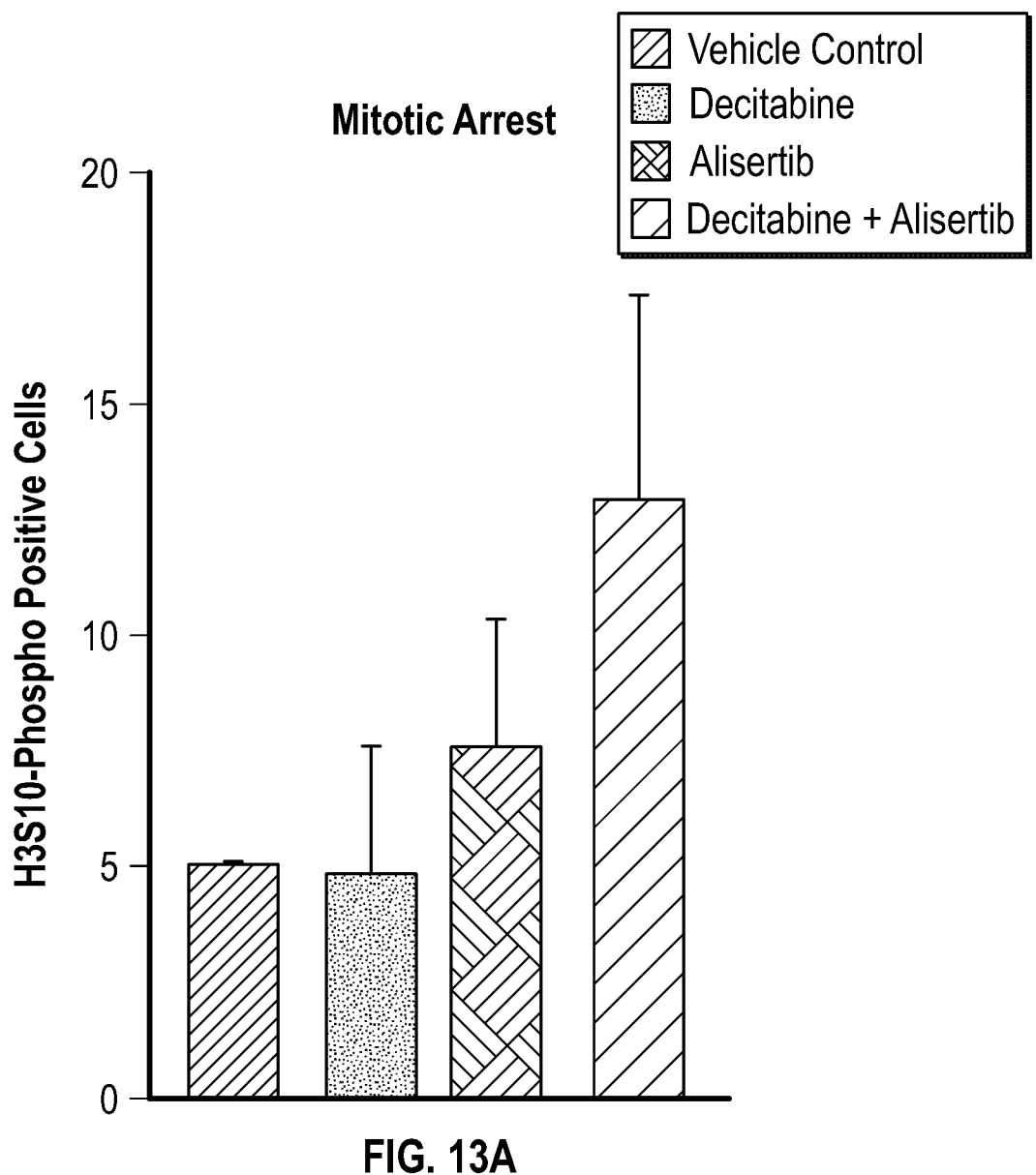
FIG. 13A is a bar graph showing H3S10-phospho positive cells after a combination treatment of decitabine and alisertib as compared to a vehicle control or treatment with either decitabine or alisertib alone.
Figure 13C:
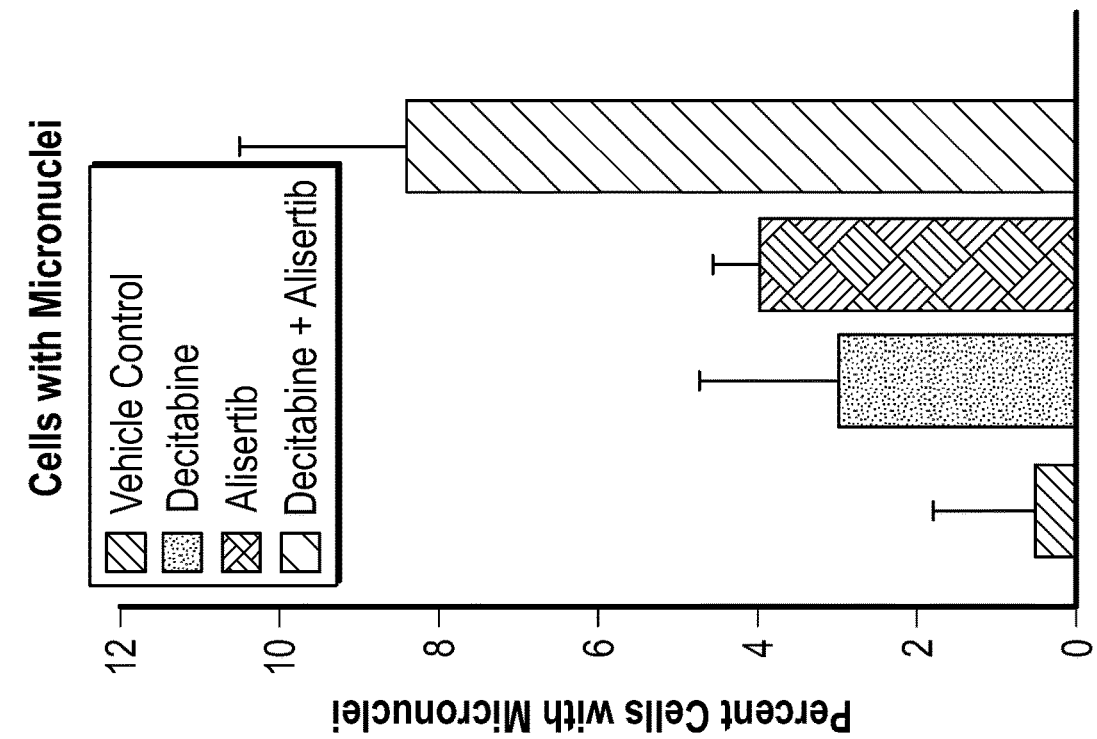
FIG. 13C is a bar graph showing the percentage of cells with micronuclei after a combination treatment of decitabine and alisertib as compared to a vehicle control or treatment with either decitabine or alisertib alone.
Figure 13B:
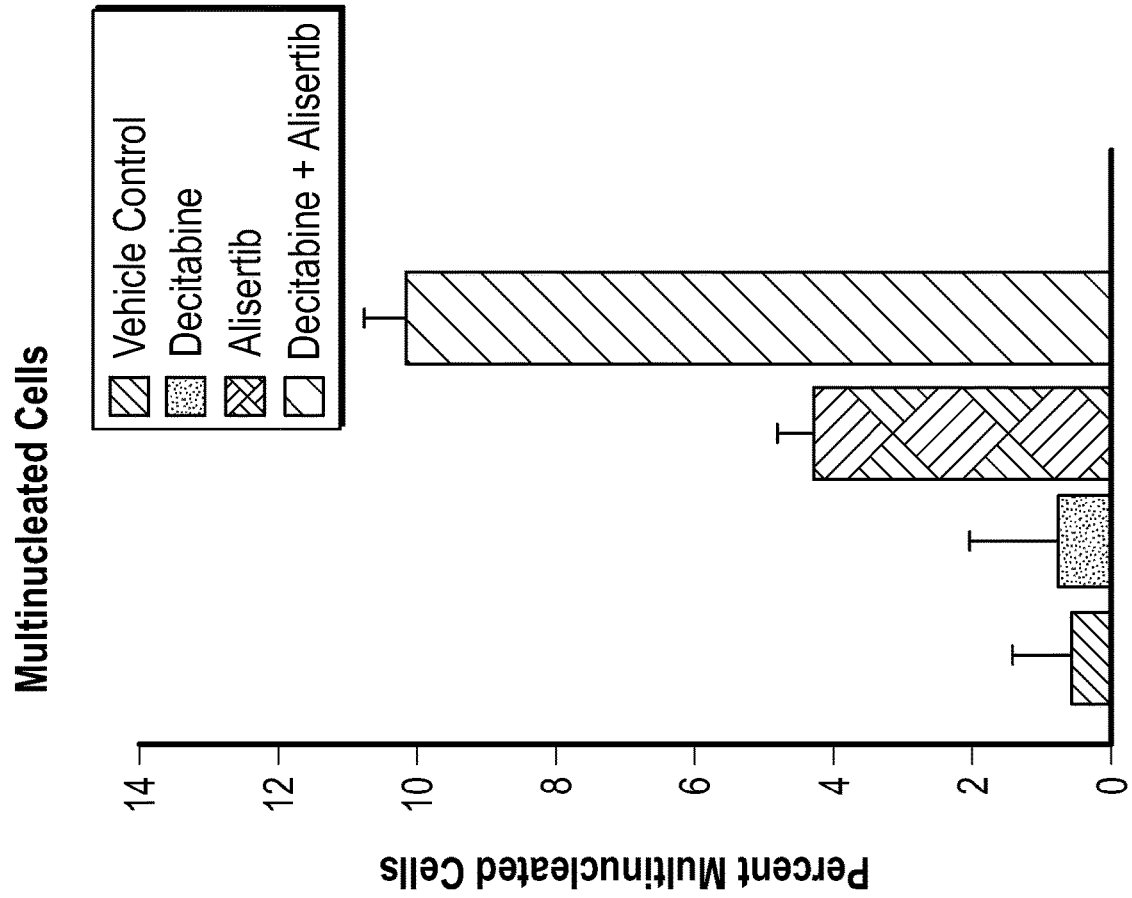
FIG. 13B is a bar graph showing the percentage of multinucleated cells after a combination treatment of decitabine and alisertib as compared to a vehicle control or treatment with either decitabine or alisertib alone.

Furthermore, the accumulation of H3S10-phosphorylation positive cells was measured, and, as shown in FIG. 13A, the combination treatment of decitabine and alisertib led to increased mitotic arrest as compared to a vehicle control or treatment with either decitabine or alisertib alone. Likewise, as shown in FIG. 13B, the combination treatment with decitabine and alisertib increased formation of multinucleated cells over treatment with a vehicle control, decitabine alone, or alisertib alone. Finally, as shown in FIG. 13C, the combination treatment with decitabine and alisertib increased the fraction of cells with micronuclei over treatment with a vehicle control, decitabine alone, or alisertib alone. All of mitotic arrest, multinucleated cells, and cells with micronuclei are indicators of mitotic catastrophe. Taken together, these initial mechanistic studies provide support to the notion that the combination of DNMTi and AURKAi can produce mitotic catastrophe in cancer cells through epigenetic dysregulation of the centromeric regions.

Example 7—Further Identification of ISLET Hits for Decitabine from Functional Genomic Screen A pooled lentiviral shRNA negative functional screen was carried out on a sample of DU145 prostate cancer cells according to the process described in Example 1 above and adapted from the procedure previously described in Schlabach M. R. et al., *Cancer Proliferation Gene Discovery through Functional Genomics*, SCIENCE, 319, 5863:620-4 (2008). DU145 prostate cancer cells were first treated with pooled lentiviral shRNA, resulting in the transduction of the RNA library. The lentiviral-transduced DU145 cells were then treated with decitabine. Accordingly, targets identified were selectively lethal in DU145 cells when treated with decitabine relative to control treated cells.

Flasks of DU145 cells were transduced with a genome-scale pooled lentiviral shRNA library. Each lentivirus in the pool encoded each of 27,500 shRNA constructs, shRNA specific barcodes, a puromycin resistance gene, and a fluorescence marker gene to track transduction levels. Each of 5,000 human genes were targeted by 5 to 6 shRNA encoding lentiviruses in the pool, and transduction was carried out at a low multiplicity of infection (MOI of approximately 0.3), in order to ensure that the majority of transduced cells would only receive a single lentiviral particle. Enough viruses and cells were transduced such that under this low MOI, each shRNA would be represented about 100 to about 1000 times in the population.

The library of transduced cells was then treated with decitabine (100 nM or 500 nM) or vehicle control, for 4 days or 7 days, all in 2 to 3 replicate experiments. After treatments, cells were harvested, DNA isolated, and 50 µg of genomic DNA was used to amplify the shRNA specific barcodes in surviving cells. These barcodes were then identified by next generation sequencing, and the number of each barcode corresponding to an individual shRNA in the population was used as the measure of the representation of that shRNA in the vehicle and decitabine treated cells. "Hits" were identified as those shRNAs that "dropped out" in the population of decitabine treated cells compared to the population of vehicle treated cells. Conversely, shRNAs that were enriched in the population of decitabine treated cells compared to the population of vehicle treated cells were considered to confer resistance to decitabine treatment.

Figure 14:
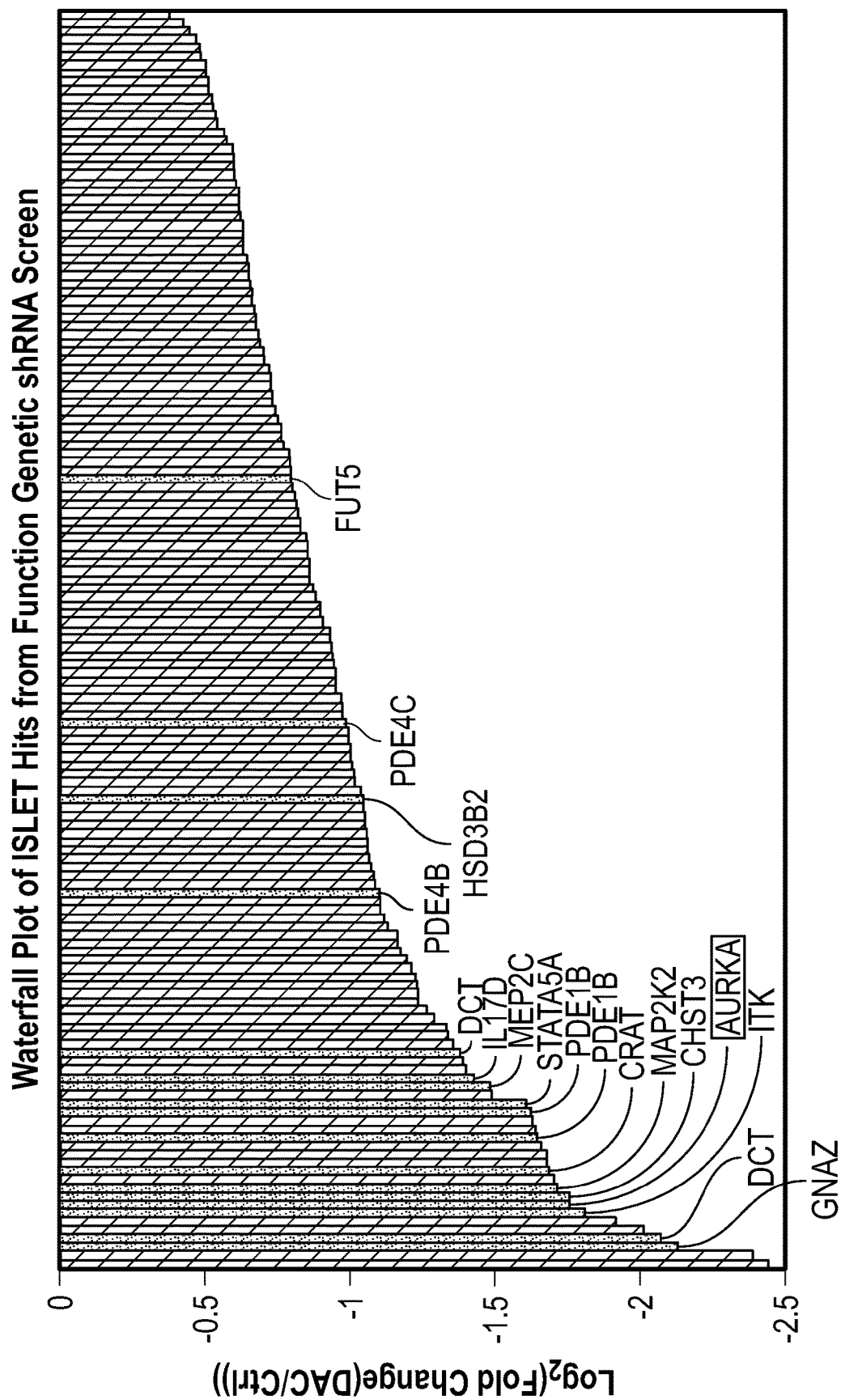
FIG. 14 is a waterfall plot of altered shRNA barcodes in the population of decitabine-treated versus control cells, identifying 149 genes having shRNAs sensitized to decitabine as they fell below 0.0 on the x-axis [$\log_2$(decitabine/control)].

Out of the 27,000 shRNAs tested in the pooled functional genomic screen, 149 were identified that were considered significant ISLET "hits," having a false discovery rate of about 1%. FIG. 14 is a waterfall plot showing the degree of selective killing in the shRNA both with and without decitabine plotted as the $\text{Log}_2$ transformation of the ratio of counts with decitabine treatment to counts with control treatment. As with FIG. 1A, above, the more negative the value, the greater the level of selective killing of the combination of the shRNA with decitabine compared to shRNA alone. Table 10 below details each of the 149 identified potential target genes.

TABLE 10

ISLET Hits from shRNA Functional Genomic Screen

| No. | Gene Symbol | Log2 [Fold Change (DAC/Control)] |
|---|---|---|
| 1 | PLA2G12A | −2.443049843 |
| 2 | EIF4A2 | −2.384947416 |
| 3 | GNAZ | −2.12923482 |
| 4 | DCT | −2.070953583 |
| 5 | SULT1C4 | −2.011668033 |
| 6 | HLX | −1.912200307 |
| 7 | ITK | −1.81076958 |
| 8 | AURKA | −1.75536014 |
| 9 | CHST3 | −1.755284814 |
| 10 | MAP2K2 | −1.714110825 |
| 11 | AADAT | −1.703665947 |
| 12 | CRAT | −1.688012791 |
| 13 | SULT4A1 | −1.678433786 |
| 14 | PDE4D | −1.676556078 |
| 15 | THY1 | −1.658974228 |
| 16 | PDE1B | −1.645199897 |
| 17 | BDH2 | −1.641077001 |
| 18 | QPRT | −1.630392687 |
| 19 | PDE1B | −1.622708751 |
| 20 | STAT5A | −1.616418262 |
| 21 | PHF21A | −1.487080744 |
| 22 | MEF2C | −1.482360977 |
| 23 | IL17D | −1.427600575 |
| 24 | SEL1L | −1.398498861 |
| 25 | COMT | −1.389049706 |
| 26 | DCT | −1.379642813 |
| 27 | SULT1C4 | −1.354881679 |
| 28 | GLRX | −1.334971707 |
| 29 | AKR1C4 | −1.333101055 |
| 30 | GNA12 | −1.28599537 |
| 31 | B4GALT1 | −1.262993523 |
| 32 | LEF1 | −1.237044531 |
| 33 | XYLT1 | −1.233098804 |
| 34 | GLRX | −1.230078208 |
| 35 | GNAQ | −1.226276273 |
| 36 | GCA | −1.208637736 |
| 37 | AGXT2 | −1.194701948 |
| 38 | DPM2 | −1.169841157 |
| 39 | OGDHL | −1.164245401 |
| 40 | UGT2B10 | −1.162061053 |
| 41 | PDE5A | −1.126645225 |
| 42 | QPRT | −1.119895316 |
| 43 | GPSM1 | −1.105656193 |
| 44 | LIG3 | −1.103252703 |
| 45 | PDE4B | −1.100930368 |
| 46 | LCMT1 | −1.086197336 |
| 47 | DHX58 | −1.08197335 |
| 48 | GBGT1 | −1.074708355 |
| 49 | DUSP9 | −1.064035985 |
| 50 | DCI | −1.062701828 |
| 51 | B4GALT2 | −1.059756082 |
| 52 | MTR | −1.056286556 |
| 53 | NT5C2 | −1.05018509 |
| 54 | QPRT | −1.049591622 |
| 55 | XYLT1 | −1.047385174 |
| 56 | HSD3B2 | −1.04732817 |
| 57 | XYLT1 | −1.036614615 |
| 58 | ARL4D | −1.019904997 |
| 59 | GPT2 | −1.011081535 |
| 60 | OAT | −1.010517995 |
| 61 | RFXAP | −1.003540255 |
| 62 | PDE11A | −1.002478419 |
| 63 | BCR | −0.999251848 |
| 64 | GNA11 | −0.991626211 |
| 65 | PDE4C | −0.984930103 |
| 66 | AADAT | −0.975251982 |
| 67 | DHRS3 | −0.973521016 |
| 68 | FOXN1 | −0.968230022 |
| 69 | PDE6G | −0.9516564 |
| 70 | G6PC2 | −0.95121304 |
| 71 | RPIA | −0.948277121 |
| 72 | IDI1 | −0.946325589 |
| 73 | ACSS1 | −0.94128658 |
| 74 | FHIT | −0.937047885 |
| 75 | UGT1A3 | −0.931929094 |
| 76 | FARS2 | −0.928956083 |
| 77 | A4GALT | −0.908491011 |
| 78 | GATM | −0.895916148 |
| 79 | CHST1 | −0.895703474 |
| 80 | AGPAT4 | −0.88197513 |
| 81 | NT5M | −0.87410687 |
| 82 | MVK | −0.858318935 |
| 83 | UGT2B10 | −0.857628906 |
| 84 | UGT2B17 | −0.856960142 |
| 85 | ARHGEF1 | −0.852379198 |
| 86 | NEURL | −0.851842404 |
| 87 | QPCT | −0.847575957 |
| 88 | GNAI3 | −0.829219679 |
| 89 | ATIC | −0.82882892 |
| 90 | PLA2G12A | −0.821612953 |
| 91 | DARS | −0.81509502 |
| 92 | AKR1C1 | −0.808430619 |
| 93 | B4GALT5 | −0.803111967 |
| 94 | FUT5 | −0.79631504 |
| 95 | COX10 | −0.795694682 |
| 96 | AKAP13 | −0.795177764 |
| 97 | AGXT | −0.789605076 |
| 98 | GNMT | −0.773857532 |
| 99 | HOXB4 | −0.764471864 |
| 100 | CAND1 | −0.762199552 |
| 101 | CLC | −0.750921964 |
| 102 | TFAP2A | −0.742107657 |
| 103 | HMGN1 | −0.735548972 |
| 104 | RAD9A | −0.732504897 |
| 105 | DPM2 | −0.729251026 |
| 106 | GNB3 | −0.726234721 |
| 107 | ECGF1 | −0.724543721 |
| 108 | ARPC3 | −0.702909265 |
| 109 | ACVR1B | −0.702654268 |
| 110 | CKS1B | −0.691779896 |
| 111 | SLC1A2 | −0.685561772 |
| 112 | UROS | −0.677327526 |
| 113 | CHST4 | −0.676867755 |
| 114 | NT5E | −0.670757804 |
| 115 | PIGL | −0.65968708 |
| 116 | C1GALT1 | −0.659678757 |
| 117 | PDE1A | −0.654666246 |
| 118 | DHX58 | −0.652757208 |
| 119 | ACP6 | −0.652623162 |

TABLE 10-continued

ISLET Hits from shRNA Functional Genomic Screen

| No. | Gene Symbol | Log2 [Fold Change (DAC/Control)] |
|---|---|---|
| 120 | NOS1 | −0.644362342 |
| 121 | RECQL4 | −0.633755166 |
| 122 | ACSS1 | −0.633060393 |
| 123 | NOS3 | −0.632040701 |
| 124 | RNF2 | −0.630757795 |
| 125 | LSS | −0.620183504 |
| 126 | ANP32A | −0.619584524 |
| 127 | RAG2 | −0.616472044 |
| 128 | BCL2L2 | −0.615745065 |
| 129 | CPE | −0.609647885 |
| 130 | CAPN9 | −0.599580474 |
| 131 | NOS1 | −0.599058437 |
| 132 | PRKAR2A | −0.597192073 |
| 133 | EP300 | −0.593769189 |
| 134 | FGFR2 | −0.575684434 |
| 135 | ISYNA1 | −0.565131625 |
| 136 | ARF3 | −0.541828408 |
| 137 | IPMK | −0.537456079 |
| 138 | COMT | −0.52800403 |
| 139 | BCL11B | −0.519258686 |
| 140 | HMGCS1 | −0.51409389 |
| 141 | GALNT14 | −0.513962202 |
| 142 | LSS | −0.501310443 |
| 143 | GALNS | −0.500766635 |
| 144 | FAH | −0.483477843 |
| 145 | AK3L1 | −0.482209621 |
| 146 | SULT1C2 | −0.469223229 |
| 147 | GLP1R | −0.442978594 |
| 148 | AGPAT2 | −0.425268269 |
| 149 | FOXP1 | −0.378827137 |

The targets of the shRNA compounds listed in Table 10 represent potential targets for the development of inhibitors that, when combined with decitabine, may have induced synthetic lethality in cancer cells. Of these potential shRNA targets, 16 are identified herein and represented in FIG. 14 as white bars. The 16 potential targets underwent further validation with independent targeting shRNAs to confirm that they are productive ISLET combinations. The 16 identified targets include shRNAs for: GNAZ, two DCT shRNAs, ITK, AURKA, CHST3, MAP2K2, CRAT, PDE1B, STAT5A, MEF2C, IL17D, PDE48, HSD3B2, PDE4C, and FUT5.

Figure 15:
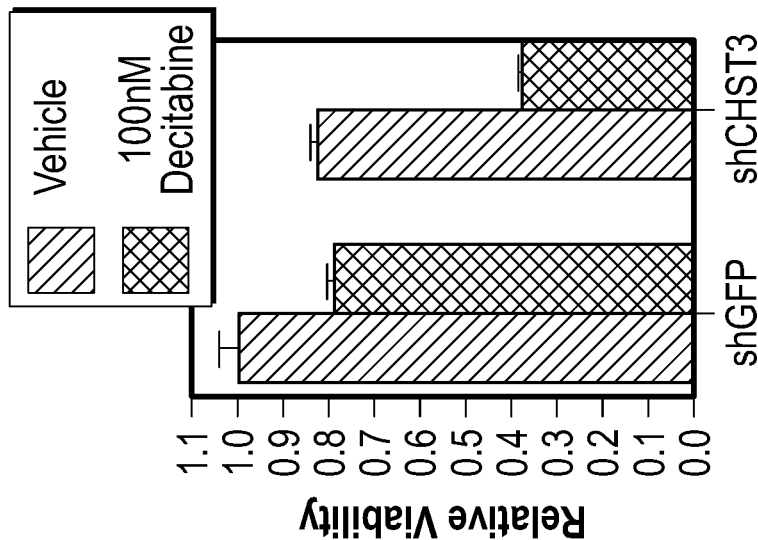
FIG. 15 is a bar graph illustrating DU145 cells treated with an shRNA sequence targeting CHST3 combined with vehicle control or 100 nM decitabine, compared to DU145 cells treated with non-targeting shRNAs (shGFP) in combination with a vehicle control and with 100 nM decitabine.

FIG. 15 shows independent validation of CHST as an Induced Synthetic Lethality with Epigenetic Therapy (ISLET) target in combination with decitabine. An shRNA targeting CHST specifically in combination with 100 nM decitabine caused significantly decreased DU145 cancer cell viability compared to the CHST shRNAs alone or decitabine alone. As shown in FIG. 15, the overall viability of DU145 cells was markedly higher for the vehicle control with decitabine but without shRNA targeting CHST than the sample comprising DU145 with shRNA targeting CHST together with decitabine.

FIG. 16 shows two different shRNAs targeting CRAT in combination with 100 nM decitabine each caused significantly decreased DU145 cancer cell viability compared to the CRAT shRNAs alone or decitabine alone. As shown in FIG. 16, the overall viability of DU145 cells was markedly higher for the vehicle control with decitabine but without shRNA targeting CRAT than for either of the two samples comprising DU145 with shRNA targeting CRAT together with decitabine.

FIG. 17 shows two different shRNAs targeting DCT in combination with 100 nM decitabine each caused significantly decreased DU145 cancer cell viability compared to the DCT shRNAs alone or decitabine alone. As shown in FIG. 17, the overall viability of DU145 cells was markedly higher for the vehicle control with decitabine but without shRNA targeting DCT than for either of the two samples comprising DU145 with shRNA targeting DCT together with decitabine.

FIG. 18 shows an shRNA targeting FUT5 in combination with 100 nM decitabine each caused significantly decreased DU145 cancer cell viability compared to the FUT5 shRNA alone or decitabine alone. As shown in FIG. 18, the overall viability of DU145 cells was markedly higher for the vehicle control with decitabine but without shRNA targeting FUT5 than for the sample comprising DU145 with shRNA targeting FUT5 together with decitabine.

FIG. 19 shows two different shRNAs targeting GNAZ in combination with 100 nM decitabine each caused significantly decreased DU145 cancer cell viability compared to the GNAZ shRNAs alone or decitabine alone. As shown in FIG. 19, the overall viability of DU145 cells was markedly higher for the vehicle control with decitabine but without shRNA targeting GNAZ than for either of the two samples comprising DU145 with shRNA targeting GNAZ together with decitabine.

FIG. 20 shows an shRNA targeting HSD3B2 in combination with 100 nM decitabine each caused significantly decreased DU145 cancer cell viability compared to the HSD3B2 shRNA alone or decitabine alone. As shown in FIG. 20, the overall viability of DU145 cells was markedly higher for the vehicle control with decitabine but without shRNA targeting HSD3B2 than for the sample comprising DU145 with shRNA targeting HSD3B2 together with decitabine.

FIG. 21 shows two different shRNAs targeting IL17D in combination with 100 nM decitabine each caused significantly decreased DU145 cancer cell viability compared to the IL17D shRNAs alone or decitabine alone. As shown in FIG. 21, the overall viability of DU145 cells was markedly higher for the vehicle control with decitabine but without shRNA targeting IL17D than for either of the two samples comprising DU145 with shRNA targeting IL17D together with decitabine.

FIG. 22 shows two different shRNAs targeting ITK in combination with 100 nM decitabine each caused significantly decreased DU145 cancer cell viability compared to the ITK shRNAs alone or decitabine alone. As shown in FIG. 22, the overall viability of DU145 cells was markedly higher for the vehicle control with decitabine but without shRNA targeting ITK than for either of the two samples comprising DU145 with shRNA targeting ITK together with decitabine.

FIG. 23 shows two different shRNAs targeting MAP2K2 in combination with 100 nM decitabine each caused significantly decreased DU145 cancer cell viability compared to the MAP2K2 shRNAs alone or decitabine alone. As shown in FIG. 23, the overall viability of DU145 cells was markedly higher for the vehicle control with decitabine but without shRNA targeting GNAZ than for either of the two samples comprising DU145 with shRNA targeting MAP2K2 together with decitabine.

FIG. 24 shows two different shRNAs targeting MEF2C in combination with 100 nM decitabine each caused significantly decreased DU145 cancer cell viability compared to the MEF2C shRNAs alone or decitabine alone. As shown in FIG. 24, the overall viability of DU145 cells was markedly higher for the vehicle control with decitabine but without shRNA targeting MEF2C than for either of the two samples comprising DU145 with shRNA targeting MEF2C together with decitabine.

FIG. 25 shows two different shRNAs targeting PDE1B in combination with 100 nM decitabine each caused significantly decreased DU145 cancer cell viability compared to the PDE1B shRNAs alone or decitabine alone. As shown in FIG. 25, the overall viability of DU145 cells was markedly higher for the vehicle control with decitabine but without shRNA targeting PDE1B than for either of the two samples comprising DU145 with shRNA targeting PDE1B together with decitabine.

FIG. 26 shows four different shRNAs targeting PDE4B in combination with 100 nM decitabine each caused significantly decreased DU145 cancer cell viability compared to the PDE4B shRNAs alone or decitabine alone. As shown in FIG. 26, the overall viability of DU145 cells was markedly higher for the vehicle control with decitabine but without shRNA targeting PDE4B than for any of the four samples comprising DU145 with shRNA targeting PDE4B together with decitabine.

FIG. 27 shows four different shRNAs targeting PDE4C in combination with 100 nM decitabine each caused significantly decreased DU145 cancer cell viability compared to the PDE4C shRNAs alone or decitabine alone. As shown in FIG. 27, the overall viability of DU145 cells was markedly higher for the vehicle control with decitabine but without shRNA targeting PDE4C than for any of the four samples comprising DU145 with shRNA targeting PDE4C together with decitabine.

FIG. 28 shows two different shRNAs targeting STAT5A in combination with 100 nM decitabine each caused significantly decreased DU145 cancer cell viability compared to the STAT5A shRNAs alone or decitabine alone. As shown in FIG. 28, the overall viability of DU145 cells was markedly higher for the vehicle control with decitabine but without shRNA targeting STAT5A than for either of the two samples comprising DU145 with shRNA targeting STAT5A together with decitabine.

Example 8—Combination of MBD Protein Inhibitors and RAR Agonists Showed In Vitro and In Vivo Tumor Suppression Retinoic Acid Pathway Activation To determine whether MBD2 protein inhibitors triggered retinoic acid signaling pathway activation, KCC-08 was administered to PC-3 human prostate cancer cells transfected with a heterologous reporter plasmid responsive to the presence of retinoic acid signaling (pRARE-luciferase), and the cells were used to assess reactivation of the retinoic acid response signaling pathway. The cancer cells were treated with a vehicle control or KCC-08 (10 μM) both with and without isotretinoin (5 μM) for 72 hours, and then assayed for luciferase reporter production.

As shown in FIG. 29A and as detailed in Table 11 below, luciferase activity was enhanced by KCC-08, and was even further enhanced upon stimulation by isotretinoin in combination with KCC-08 such that the combination of KCC-08 and isotretinoin synergistically enhanced retinoic acid signaling pathway activation.

TABLE 11

RAR Reporter Activity in KCC-08 with and without Isotretinoin

| Treatment | Trial 1 | Trial 2 | Trial 3 | Trial 4 | Trial 5 | Trial 6 | Average | Standard Deviation |
|---|---|---|---|---|---|---|---|---|
| Vehicle control | 0.88 | 1.17 | 0.95 | 1.00 | 1.02 | 0.98 | 1.00 | 0.09 |
| Isotretinoin | 1.66 | 1.77 | 1.62 | 1.42 | 1.47 | 1.46 | 1.57 | 0.14 |
| KCC-08 | 2.08 | 2.31 | 1.96 | 2.46 | 2.36 | 2.28 | 2.24 | 0.19 |
| Isotretinoin + KCC-08 | 5.51 | 5.36 | 5.54 | 4.76 | 5.11 | 5.24 | 5.25 | 0.29 |

To assay for cancer clonogenic survival, PC-3 cancer cells were seeded into 6-well plates at 5,000 cells/well and allowed to attach overnight. Next, the cells were treated for 72 hours with vehicle control or KCC-08, both with and without isotretinoin, washed three times with phosphate-buffered saline, and then placed back into complete growth medium. Ten days later, colonies founded by surviving cells were detected using crystal violet staining. Accordingly, it was determined that retinoic acid signaling pathway restoration by KCC-08 and isotretinoin reduced clonogenic survival after a 72-hour exposure, as shown in FIG. 29B and in Table 12, below, showing the average of 12-27 independent replicates.

TABLE 12

Clonogenic Survival Relative to Control

| Treatment | Average | Standard Deviation |
|---|---|---|
| Vehicle control | 100.00 | 7.78 |
| Isotretinoin | 96.62 | 7.48 |
| KCC-08 | 96.86 | 7.19 |
| Isotretinoin + KCC-08 | 61.44 | 22.24 |

In Vivo Tumor Suppression

For cancer xenograft growth suppression, one million human PC-3 prostate cancer cells were suspended in Matrigel and inoculated into the flanks of Male Fox1-nude mice provided by Jackson Laboratory (Bar Harbor, Me.). When the resultant xenograft tumors were measurable two weeks later, the tumor-bearing mice were treated with KCC-08, given by intraperitoneal infection in saline for 5 of 7 days at 1 mg/kg for week 1 and then 0.5 mg/kg for 5 of 7 days for week 2. Isotretinoin was given by oral gavage in peanut oil at 30 mg/kg for the same 5 of 7 days as the KCC-08 for weeks 1 and 2. For week 3, isotretinoin was given by oral gavage in peanut oil at 30 mg/kg for 5 of 7 days, and KCC-08 was not administered. Tumors were measured 3 times a week for 3 weeks, and the volume was estimated by using the formula $4/3*\Pi*width*length*depth$.

As shown in FIG. 29C and Table 13, below, the combination of KCC-08 and isotretinoin synergistically suppressed tumor growth in vivo, even when isotretinoin was administered after KCC-08 administration had ceased.

TABLE 13

| | Control | | KCC-08 | | Isotretinoin | | KCC-08 + Isotretinoin | |
|---|---|---|---|---|---|---|---|---|
| Day | Average | Standard Deviation | Average | Standard Deviation | Average | Standard Deviation | Average | Standard Deviation |
| 1 | 100 | — | 100 | — | 100 | — | 100 | — |
| 4 | 123.42 | 27.22 | 151.16 | 83.10 | 161.09 | 37.76 | 121.37 | 40.79 |
| 8 | 185.32 | 51.54 | 223.22 | 50.77 | 238.81 | 55.48 | 150.41 | 50.46 |
| 11 | 207.16 | 73.19 | 250.94 | 47.18 | 315.81 | 72.50 | 146.98 | 51.25 |
| 15 | 291.89 | 101.14 | 338.37 | 98.14 | 394.27 | 99.54 | 148.19 | 71.24 |
| 18 | 351.90 | 179.12 | 406.04 | 100.58 | 488.75 | 157.32 | 193.54 | 90.84 |
| 22 | 374.69 | 186.53 | 452.09 | 119.19 | 522.19 | 119.19 | 257.57 | 130.07 |

Percent average xenograft tumor volume relative to baseline

Example 9—Chemical Library Screen to Identify ISLET Hits with Decitabine

A chemical library screen (Johns Hopkins Drug Library, JHDL) was used with and without the DNMT inhibitor decitabine in order to identify those compounds in the library that synergistically inhibited cancer cell growth compared to decitabine or the compound alone. Two stages of screening were performed. In the first stage, 3800 compounds in the JHDL library were administered to PC-3 prostate cancer cells in a single dose of 5 micromolar exposed for three days after four days of exposure to either 100 nM Decitabine or a vehicle control. 131 compounds were identified showing>50% growth inhibition.

In a second stage, 64 of the 131 identified compounds were assessed in full dose response matrix of each of the 64 compounds alone (0-10 μM) and in combination with decitabine (0-10 μM). Cells were exposed to each dose of decitabine for four consecutive days prior to addition of each dose of the identified compounds for three consecutive days. Compounds were identified to have synergistic growth inhibition when combined with decitabine if the Bliss independence score sum across all dose combinations was greater than zero. FIG. 30 is a bar graph illustrating the Bliss Independence score values for the cells of the compounds identified. The following 22 compounds were identified: colchicine, strophanthidin, vinorelbine, NH125, docetaxel, periplocymarin, topotecan, cladribine, cytarabine, RO31-8220, ouabain, gemcitabine, PI828, mycophenolic acid, GW843682, bleomycin, aclarubicin, ER27319, carboplatin, anisomycin, SB218078, and valinomycin.

This chemical library screening approach identified multiple classes of drugs, including kinase inhibitors, microtubule agents, nucleoside analogs, antibiotics, and other agents as significant ISLET hits.

What is claimed is:

1. A method for treating cancer, the method comprising administering to a subject in need thereof an effective amount of decitabine and an effective amount of alisertib, wherein the cancer is prostate cancer, ovarian cancer, lung cancer, colon cancer, central nervous system cancer, or breast cancer.

2. The method according to claim 1, wherein the subject is human.

3. The method according to claim 1, wherein the administration of the decitabine and the administration of the alisertib is sequential.

4. The method according to claim 3, wherein the decitabine is administered before administration of the alisertib.

5. The method according to claim 1, wherein the administration of the decitabine and the administration of the alisertib is simultaneous.

6. The method of claim 1, wherein the cancer is prostate cancer.

7. The method of claim 1, wherein the cancer is ovarian cancer.

8. The method of claim 1, wherein the cancer is lung cancer.

9. The method of claim 1, wherein the cancer is colon cancer.

10. The method of claim 1, wherein the cancer is central nervous system cancer.

11. The method of claim 1, wherein the cancer is breast cancer.

\* \* \* \* \*